(12) United States Patent
Wang et al.

(10) Patent No.: US 9,422,352 B2
(45) Date of Patent: Aug. 23, 2016

(54) PTD-SMAD7 THERAPEUTICS

(71) Applicant: The Regents of the University of Colorado, a body corporate, Denver, CO (US)

(72) Inventors: Xiao-Jing Wang, Greenwood Village, CO (US); Qinghong Zhang, Englewood, CO (US); Yosef Refaeli, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/201,488

(22) Filed: Mar. 7, 2014

(65) Prior Publication Data

US 2014/0288006 A1    Sep. 25, 2014

Related U.S. Application Data

(60) Provisional application No. 61/775,252, filed on Mar. 8, 2013.

(51) Int. Cl.
*A61K 38/00*    (2006.01)
*C07K 14/47*    (2006.01)
*A61K 48/00*    (2006.01)

(52) U.S. Cl.
CPC ......... *C07K 14/4703* (2013.01); *C07K 14/4702* (2013.01); *A61K 38/00* (2013.01); *A61K 48/005* (2013.01); *C07K 2319/10* (2013.01); *C07K 2319/20* (2013.01); *C07K 2319/23* (2013.01); *C12N 2800/22* (2013.01)

(58) Field of Classification Search
None
See application file for complete search history.

(56) References Cited

U.S. PATENT DOCUMENTS

| | | |
|---|---|---|
| 4,684,611 A | 8/1987 | Schilperoort et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,610,042 A | 3/1997 | Chang et al. |
| 5,656,610 A | 8/1997 | Shuler et al. |
| 5,670,488 A | 9/1997 | Gregory et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,871,986 A | 2/1999 | Boyce |
| 5,945,100 A | 8/1999 | Fick |
| 5,981,274 A | 11/1999 | Tyrrell et al. |
| 5,994,624 A | 11/1999 | Trolinder et al. |
| 6,166,084 A * | 12/2000 | Bloor ........................... 514/613 |
| 6,251,628 B1 | 6/2001 | Nakao et al. |
| 6,605,443 B1 | 8/2003 | Nakao et al. |
| 2007/0178439 A1 | 8/2007 | Smith et al. |
| 2007/0231401 A1 | 10/2007 | Tseng et al. |
| 2009/0155193 A1 | 6/2009 | Joabsson et al. |

FOREIGN PATENT DOCUMENTS

| | | |
|---|---|---|
| CN | 101316602 | 12/2008 |
| JP | 2004-537982 A | 12/2004 |
| WO | WO-94/09699 | 5/1994 |
| WO | WO-95/06128 | 3/1995 |
| WO | WO-99/50296 | 10/1999 |
| WO | WO 02/085306 | 10/2002 |
| WO | WO-03/006057 | 1/2003 |
| WO | WO-2007/038686 | 4/2007 |
| WO | WO-2012/040295 | 3/2012 |

OTHER PUBLICATIONS

Chong et al, An ExpandedWWDomain Recognition Motif Revealed by the Interaction between Smad7 and the E3 Ubiquitin Ligase Smurf2 (J. Biol. Chem. 2006, 281:17069-17075).*
Elliott et al, Role of Transforming Growth Factor Beta in Human Cancer (J Clin Oncol 23:2078-2093, 2005).*
Altschul et al. "Basic Local Alignment Search Tool" J. Mol Biol. 215:403-410 (1990).
Aragon, et al., "Structural Basis for the Versatile Interactions of Smad7 with Regulator WW Domains in TGF-beta Pathways" Structure 20:1726-1736 (2012).
Ashcroft et al., "Mice lacking Smad3 show accelerated wound healing and an impaired local inflammatory response," Nat Cell Biol 1:260-266, 1999.
Chen C., and Okayama, H., "High-efficiency transformation of mammalian cells by plasmid DNA," Mol Cell Biol. Aug. 1987; 7(8): 2745-2752.
Feng, et al., "Specificity and Versatility in TGF-beta Signaling Through SMADS," The Annual Review of Cell and Developmental Biology, 2005, vol. 21, pp. 659-693.

(Continued)

*Primary Examiner* — Marcela M Cordero Garcia
*Assistant Examiner* — Sergio Coffa
(74) *Attorney, Agent, or Firm* — Foley & Lardner LLP

(57) ABSTRACT

The present technology provides methods and compositions for the treatment of inflammatory and/or tissue damage conditions. In particular, the use of Smad7 compositions delivered locally or systemically to a site of inflammation and/or tissue damage is described. Other specific embodiments concern treatment or prevention of side effects caused by radiation and/or chemotherapy, including but not limited to oral and gastric mucositis. Also provided are codon-optimized nucleic acids encoding for Smad7 fusion proteins.

11 Claims, 15 Drawing Sheets

(56) References Cited

OTHER PUBLICATIONS

Gopal T., "Gene transfer method for transient gene expression, stable transformation, and cotransformation of suspension cell cultures," Mol Cell Biol., May 1985, 5(5), pp. 11880131190.

Graham, F., and van der Eb, A., "A new technique for the assay of infectivity of human adenovirus 5 DNA," Virology, Apr. 1973, vol. 52, Issue 2, pp. 456-457.

Han et al., Smad7-Induced Beta-Catenin Degradation Alters Epidermal Appendage Development, Dev Cell Biol 11, Sep. 2006, pp. 301-312.

Hong et al., Smad 7 binds to the adaptors TAB2 and TAB3 to block recruitment of the kinase TAK1 to the adaptor TRAF2, Nat Immunology, 8, 504-513, 2007.

Hoot, et al. "Keratinocyte-specific Smad2 ablation results in increased epithelial-mesenchymal transition during skin cancer formation and progression," J.Clininvest 118, pp. 2722-2732 (2008).

Hoot, K.E. et al., "HGF upregulation contributes to angiogenesis in mice with keratinocyte-specific Smad2 deletion," J Clin Invest 120, 3606-3616 (2010).

International Search Report and Written Opinion for PCT/US2014/022052, mailed Jul. 14, 2014.

Kaeppler, H., et al., "Silicon carbide fiber-mediated DNA delivery into plant cells," Plan Cell Rep 9, 1990, pp. 415-418.

Kaneda et al., "Introduction and Expression of the Human Insulin Gene in Adult Rat Liver*" J. Biol. Chem 264:12126-12129 (1989).

Karlin and Altschul Methods for Assessing the Statistical Significance of Molecular Sequence Features by Using General Scoring Schemes, Proc. Natl. Acad. Sci. USA 87: 2264-2268, 1990.

Karlin and Altschul "Applications and statistics for multiple high-scoring segments in molecular sequences," Proc. Natl. Acad. Sci, USA 90:5873-5877, 1993.

Kato, K., et al., "Direct injection of hepatitis B virus DNA into liver induced hepatitis in adult rats," J Biol Chem, Nov. 1991;266, pp. 3361-3364. (might be listed under pp. 22071-4).

Mallawaarachchi et al., "Smad7 Gene Transfer Attenuates Adventitial Cell Migration and Vascular Remodeling after Balloon Injury," Arterioscler Thromb Vasc Biol 25: 1383-1387, 2005.

Munshi et al., "Clonogenic Cell Survival Assay", Methods in molecular medicine 110, 21-28 (2005).

Nicolau, C., and Sene, C., "Liposome-mediated DNA transfer in eukaryotic cells: Dependence of the transfer efficiency upon the type of liposomes used and the host cell cycle stage," Biochimica et Biophysica Acta (BBA)—Molecular Cell Research, vol. 721, Issue 2, Oct. 11, 1982, pp. 185-190.

Nicolau, C., et al., "Liposomes as carries for in vivo gene transfer expression," 1987, Meth. Enzymol. 149, pp. 157-176.

Omirulleh, S et al., "Activity of a chimeric promoter with the doubled CaMV 35S enhancer element in protoplast-derived cells and transgenic plants in maize," 1993, Plant Mol Biol 21:415-428.

Owens et al., "Epidermal Smad4 Deletion Results in Aberrant Wound Healing," Am J Pathol 176:122-133, 2010.

Owens, et al., "Smad4-dependent desmoglein-4 expression contributes to hair follicle integrity," Dev. Biol. 322, pp. 156-166 (2008).

Potrykus, I., et al., "Molecular and general genetics of a hybrid foreign gene introduced into tobacco by direct gene transfer," Molecular and General Genetics MGG, May 28, 1985, vol. 199, Issue 2, pp. 169-177.

Rippe, R., et al., "DNA-mediated gene transfer into adult rat hepatocytes in primary culture," Mol Cell Biol. Feb. 1990; 10(2): 689013695.

Robbins P., and Ghivizzani S., "Viral vectors for gene therapy," Pharmacol Ther. Oct. 1998 80(1):35-47.

Saika et al., "Expression of Smad7 in Mouse Eyes Accelerates Healing of Corneal Tissue after Exposure to Alkali", Am J. Pathol 166:1405-1418, 2005.

Saika et al., "Transient adenoviral gene transfer of Smad7 prevents injury-induced epithelial-mesenchymal transition of lens epithelium in mice," Lab Invest 84:1259-1270, 2004.

Sumiyoshi et al., "Exogenous Smad3 Accelerates Wound Healing in a Rabbit Dermal Ulcer Model," J Invest Dermatol 123:229-236, 2004.

Wang et al., "Role of TGFbeta-Mediated Inflammation in Cutaneous Wound Healing," J Investig Dermatol Symp Proc 11: 112-117, 2006.

Wong, T., et al., "Appearance of B-lactamase activity in animal cells upon liposome-mediated gene transfer," 1980, Gene, 10, pp. 87-94.

Zhang et al., "Smad7 Antagonizes Transforming Groth Factor Beta Signaling in the Nucleus by Interfering with Functional Smad-DNA Complex Formation," Molecular and Cellular Biology, vol. 27, No. 12, Jun. 2007, pp. 4488-4499.

Funaki et al. "Ex Vivo Transfer of Smad7 Decreases Damage to the Corneal Endothelium After Penetrating Keratoplasty" Journal of Opthalmology 2008.

G. Han et al., Overexpression of Smad7 in Keratinocytes Accelerates Cutaneous Wound Healing, Wound Repair and Regeneration, 2004, vol. 12, No. 2, p. A11, No. 036.

Liu Bo et al., Expression of TAT-Smad7-HA fusion protein and validation of its transduction activity, Di-San Junyi Daxue Xuebao, 2008, vol. 30, No. 23, p. 2198-2202. (abstract), CAPLUS[online].

Liu, B. et al., "Expression of TAT-Smad7-HA fusion protein and validation of its transduction activity", Journal of Third Military Medical University (2008), vol. 30, pp. 2198-2202, 9 page English translation from Chinese.

Liu, B. et al., "Expression of TAT-SMAD7-HA Fusion Protein and Validation of its Transduction Activity," 2008, Article No. 1000/5404(2008) 23/2198-05, 19 pages. (English translation of original article).

Office Action for JP 2013-530249 dated Aug. 31, 2015 (with EN translation).

Yamanaka et al., Gene transfer of Smad7 modulates injury-induced coujunctival wound healing in mice, Molecular Vision, 2006, 12:841-851.

Office Action issued Dec. 10, 2015 for IL 225406 (with English translation).

US Office Action on U.S. Appl. No. 14/750,557 dated Jan. 14, 2016.

Gantwerker, Eric A. et al, "Skin: Histology and Physiology of Wound Healing," Facial Plastic Surgery Clin N Am 19, 2011.

Gauglitz Gerd G. et al, "Hypertrophic Scarring and Keloids: Pathomechansims and Current and Emerging Treatment Strategies," Mol Med 17 (1-2) 113-125, Jan.-Feb. 2011.

Han, Gangwen et al., "Temporal Smad7 Transgene Induction in Mouse Epidermis Accelerates Skin Wound Healing," The American Journal of Pathology, vol. 179, No. 4, Oct. 2011.

Marttala, Jaana et al., "Keloids: Animal models and pathologic equivalents to study tissue fibrosis," Matrix Biol. 2016.

English Translation of Office Action for JP 2013-5320249 dispatched Mar. 28, 2016.

Smith, Oliver J et al., "The natural history and spontaneous resolution of keloid scars," Journal of Plastic, Reconstructive & Aesthetic Surgery, 67, 87-92, 2014.

Ud-Din, Sara et al., "New Insights on Keloids, Hypertrophic Scars, and Striae," Dermatol Clin 32, 193-209, 2014.

Yates, Cecilia C. et al, "Skin Wound Healing and Scarring: Fetal Wounds and Regenerative Restitution," Birth Defects Research (Part C) 96:325-333, 2012.

Liang,, Ying-min et al., "TAT protein transduction domain mediates transmembrane delivery of BCR/ABL fusion protein into tissue cells of mice in vivo" Journal of Third Military Medical University, vol. 24, No. 4, Apr. 2002, pp. 421-424. (English abstract only).

Notice of Allowance on U.S. Appl. 13/822,173, mailed Mar. 17, 2015.

English translation of Second Office Action on Chinese Application 201180051033.3, issued Mar. 17, 2015.

Brooks, H. "Tat peptide-mediated cellular delivery: back to basics," Advanced Drug Delivery Reviews, vol. 57, Issue 4, Feb. 2005, pp. 559-577.

Cardarelli, F., et al., "Tuning the Transport Properties of HIV-1 Tat Arginine-Rich Motif in Living Cells," Traffic, Apr. 2008, vol. 9, Issue 4, pp. 528-539.

Caron, et al., "Endosome disruption enhances the functional nuclear delivery of Tat-fusion proteins", Biochem Biophys Res Comm, (2004), vol. 319, pp. 12-20.

(56) References Cited

OTHER PUBLICATIONS

Cawley, M. and Benson, L., "Current Trends in Managing Oral Mucositis," Clin. Journ. of Onocology Nursing, Oct. 2005, vol. 9, No. 5, pp. 584-592.
Elmotasem, H., "Chitosan-alginate blend films for the transdermal delivery of meloxicam," J Pharm Sci. 2008, 3(1), pp. 12-29.
Extended Search Report for European Patent Application 11827421.6, mailed Dec. 3, 2014.
Fechheimer, M., et al., "Transfection of mammalian cells with plasmit DNA by scrape loading and sonication loading," Dec. 1987, Proc. Natl. Acad. Sci, vol. 84, pp. 8463-8467.
First Office Action received in Chinese Appln. No. 201180051033.3 dated Jun. 27, 2014.
Fischer, "Cellular Uptake Mechanisms and Potential Therapeutic Utility of Peptidic Cell Delivery Vectors: Progress 2001-206," Med. Res. Rev., 2007, 27(6), pp. 755-796.
Fraley, R., et al., "Entrapment of a bacterial plasmid in phospholipid vesicles: Potential for gene transfer," 1979, Proc. Natl. Acad. Sci. 76, pp. 3348-3352.
Funaki et al., "Ex vivo transfer of Smad7 decreases damage to the corneal endothelium after penetratingkeratoplasty," Japanese Journal of Opthamology, vol. 52, No. 3, Jul. 27, 2008, pp. 204-210.
Han, G et al., "Overexpression of Smad7 in Keratinocytes Accelerates Cutaneous Wound Healing," Wound Repair and Regeneration, vol. 12, No. 2, Mar. 2004, pp. A1-A40.
Han, G., et al., "Preventative and therapeutic effects of Smad7 on radiation-induced oral mucositis," Nature Medicine, Apr. 2013, vol. 19, No. 4, pp. 421-430.
Hariharan, et el., "Structure-function relationship of inhibitory Smads: Structural flexibility contributes to functional divergence", Proteins, (2008), vol. 71, pp. 1853-1862.
Harland, R. and Weintraub, H., "Translation of mRNA injected into Xenopus oocytes is specifically inhibited by antisense RNA," Sep. 1985, JCB, vol. 101, No. 3, pp. 1094-2099.

Hong, S., et al., "Smad7 binds to the adaptors TAB2 and TAB3 to block recruitment of the kinase TAK1 to the adaptor TRAF2," Nature Immunology, May 2007, vol. 8, No. 5, pp. 504-513.
Imai, E., et al., "Towards gene therapy for renal diseases," Nephrologie, 1998, 19(7), pp. 397-402. Abstract only.
International Search Report and Written Opinion received for PCT/US2011/052499 dated Apr. 9, 2012.
Kalvala, A., et al., "Enhancement of gene targeting in human cells by intranuclear permeation of the Saccharomyces cerevisiae Rad52 protein," Nucl. Acids Res. (2010) 38 (14): e149.
Li, A., et al., "Latent TGFbeta1 overexpression in keratinocytes results in a severe psoriasis-like skin disorder," Apr. 21, 2004, vol. 23, Issue 8, pp. 1770-1781.
Massague, J., et al., "Smad transcription factors," Genes & Dev. 2005. 19: 2783-2810.
Non-final Office Action received for U.S. Appl. No. 13/822,173 dated May 22, 2014.
Restriction Requirement received for U.S. Appl. No. 13/822,173 DTD Jan. 16, 2014.
Robbins P., and Ghivizzani S., "Viral vectors for gene therapy," Pharmacol Ther. Oct. 1998;80(1):35-47.
Robbins P., et al., "Viral vectors for gene therapy," Trends Biotechnol. Jan. 1998;16(1):35-40.
Saika et al., "Transient adenoviral gene transfer of Smad7 prevents formation of ulceration and scarring of the cornea following an alkali exposure in mice," IOVS, May 1, 2005, p. 1165, retrieved from the Internet: URL:http://abstracts,iovs.org/cgi/content/abstract/45/5/1165 retrieved Sep. 25, 2014.
Wang, N., et al., "NF-kB," 2008, Anat. Res. vol. 30, No. 2, pp. 141-144. (English Translation Not Available).
Yamanaka et al.,j "Gene transfer of Smad7 modulates injury-induced conjunctival wound healing in mice," Molecular vision, Aug. 1, 2006, pp. 841-851.
Zhang, S., et al., "Smad7 Antagonizes Transforming Growth Factor 3B2 Signaling in the Nucleus by Interfering with Functional Smad-DNA Complex Formation," Mol Cell Biol. Jun. 2007; 27(12): 4488-4499.

\* cited by examiner

PTD-SMAD7 THERAPEUTICS

CROSS-REFERENCE TO RELATED APPLICATIONS

The present application claims priority to U.S. provisional patent application Ser. No. 61/775,252, filed Mar. 8, 2013, which is incorporated by reference herein in its entirety.

STATEMENT OF GOVERNMENT INTEREST

This invention was made with government support under grant number AR061796 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 28, 2014, is named 089491-0302_SL.txt and is 92,533 bytes in size.

BACKGROUND

Oral mucositis, a severe oral ulceration, is a common adverse effect of a large dose of radiation for bone marrow transplant or craniofacial radiotherapy for cancer. Severe oral mucositis could require feeding tubes, management of severe pain, and prematurely halting radiotherapy. Excessive inflammation and epithelial ablation are key features of oral mucositis.

Palifermin, a KGF (human keratinocyte growth factor) recombinant protein, is approved for preventing oral mucositis in bone-marrow transplant patients. Two Palifermin clinical trials in head and neck cancer patients showed that Palifermin reduced severe oral mucositis incidence from 67% and 69% to 51% and 54%, respectively. Other oral mucositis drugs in clinical trials or pre-clinical studies include growth factors, agents for radioprotection, anti-inflammatory agents or immune modulators.

The modest effects of Palifermin and drugs being developed in the above mentioned categories highlight the need for identification of biomarkers for novel therapies. However, the lack of routine diagnostic biopsies or discarded tissues from oral mucositis patients has hindered this effort.

Cutaneous wound healing progresses through three overlapping phases: inflammation, tissue formation, and tissue remodeling. These are dynamic processes that involve interactions among the epidermis, leukocytes, extracellular matrix (ECM), and dermal fibroblasts. In response to skin injury, blood clots, infiltrated inflammatory cells and other cell types in the wound release multiple cytokines and chemokines. These cytokines initiate fibroblast proliferation and synthesis of ECM that fill the wound deficit and lead to wound closure. Meanwhile, keratinocytes at the wound edge begin to proliferate and migrate to cover the wound surface. Underneath the re-epithelialized epidermis, new stroma, called granulation tissue, begins to fill the wound space, which contains provisional ECM, inflammatory cells, fibroblasts, and blood vessels. Once the wound area is filled with the granulation tissue and covered by newly re-epithelialized epidermis, the process of wound closure is completed. Later on, the wound gradually returns to normal strength and texture through tissue remodeling.

Among the many molecules known to influence wound healing, transforming growth factor β (TGF-β) has the broadest spectrum of action, affecting all cell types that are involved in all stages of wound healing (Feng et al., *Annu Rev Cell Dev Biol* 21:659-693, 2005). The various functions of TGF-β are mediated by a number of signaling molecules, including the Smad family members. When a ligand binds to TGF-β type I and type II receptors (TGFβRI and TGF-βRII), TGF-βRI phosphorylates Smad2 and Smad3. Phosphorylated Smad2 and Smad3 bind a co-Smad, Smad4, to form heteromeric Smad complexes and translocate into the nucleus to regulate transcription of TGF-β target genes.

TGF-β signaling has been reported to exert both positive and negative effects on wound healing (Wang et al., *J Investig Dermatol Symp Proc* 11: 112-117, 2006). For instance, Smad3 deficient mice, in which TGF-β signaling is partially abrogated, exhibit accelerated wound healing (Ashcroft et al., *Nat Cell Biol* 1:260-266, 1999). In contrast, the introduction of exogenous Smad3 to wound sites to enhance TGF-β signaling also accelerated wound healing in a rabbit dermal ulcer model (Sumiyoshi et al., *J Invest Dermatol* 123:229-236, 2004). Skin wounds in Smad4-deficient mice have a dramatic increase in inflammation and angiogenesis causing a delay in wound closure and formed an excessive scar (Owens et al., *Am J Pathol* 176:122-133, 2010). Transient adenoviral gene transfer of Smad7, an antagonist of TGF-β signaling, in corneal epithelium and stroma resulted in accelerated corneal wound healing with reduced inflammation (Saika et al., *Am J Pathol* 166:1405-1418, 2005). Further, Smad7 gene transfer to the lens epithelium and stroma prevented injury-induced epithelial-mesenchymal transition of lens epithelial cells and suggests a potential role of Smad7 in prevention of capsular fibrosis (Saika et al., *Lab Invest* 84:1259-1270, 2004). However, adenoviral vector delivery of Smad7 to balloon injury in rat carotid arteries resulted in reduced vascular healing (Mallawaarachchi et al., *Arterioscler Thromb Vasc Biol* 25: 1383-1387, 2005). These studies suggest that the effects of TGF-β signaling components, such as Smad7, on wound healing are complex and highly context-specific. Additionally, the effect of Smad7 may not always be explained by its role in TGF-β signaling. For instance, Smad7 has also been shown to interact with components of the Wnt/β-catenin (Han et al., *Dev Cell Biol* 11:301-312, 2006) and the TNFβ/NF-κB (Hong et al., *Nat Immunol* 8:504-513, 2007) families.

SUMMARY

The present technology provides a nucleic acid molecule comprising a codon-optimized human Smad7 cDNA nucleotide sequence. In some embodiments, the codon-optimized human Smad7 nucleotide sequence may include one or more codons for arginine optimized for expression in one or more of bacteria or yeast, including one or more codons for serine optimized for expression in one or more of bacteria or yeast, and/or including one or more codons for histidine optimized for expression in one or more of bacteria or yeast. In some embodiments, the codon-optimized human Smad7 nucleotide sequence may include 28 serine codons, 6 histidine codons, and 9 arginine codons optimized for expression in one or more of bacteria or yeast. In some embodiments, the codon-optimized human Smad7 nucleotide sequence may be selected from the group consisting of SEQ ID NOs: 9, 21, 23, 24, 26, 28, 30, 32-34, 36, 38, and 39. In some embodiments, the codon-optimized human Smad7 nucleotide sequence may have about 65 to 75 percent homology to human Smad7 cDNA, may comprise a nucleotide sequence encoding an N-terminal fragment SMAD7, may comprise a nucleotide sequence encoding a C-terminal fragment of SMAD7, may comprise nucleotides encoding amino acids 2-258 of the human Smad7 protein, may comprise nucleotides encoding amino acids 259-426 of the human Smad7 protein, or may comprise nucleotides encoding amino acids 204-258 of the human Smad7 protein. In some embodiments, any of the foregoing may further comprise a nucleotide sequence encoding a protein transduction domain, such as Tat. In some embodiments, any of the foregoing may also further comprise a nucleotide sequence encoding one or more of an epitope tag or a purification tag, such as V5, glutathione-S-transferase, or 6-Histidine (SEQ ID NO: 40).

In some embodiments, any of the foregoing may be isolated and/or purified. In some embodiments, any one of the foregoing may also encode a polypeptide having one or more biological activities selected from the group consisting of reducing or eliminating phosphorylation of Smad2, reducing or eliminating nuclear translocation of the NF-κB p50 subunit, increasing cell proliferation, reducing apoptosis, reducing radiation-induced DNA damage, reducing inflammation, reducing angiogenesis, promoting healing in oral mucositis, promoting wound healing, and treating auto-immune disease. In some embodiments, pharmaceutical compositions comprising the nucleic acid molecules above and one or more pharmaceutically acceptable excipients are provided. In some embodiments, expression vectors comprising the nucleic acid molecules above operably linked to a promoter are provided, as are host cells comprising such expression vectors, and pharmaceutical compositions comprising such vectors and host cells with one or more pharmaceutically acceptable excipients.

In one aspect, a protein molecule comprising a human Smad7 protein having leucine at position 216 is provided. In some embodiments, the human Smad7 protein may be truncated at the C-terminal, or truncated at the N-terminal. In some embodiments, the truncated human Smad7 protein may include about 50% of the full-length Smad7 sequence, or may include about 13% of the full-length Smad7 sequence. In some embodiments, the human Smad7 protein may comprise or consist of amino acids 2-258, amino acids 204-258, or amino acids 259-426 of the human Smad7 protein. In some embodiments, the protein molecule may have one or more biological activities selected from the group consisting of reducing or eliminating phosphorylation of Smad2, reducing or eliminating nuclear translocation of the NF-κB p50 subunit, increasing cell proliferation, reducing apoptosis, reducing radiation-induced DNA damage, reducing inflammation, reducing angiogenesis, promoting healing in oral mucositis, promoting wound healing, and treating auto-immune disease. In some embodiments, any of the foregoing may further comprise a protein transduction domain, such as Tat. In some embodiments, any of the foregoing may also further comprise one or more of an epitope tag or a purification tag, such as V5, glutathione-S-transferase or 6-histidine (SEQ ID NO: 40). In some embodiments, a pharmaceutical composition comprising any of the foregoing, a protein molecule, and one or more pharmaceutically acceptable excipients is provided.

In another aspect, a method is provided for treating or preventing an inflammatory condition in a subject comprising providing to the subject a therapeutically effective amount of the pharmaceutical composition described above. In some embodiments, the inflammatory condition may be one or more of a chronic wound, skin inflammation, psoriasis, or an autoimmune disease. In some embodiments, the composition may reduce inflammation through inhibition of TGF-β and NF-κB signaling.

In another aspect, a method is provided for preventing or treating a disease or disorder in a subject comprising one or more of increasing one or more of cell proliferation or cell migration, or preventing one or more of apoptosis or DNA damage in the subject comprising providing to the subject a therapeutically effective amount of the pharmaceutical composition as described above, wherein one or more of increasing one or more of cell proliferation or cell migration, or preventing one or more of apoptosis or DNA damage is useful in preventing or treating the disease or disorder. In some embodiments, the disease or disorder may include one or more of chronic wounds, acute wounds, or mucositis. In some embodiments, the chronic wounds may include one or more of diabetic ulcers, pressure ulcers, venous ulcers, or oral ulcers, the acute wounds may include one or more of trauma-induced wounds, surgical wounds, or scarring, the mucositis may include one or more of radiation-induced mucositis or chemotherapy-induced mucositis and the mucositis may include one or more of oral mucositis or gut mucositis.

It is contemplated that any method or composition described herein can be implemented with respect to any other method or composition described herein The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present technology will become apparent from the following detailed description. It should be understood, however, that the detailed description and the specific examples, while indicating specific embodiments of the present technology, are given by way of illustration only, since various changes and modifications within the spirit and scope of the present technology will become apparent to those skilled in the art from this detailed description.

BRIEF DESCRIPTION OF THE DRAWINGS

The following drawings form part of the present specification and are included to further demonstrate certain embodiments of the present technology. The embodiments may be better understood by reference to one or more of these drawings in combination with the detailed description of specific embodiments presented herein.

FIG. 1A provides an illustrative embodiment of H&E staining in non-irradiated and irradiated (day 9 after initiation of radiation) wild-type (WT) and K5.Smad7 tongues. The vertical lines in the images of tongues from WT mice highlight the ulcer boundary and dotted lines in the images indicate the epithelial-stromal boundary (scale bar, 50 μm). FIG. 1B provides a graphical representation of the quantification of sizes of tongue ulcers (mean±s.e.m); n=8 for WT mice and n=7 for K5.Smad7 mice in 8 Gy×3 radiation; n=5 for WT mice and n=4 for K5.Smad7 mice in 18-Gy radiation; n=5 per group for WT and K5.Smad7 mice in 22-Gy radiation. FIG. 1C provides an illustrative embodiment of human ventricular posterior of the tongue (top) and radiation-induced tongue mucositis (bottom) visualized using H&E (left) and CD45 staining (right). The solid line indicates the ulcer boundary, and dotted lines indicate the basement membrane (scale bar, 25 μm). FIG. 1D provides an illustrative embodiment of immunostaining of CD45, proliferating cell nuclear antigen (PCNA), and TUNEL assay in irradiated sections adjacent to an ulcer from WT mice and in damaged areas from K5.Smad7 mice (PI, propidium iodide). Dotted lines indicate the basement membrane (scale bar, 25 µm). FIGS. 1E-1G provide graphical representations of the quantification of staining in FIG. 1D (n=3 or 4 per group). Data are expressed as mean±s.e.m (FIG. 1B) or mean±s.d (FIGS. 1E-1G), and two-tail Student t-test is used to calculate P values. *P<0.05, P<0.01, *P<0.001, NS, no significance determined by two-tailed Student's t-test. Dotted lines in (FIG. 1A), (FIG. 1C) and (FIG. 1D) highlight the basement membrane. Scale bar: 50 µm for all panels in (FIG. 1A) and (FIG. 1C), 25 µm for all panels in (FIG. 1D).

FIG. 2A provides an illustrative embodiment of immune-staining of NF-κB p50, TGF-β1 and pSmad2. Irradiated tongue sections of wild-type (WT) were adjacent to ulcer and sections of K5.Smad7 were from the damaged area. Human samples were from non-irradiated oral mucosa and radiation-induced mucositis. Dotted lines delineate epithelial-stromal boundary. Scale bar, 25 µm for all panels. FIG. 2B provides a graphical representation of the quantification of immunostaining of NF-κB p50 and pSmad2 shown in (FIG. 2A). FIG. 2C provides an illustrative embodiment of qRT-PCR of TGF-β1 (normalized by Keratin 5, n=6 per group for day 0, n=4 for day 7 and day 9, and n=7 for day 10). FIG. 2D provides a graphical representation of the quantification of human oral keratinocyte migration (see images in FIG. 8). Scrambled, scrambled siRNA; n=3 per group. FIG. 2E provides an illustrative embodiment of a western analysis of knockdown efficiency of siSmad7-1 and siSmad7-2 for Smad7 and for Rac1, 72 hours after Smad7 knockdown. M, molecular markers. FIG. 2F provides an illustrative embodiment of western analysis of total and activated (GTP-bound) Rac1 protein. M: molecular markers. FIG. 2G provides a graphical representation of the quantification of the effect of Rac1 knockdown on Smad7-mediated keratinocyte migration (see knockdown efficiency in FIG. 9A and images in FIG. 9D). n=3 per group. Data are presented as mean±s.d. and two-tail Student's t-test was used to calculate P values for (FIGS. 2B-2D) and (FIG. 2G). *P<0.05, P<0.01, *P<0.001. NS, no significance.

FIG. 3A provides a graphical representation of the quantification of Rac1 mRNA in wild-type (WT) and Smad7 transgenic keratinocytes. n=4 per group. FIG. 3B provides an illustrative embodiment of western analysis of GTP-Rac1 and total Rac1 in WT and Smad7 keratinocytes. Smad7 protein levels in WT and Smad7 keratinocytes were determined by reprobing the tubulin western blot with an antibody to Smad7 (see an additional western blot and quantification in FIGS. 10A-B). FIG. 3C provides an illustrative embodiment of western analysis of Rac1 protein level after knocking down individual Smad2, Smad3 or Smad4 in human keratinocytes (see FIG. 10C-10E for Smad knockdown efficiencies). FIG. 3D provides an illustrative embodiment of a ChIP assay for Smad-2, -3, -4, and -7 binding to the −1.5 Kb SBE site of the Rac1 promoter in WT and Smad7 transgenic keratinocytes. FIG. 3E provides a graphical representation of the quantification of Rac1 luciferase reporter assay in mouse keratinocytes. Scrambled: scrambled siRNA. n=6. FIG. 3F provides a graphical representation of the quantification of the activities of Rac1 luciferase reporter containing SBE or mutant (mut) SBE in WT or Smad7 transgenic keratinocytes. n=6. FIG. 3G provides an illustrative embodiment of images of ChIP assays of CtBP1 binding to the SBE-1.5 Kb site of the Rac1 promoter in WT or K5.Smad7 keratinocytes. FIG. 3H provides a graphical representation of ChIP-qPCR quantification of CtBP1 binding to the SBE shown in FIG. 3G in WT and Smad7 transgenic keratinocytes. n=4. Data are presented as mean±s.d. and two-tail Student's t-test is used to calculate P values for FIGS. 3A, 3E, 3F and 3H. *P<0.05, P<0.01, *P<0.001.

FIG. 4A provides an illustrative embodiment of western analysis of Rac1 protein after knockdown of CtBP1 in human oral keratinocytes. FIG. 4B provides a graphical representation of the quantification of SBE-containing Rac1 luc reporter activity. n=6. FIG. 4C provides a graphical representation of the quantification of the effect of CtBP1 knockdown on human oral keratinocyte migration. n=3 per group. FIG. 4D provides an illustrative embodiment of immunostaining of CtBP1. Irradiated sections were adjacent to the ulcer (WT) or the damaged area (K5.Smad7). Dotted lines denote the basement membrane. Scale bar, 50 µm for all panels. FIG. 4E provides an illustrative embodiment of immunostaining of CtBP1 in non-irradiated oral mucosa and radiation-induced oral mucositis in human specimens. Dotted lines denote the basement membrane. Scale bar, 50 µm for both panels. FIG. 4F provides a graphical representation of the quantification of CtBP1 nuclear positive cells in FIGS. 4D-E. n=3 or 4 per group. FIG. 4G provides a graphical representation of the quantification of qRT-PCR for CtBP1 (normalized with Keratin K5). n=6 per group for day 0, n=4 for day 7 and day 9, and n=7 for day 10. Data are presented as mean±s.d. and two-tail Student's t-test is used to calculate P values for FIGS. 4B, 4C, 4F and 4G. *P<0.05, P<0.01, *P<0.001.

FIG. 5A provides a graphical representation of the quantification of oral mucositis ulcer sizes on day 9 after initiation of 8 Gy×3 radiation. Vehicle=saline or 50% glycerol/PBS. FIG. 5B provides an illustrative embodiment of pathological alterations on day 9 of initiation of 8 Gy×3 radiation. Vehicle=saline or 50% glycerol/PBS. Scale bar, 50 µm for H&E panels and 25 µm for remaining panels. Dotted lines delineate epithelial-stromal boundary; the solid line highlights the ulcer boundary. FIGS. 5C, 5D, 5E, 5F, and 5G provide a graphical representation of the quantification of immunostaining shown in FIG. 5B. n=3 or 4 per group. Data are presented as mean±s.e.m (FIG. 5A) or mean±s.d. (FIGS. 5C-5G) and two-tail Student's t-test is used to calculate P values. *P<0.05, P<0.01, *P<0.001. NS, no significance.

FIG. 6A provides a graphical representation of the quantification of ulcer sizes measured on day 10 after initiation of 8 Gy×3 radiation. Glycerol=50% glycerol/PBS. FIG. 6B provides an illustrative embodiment of H&E staining of oral mucosa. Upper panels: open ulcer in Palifermin treated but not Tat-Smad7 treated mucosa. Lower panels: comparison of epithelial thickness between Palifermin treated and Tat-Smad7 treated mucosa. Dotted lines delineate the basement membrane. The vertical line highlights the ulcer boundary. Scale bar, 50 µm for all panels. FIG. 6C provides an illustrative embodiment of immune-staining of Tat-Smad7 treatment in 20 Gy-induced oral mucositis after ulcers healed. V5 immunostaining visualizes Tat-Smad7 in oral epithelia (sections are away from the damaged regions). K14 immunostaining was used as counterstain. Dotted lines delineate basement membrane. Scale bar, 25 µm for all panels. FIG. 6D provides an illustrative embodiment of Rac1 western analysis of Tat- Smad7 treated mouse tongues, day 10 after initiation of 8 Gy×3 radiation. FIG. 6E provides an illustrative embodiment of Rac1 western analysis on Tat-Smad7 treated normal human oral keratinocytes 48 hours after treatment. FIG. 6F provides an illustrative embodiment of the effect of Tat-Smad7 treatment on oral human keratinocyte migration (NOK-SI, see images in FIG. 13A). n=4 per group. FIG. 6G provides a graphical representation of the quantification of survival curves of NOK-SI keratinocytes and SCC lines (Cal27 and MSK921) with or without Tat-Smad7 treatment. n=4 per group for each radiation dose. Data are presented as mean±s.e.m (FIG. 6A) or mean±s.d. (FIGS. 6F, 6G) and two-tail Student's t-test is used to calculate P values. *P<0.05, P<0.01, *P<0.001. NS, no significance.

FIG. 7A provides an illustrative embodiment of Smad7 western blots: undetectable in non-irradiated wild-type (WT) tongue and barely detectable after radiation. K5.Smad7 tongues have comparable Smad7 protein levels before and after radiation. M: molecular marker. FIG. 7B provides an illustrative embodiment of Smad7 immunostaining. Note that nuclei in some irradiated epithelial cells are hypertrophic. Dotted lines delineate epithelial-stromal boundary. FIG. 7C provides a graphical representation of the quantification of reduced incidence of oral mucositis-induced morbidity in K5.Smad7 mice. Fisher's exact test is used to calculate the p value. **P=0.007. FIG. 7D provides an illustrative embodiment of immune-staining of K5.Smad7 tongue showing reduced infiltration of neutrophils (Ly-6G), macrophages (BM8) and activated T cells (CD4) compared to WT oral mucositis. Dotted lines delineate epithelial-stromal boundary. FIG. 7E provides an illustrative embodiment of immune-staining showing no significant difference in pSmad1/5/8-nuclear positive cells (green) between WT and K5.Smad7 oral mucosa before or after radiation. Keratin (K14) immunostaining (red) highlights the epithelial compartment. Note that nuclei of irradiated epithelial cells are hypertrophic. The scale bar is 50 μm for all panels.

FIGS. 8A and 8B provide an illustrative embodiment of representative images of cell migration. Pairs of dotted lines delineate the scratch wound. Quantification of cell migration and efficiency of Smad7 knockdown are presented in FIG. 2D and FIG. 2E (above). Scrambled, scrambled siRNA. FIG. 8C provides a graphical representation of the quantification of cell migration after TGF-β1 knockdown from 3 separate experiments. FIG. 8D provides a graphical representation of qRT-PCR showing TGF-β1 knockdown efficiency. Data are presented as mean±s.d. and two-tail Student's t-test was used to calculate P values. *P<0.05, **P<0.01. NS, no significance.

FIG. 9A provides an illustrative embodiment of western blot analysis for Rac1 48 hours after Rac1 siRNA (siRac1-1, siRac1-2) transfection. Control, scrambled siRNA. FIG. 9B provides a graphical representation of the percentage of BrdU labeled cells in WT and Smad7 cultured cells in BrdU incorporation assay with or without Rac1 knockdown. Data from 3 separate experiments were presented as mean±s.d. ***P<0.001. FIG. 9C provides an illustrative embodiment of representative immunofluorescence of BrdU positive cells presented in (FIG. 9B). An antibody against keratin 14 (K14, red) was used for counterstain. FIG. 9D provides an illustrative embodiment of in vitro cell migration assay for Smad7 transgenic and WT keratinocytes after Rac1 knockdown. Pairs of dotted lines delineate the scratch wound. Quantification of cell migration is presented in FIG. 2G.

FIG. 10A provides an illustrative embodiment of western blot analysis for GTP-Rac1 and total Rac1 in Smad7 transgenic keratinocytes. Additional samples are shown in FIG. 3B. M, molecular marker. FIG. 10B provides a graphical representation of the quantification of GTP-Rac1, total Rac1 and Smad7 in WT and K5.Smad7 keratinocytes shown in FIG. 10A and in FIG. 3B. The protein level in WT keratinocytes of each blot was normalized as "1". Data is presented as mean±s.d. and two-tail Student's t-test was used to calculate P values. P<0.01, *P<0.001. FIGS. 10C and 10D provide an illustrative embodiment of western blot analysis for Smad2, Smad3, and Smad4 knockdown in NOK-SI cells. Their effects on Rac1 expression are shown in FIG. 3C. M, molecular marker. GAPDH, internal protein control by reprobing same blot. FIG. 10F provides an illustrative embodiment showing CtBP1 knockdown promotes NOK-SI cell migration. Pairs of dotted lines delineate the scratch wound. Quantification of cell migration and efficiency of CtBP1 knockdown are shown in FIG. 4A and FIG. 4C.

FIG. 11A shows an illustrative embodiment of a schematic representation of Tat-Smad7 protein. FIG. 11A discloses SEQ ID NOS 49 and 87, respectively, in order of appearance. FIG. 11B provides an illustrative embodiment of a western blot of purified Tat-Smad7 protein. FIG. 11C provides an illustrative embodiment of immune-staining of Tat-Smad7 protein transduction in keratinocytes. Left and middle panels: Tat-Smad7 staining (green) using a V5 antibody, counterstained with a K14 antibody (red). Cells showed Tat-Smad7 in the nucleus 5 min after transduction and in both nucleus and cytoplasm 12 hours after transduction. Right panels: Tat-Smad7 abrogated Smad2 phosphorylation (pSmad2, green). V5 (red) counterstain visualizes Tat-Smad7 transduced cells. FIG. 11D provides an illustrative embodiment of immune-staining showing that V5 antibody staining detects Tat-Smad7 transduction in buccal mucosa 12 hours after Tat-Smad7 topical application. A K14 antibody was used for counterstain. Scale bar, 50 μm for both panels. FIG. 11E provides an illustrative embodiment of a western blot of purified Tat-Cre protein with the same Tat and V5 tags shown in FIG. 11A. FIG. 11F provides an illustrative embodiment of an agarose gel showing activity of Tat-Cre: Tat-Cre cuts out a 1,460 bp floxed fragment from the 7,650 bp vector pLL3.7. FIG. 11G provides a graphical representation showing Tat-Smad7 protein preventive treatment reduced 20 Gy radiation-induced oral ulcers. Data are expressed as mean±s.e.m. Two-tail Student's t-test is used to calculate P values. *P<0.05, ***P<0.001.

FIG. 12A provides a graphical representation of the quantification of reduced ulcer size in Tat-Smad7 (0.8 μg daily, day 6 to day 9) treated oral mucosa. Samples were harvested on day 10. n=8 per group. FIG. 12B provides an illustrative embodiment of immunostaining of molecular markers for samples from FIG. 12A. Scale bar, 50 μm for the top two panels and 25 µm for other panels. Propidium iodide (PI) and K14 were used as counterstain. FIGS. 12C-G provide graphical representation of the quantifications of immunostaining shown in FIG. 12C. 3-4 samples were used. FIG. 12H provides a graphical representation quantification of the Luciferase assay. Tat-Smad7 treatment increased the activity of the Rac1 promoter with SBE but not the mutant SBE in mouse keratinocytes. FIG. 12I provides an illustrative embodiment of a ChIP assay for CtBP1 binding to the SBE of mouse Rac1 promoter in Tat-Smad7 treated mouse keratinocytes. Data are expressed as mean±s.e.m (a) or mean±s.d (c-h) and two-tail Student's t-test is used to calculate P values. *P<0.05, P<0.01, *P<0.001. NS, no significance.

FIG. 13A provides an illustrative embodiment showing Tat-Smad7 accelerates NOK-SI cell migration. Quantification from four separate experiments is shown in FIG. 6F (above). Pairs of dotted lines delineate initial wounds. FIG. 13B provides an illustrative embodiment of immunostaining of Tat-Smad7 treatment in NOK-SI cells showing attenuated radiation-induced pSmad2 and NF-κB p50 nuclear localization. FIG. 13C provides an illustrative embodiment showing V5 staining of MSK921 cells 2 hours after Tat-Smad7 treatment. K14 staining was used as counterstain. FIG. 13D provides an illustrative embodiment of a Rac1 western analysis in MSK921 60 hours after Tat-Smad7 treatment. M, molecular marker. FIG. 13E provides a graphical representation of quantification of MSK921 cell migration from 3 separate experiments. FIG. 13F provides an illustrative embodiment showing a representative MSK921 cell migration assay treated with Tat-Smad7 and PBS. Pairs of solid lines delineate initial wounds. Dotted lines highlight the forefront of migrated cells. FIG. 13G provides a graphical representation of quantification of Cal27 cell migration from 3 separate experiments. FIG. 13H provides an illustrative embodiment showing representative images for FIG. 13G. Pairs of solid lines delineate initial wounds. Dotted lines highlight the forefront of migrated cells. Data are expressed as mean±s.d. and the two-tail Student's t-test is used to calculate P values. NS, no significance.

FIG. 14A shows an illustrative schematic of how radiation activates NF-κB, increases TGF-31 and CtBP1. NF-κB and TG1 induce inflammation. TG1 induces apoptosis, growth arrest and activates Smad-2, -3 and -4, which recruit CtBP1 to the Rac1 promoter to repress Rac1 transcription, leading to blunted re-epithelialization. FIG. 14B shows an illustrative schematic of how Smad7 blocks NF-κB and TGF-β1-induced inflammation and blocks TGF-β1-induced apoptosis and growth arrest. Smad7 relieves Rac1 transcriptional repression by either preventing TGF-β1-mediated Smad activation (phosphorylation) or competing with signaling Smads/CtBP1 transcriptional repression complex in binding to the Rac1 promoter. Increased Rac1 induced by Smad7 contributes to keratinocyte migration during re-epithelialization.

DETAILED DESCRIPTION

Figure 1:
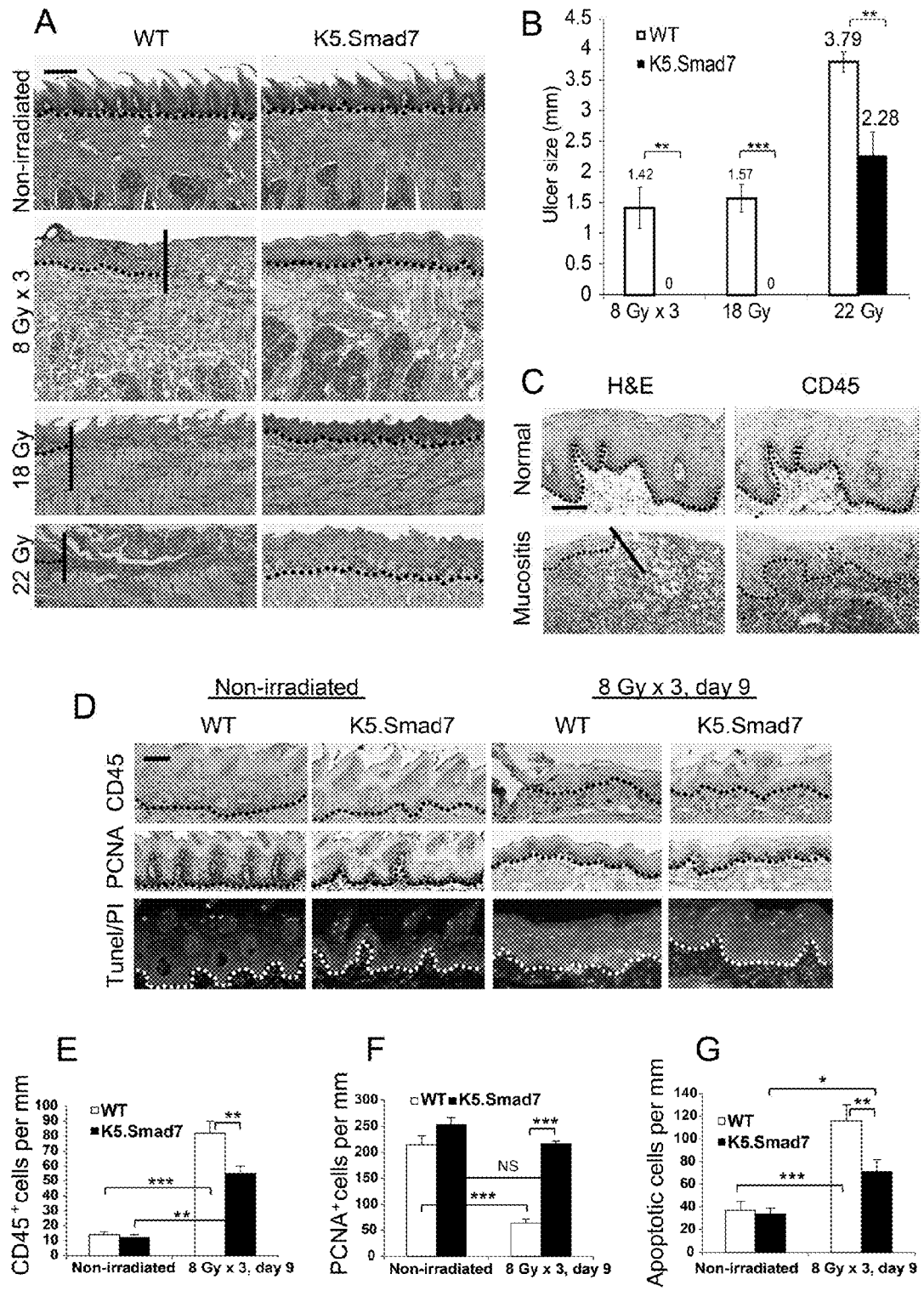
FIGS. 1A-G provide an illustrative embodiment of data showing that K5.Smad7 mice were resistant to radiation-induced oral mucositis.

As further described herein, the disclosure provides Smad7 proteins and biologically active fragments and derivatives thereof, nucleic acids encoding such proteins, vectors including such nucleic acids, and cells encompassing the vectors, nucleic acids, and/or proteins all for use in formulating medicaments and for treating and/or preventing one or more diseases or disorders. Also provided are methods for making and for screening Smad7 proteins and biologically active fragments and derivatives thereof useful for treating and/or preventing one or more diseases or disorders. Also provided are methods for predicting and/or evaluating a response to treatment using one or more markers associated with exposure to Smad7. Such markers may include, but are not limited to, Rac1 for cell migration, NF-κB for inflammation, and TGF-β for growth arrest and inflammation.

Smad7 treatable diseases and disorders may include those including one or more of reduced cell proliferation, reduced cell migration, increased cell death, excessive inflammation, and/or DNA damage. Smad7 treatable diseases and disorders may include those where treatment with a Smad7 protein and biologically active fragments and derivatives thereof that have one or more activities including but not limited to increasing proliferation, reducing or inhibiting cell death, reducing excessive inflammation, preventing DNA damage, and/or increasing cell migration. Such diseases and/or disorders may include but are not limited to acute (e.g., through surgery, combat, trauma) and chronic wounds (e.g., ulcers, such as diabetic, pressure, venous), scarring, fibrosis, and aberrant healing, mucositis (e.g., oral and/or gastro-intestinal), stomatitis, proctitis, autoimmune disease (e.g., psoriasis, arthritis), and cancer.

It is critical for oral mucositis prevention and treatment to overcome epithelial ablation due to massive apoptosis and blunted keratinocyte proliferation. The proliferative and anti-apoptotic effects of Smad7 are more obvious in oral mucositis than in normal oral mucosa, when TGF-β1, a potent growth inhibitor and apoptosis inducer for epithelial cells, was increased.

Although not wishing to be bound by theory, it is believed that increased Rac1 activation is largely responsible for Smad7-mediated keratinocyte migration in wound closure. This finding was unexpected, given the documented role of TGF-β signaling in Rho/Rac activation in cancer cells via a Smad-independent mechanism (Dernyck et al., *Nature* 415: 577-584, 2003).

It is believed that during oral mucositis, Smad-dependent Rac1 repression overcomes Smad-independent Rac1 activation (if any) due to increased Smad signaling (evidenced by increased pSmad2) and Smad transcriptional co-repressor CtBP1. When this repression is abrogated by Smad7, it permits Rac1 activation-mediated keratinocyte migration. However, in oral cancer cells, signaling Smads are lost or inactivated, or other mechanisms independently activate Rac1. As a result, Smad7-mediated abrogation of Rac1 repression would no longer occur.

Although Rac1 activation also contributed to keratinocyte proliferation, knocking down Rac1 only partially attenuated the proliferative effect of Smad7. Therefore, Rac1's contribution to proliferation appears to be limited, and blocking TGF-β1-induced growth arrest is also needed to overcome radiation-induced growth inhibitory effects.

Dampening excessive inflammation creates a microenvironment for oral mucositis healing. The antagonistic effect of Smad7 on both TGF-β and NF-κB signaling makes Smad7 a more efficient anti-inflammatory molecule than other agents targeting only NF-κB. Because inflammatory cells produce cytokines that further activate TGF-β and NF-κB, reduced TGF-β and NF-κB signaling, found in K5.Smad7 or Tat-Smad7 treated oral mucosa after radiation, reflects the direct antagonistic effect of Smad7 on these two pathways and the consequence of reduced inflammatory cytokines from infiltrated leukocytes. However, Smad7 did not reduce NF-κB or TGF-β signaling below their normal physiological conditions. This incomplete blockade of NF-κB or TGF-β signaling may be beneficial to oral mucositis healing, as a complete loss of either pathway could induce excessive inflammation.

The primary obstacle to using growth factors to treat oral mucositis in cancer patients is the potential risk of promoting cancer cell growth. The majority of human oral cancers lose TGF-β signaling in tumor epithelial cells. Thus, anti-Smad-associated cell proliferation and migration by Smad7 would not be effective in cancer cells. In tumors with intact TGF-β signaling, activation of other oncogenic pathways could override TGF-β-induced tumor suppressive effects. These two scenarios could explain why there was no observation of Smad7 increasing proliferation and migration in oral cancer cells with mutant or intact TGF-β signaling components.

Additionally, TGF-β signaling promotes tumor invasion mainly through Smad-independent mechanisms after loss of TGF-β-induced tumor suppression. Thus, blocking TGF-β signaling by Smad7 in cancer cells could abrogate TGF-β-mediated tumor promotion effects, which behaves similarly to TGF-β inhibitors currently being used in clinical trials for advanced cancers. Further, the potent anti-inflammatory effect of Smad7 may reduce the risk of tumor progression. Therefore, long-term Smad7 application may also be helpful in cancer treatment.

Spontaneous tumor formation in K5.Smad7 mice has not been observed. Because Smad7 is not a secreted protein, local and short-term Smad7 protein delivery in oral mucositis treatment should have few systemic effects. In bone marrow transplant patients, whose oral epithelia do not contain cancer cells, Smad7 topical application may be suitable for both prevention and treatment of oral mucositis.

Figure 14:
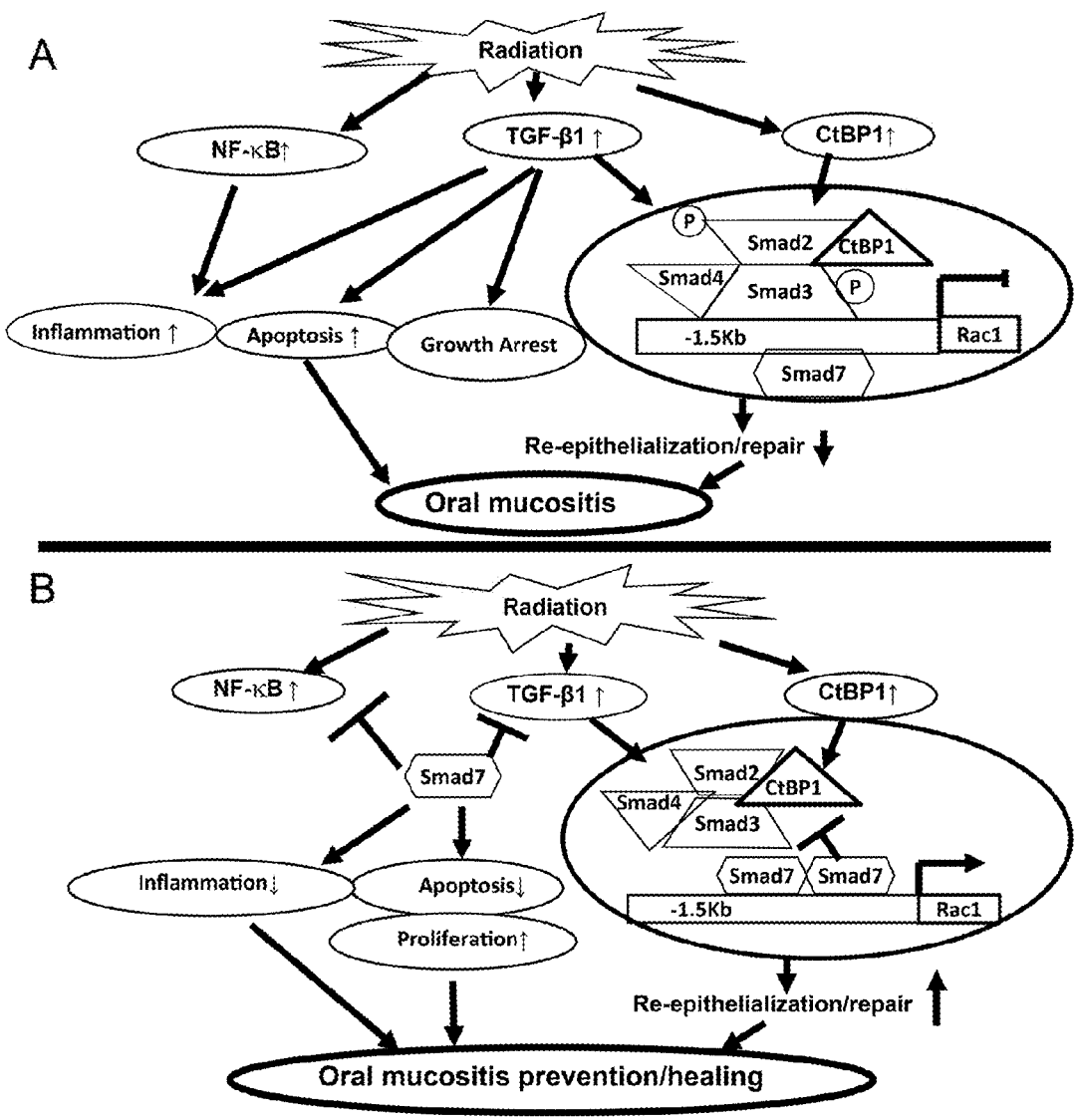
FIGS. 14A-B show an illustrative schematic of a summary of potential mechanisms of Smad7-mediated protection and healing of oral mucositis.

Although not wishing to be bound by any theory, Smad7-mediated oral mucositis healing appears to be a result of targeting multiple pathogenic processes mediated by one or more molecules (see, e.g., FIGS. 14A-B). It is believed that one or more of these molecules (e.g., TGF-β, NF-κB, CtBP1, Rac1) may also be helpful as predictive and therapeutic responsive markers of oral mucositis in patients.

A. Nucleic Acids, Vectors and Host Cells

The present disclosure also provides, in another embodiment, genes encoding Smad7. In addition to the wild-type SMAD7 gene (SEQ ID NO: 22), which encodes the wild-type Smad7 protein (SEQ ID NO: 12), as well as various codon-optimized versions (SEQ ID NOs: 9, 21, 23, 24, 26, 28, 30, 32-34, 36, 38, and 39), it should be clear that the present technology is not limited to the specific nucleic acids disclosed herein. As discussed below, a "Smad7 gene" may contain a variety of different bases and yet still produce a corresponding polypeptide that is functionally indistinguishable from, and in some cases structurally identical to, the human gene disclosed herein.

1. Nucleic Acids Encoding Smad7

Nucleic acids according to the present technology may represent an entire Smad7 gene, a truncated portion, and/or a fragment of Smad7 that expresses a polypeptide with one or more activity associated with Smad7 such as but not limited to increasing proliferation, reducing or inhibiting cell death, reducing excessive inflammation, preventing DNA damage, and/or increasing cell migration, as well as treating or preventing one or more disease or disorders in which such treatment would be helpful as further discussed herein. Such activities can be assessed using one or more assays including, but not limited to, the ability to block phosphorylation of Smad2 and/or nuclear translocation of the NF-κB p50 subunit, increase cell proliferation, reduce apoptosis and/or radiation-induced DNA damage, reduce inflammation and/or angiogenesis, promote healing in oral mucositis, surgical wounds, diabetes wounds, and/or wounds associated with chronic inflammation in mice. The nucleic acid may be derived from genomic DNA, i.e., cloned directly from the genome of a particular organism. In particular embodiments, however, the nucleic acid would comprise complementary DNA (cDNA). Also provided is a cDNA plus a natural intron or an intron derived from another gene; such engineered molecules are sometime referred to as "mini-genes." At a minimum, these and other nucleic acids of the present technology may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

As used in this application, the term "a nucleic acid encoding a Smad7" may refer to a nucleic acid molecule that has been isolated free of total cellular nucleic acid and/or may refer to a cDNA encoding a Smad7 polypeptide. As used herein, the term "isolated free of total cellular nucleic acid" means that the nucleic acid molecule is about or at least about 75% pure, 80% pure, 85% pure, 90% pure, 95% pure, 96% pure, 97% pure, 98% pure, 99% pure, or 100% pure of other cellular nucleic acid molecules as determined using standard biochemical techniques, such as but not limited to agarose gel electrophoresis. As used herein, the term "isolated free of total cellular protein" means that the protein molecule is about or at least about 75% pure, 80% pure, 85% pure, 90% pure, 95% pure, 96% pure, 97% pure, 98% pure, 99% pure, or 100% pure of other cellular nucleic acid molecules as determined using standard biochemical techniques, such as but not limited to a western blot. In certain embodiments, the present technology concerns a nucleic acid sequence essentially as set forth in, and/or including any one of SEQ ID NOs: 9, 21, 23, 24, 26, 28, 30, 32-34, 36, 38, and 39.

An isolated nucleic acid molecule may be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (e.g., production of Smad7 protein in non-human expression systems).

The term "essentially as set forth in one or more nucleic acid sequence (e.g., SEQ ID NOs: 9, 21, 23, 24, 26, 28, 30, 32-34, 36, 38, and 39" means that the nucleic acid sequence substantially corresponds to at least a portion, and in some cases the entirety, of the one or more nucleic acid sequence (e.g., SEQ ID NOs: 9, 21, 23, 24, 26, 28, 30, 32-34, 36, 38, and 39). In some embodiments, sequences that substantially correspond to at least a portion of a nucleic acid sequence, may correspond to about, or at least about 50 nucleic acids, 75 nucleic acids, 150 nucleic acids, 200 nucleic acids, 250 nucleic acids, 300 nucleic acids, 350 nucleic acids, 400 nucleic acids, 450 nucleic acids, 500 nucleic acids, 550 nucleic acids, 600 nucleic acids, 650 nucleic acids, 700 nucleic acids, 750 nucleic acids, 800 nucleic acids, 900 nucleic acids, 1000 nucleic acids, 1100 nucleic acids, 1200 nucleic acids, or 1250 nucleic acids of one or more of the sequences described herein. In some embodiments, sequences that substantially correspond to at least a portion of a nucleic acid sequence, may correspond to about a range of about 50-1250 nucleic acids, 75-1250 nucleic acids, 150-1250 nucleic acids, 200-1250 nucleic acids, 250-1250 nucleic acids, 300-1250 nucleic acids, 350-1250 nucleic acids, 400-1250 nucleic acids, 450-1250 nucleic acids, 500-1250 nucleic acids, 550-1250 nucleic acids, 600-1250 nucleic acids, 650-1250 nucleic acids, 700-1250 nucleic acids, 750-1250 nucleic acids, 800-1250 nucleic acids, 900-1250 nucleic acids, 1000-1250 nucleic acids, 1100-1250 nucleic acids, 1200-1250 nucleic acids, at least about 50-75 nucleic acids, 75-150 nucleic acids, 75-200 nucleic acids, 75-250 nucleic acids, 75-300 nucleic acids, 75-350 nucleic acids, 75-400 nucleic acids, 75-450 nucleic acids, 75-500 nucleic acids, 75-550 nucleic acids, 75-600 nucleic acids, 75-650 nucleic acids, 75-700 nucleic acids, 75-750 nucleic acids, 75-800 nucleic acids, 75-900 nucleic acids, 75-1000 nucleic acids, 75-1100 nucleic acids, 75-1200 nucleic acids, or 75-1250 nucleic acids or 1250 nucleic acids of one or more of the sequences described herein.

In some embodiments, sequences that substantially correspond to at least a portion of a nucleic acid sequence include identical sequences to that portion of the nucleic acid sequence. In some embodiments, sequences that substantially correspond to at least a portion of a nucleic acid sequence or the entirety of a nucleic acid sequence may include one or more functionally equivalent codons. The term "functionally equivalent codon" is used herein to refer to one or more codons that encode the same amino acid, such as the six codons for arginine or serine, and in some embodiments refers to codons that encode biologically equivalent amino acids, as discussed in the following pages. The term "biologically equivalent" amino acid is used herein to refer to one or more amino acids that when changed from the amino acid present in the amino acid sequence of human Smad7 wild-type protein, do not change one or more (or in some embodiments any) of the biological activities of Smad7 described herein, such as but not limited to, increasing proliferation, reducing or inhibiting cell death, reducing excessive inflammation, preventing DNA damage, and/or increasing cell migration, as well as treating or preventing one or more disease or disorders in which such treatment would be helpful as further discussed herein.

In some embodiments, allowing for the degeneracy of the genetic code, sequences that have about or at least about 60%, 70%, 80%, 90%, 91%, 92%, 93%, 94%, 95%, 96%, 97%, 98%, and/or 99% of nucleotides that are identical to the nucleotides of any one of the codon-optimized nucleic acid sequences (e.g., SEQ ID NOs: 9, 21, 23, 24, 26, 28, 30, 32-34, 36, 38, and 39) may be considered substantially corresponding nucleic acid sequences. Sequences that are essentially the same as those set forth in any one of the nucleic acid sequences (e.g., SEQ ID NOs: 9, 21, 23, 24, 26, 28, 30, 32-34, 36, 38, and 39) also may be functionally defined as sequences that are capable of hybridizing to a nucleic acid segment containing the complement of SEQ ID NOs: 9, 21, 23, 24, 26, 28, 30, 32-34, 36, 38, and 39 under various standard conditions.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

To determine the percent homology of two amino acid sequences or of two nucleic acids, the sequences are aligned for optimal comparison purposes (e.g., gaps are introduced in the sequence of a first amino acid or nucleic acid sequence for optimal alignment with a second amino acid or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (% identity=# of identical positions/total # of positions (e.g., overlapping positions)×100). In some embodiments the two sequences are the same length.

To determine percent homology between two sequences, the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877 can be used. Such an algorithm is incorporated into the NBLAST and XBLAST programs of Altschul et al. (1990) *J. Mol Biol.* 215:403-410. BLAST nucleotide searches is performed with the NBLAST program, score=100, wordlength=12 to obtain nucleotide sequences homologous to a nucleic acid molecules described or disclose herein. BLAST protein searches is performed with the XBLAST program, score=50, wordlength=3. To obtain gapped alignments for comparison purposes, Gapped BLAST may be utilized as described in Altschul et al. (1997) *Nucleic Acids Res.* 25:3389-3402. When utilizing BLAST and Gapped BLAST programs, the default parameters of the respective programs (for example, XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, for example, 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, for example, 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. In certain instances conservative amino acid substitutions are utilized. Illustrative conservative substitution among amino acids are within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al. (1992), *Proc. Natl Acad. Sci. USA,* 89:10915-10919). The BLOSUM62 substitution frequencies can be used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The DNA segments of the present technology include those encoding biologically functional equivalent Smad7 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described elsewhere.

As described in greater detail below, the Smad7 nucleic acid sequence has been optimized for expression in alternative host organisms (e.g., non-human). Although as described above, the genetic code is degenerate, so frequently one amino acid may be coded for by two or more nucleotide codons. Thus, multiple nucleic acid sequences may encode one amino acid sequence. Although this creates identical proteins, the nucleic acids themselves are distinct, and can have distinct properties. As described herein, one aspect of the choice of codon usage can be (but is not limited to) the ability to express a protein in a non-native cells (e.g., a human protein in bacteria or yeast), or the level of expression in such cells. In order to obtain enough protein for purification, testing, and use in in vitro assays, in animal models, and eventually in clinical development, efficient protein expression in non-human systems is needed.

A series of 23 arginine amino acids in the human Smad7 protein sequence coded for by one or more of AGG (1.7% codon utilization; 9 residues), AGA (2.8% codon utilization; 2 residues), CGA (3.5% codon utilization; 4 residues), or CGG (5.4% codon utilization; 8 residues) has been identified, and it has been determined that in order to have efficient protein expression from non-human sources, such as, but not limited to, bacteria and/or yeast that one or more, and potentially all the arginine codons should be modified to CGT (20.6% codon utilization). Therefore, in some embodiments, the Smad7 codon-optimized nucleic acid sequence includes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or 23 codons for arginine that have been changed to CGT. In some embodiments, the Smad7 codon-optimized nucleic acid sequence includes one or more or all of the arginine codons at nucleic acid sequence positions 7-9, 43-45, 169-171, 403-405, 490-492, 526-528, 526-528, 823-825, 1057-1059, 16-18, 136-138, 199-201, 598-600, 31-33, 112-114, 316-318, 772-774, 940-942, 973-975, 1135-1137, 1276-1278, 637-639, or 814-816 be changed to CGT.

A series of 33 serine residues in the human Smad7 protein sequence coded for by TCC or TCG (9%) has been identified, and it has been determined that it may be beneficial to efficient protein expression and purification from non-human sources, such as, but not limited to, bacteria and/or yeast, that one or more, and potentially all the serine codons be modified to AGC (15% codon utilization). Therefore, in some embodiments, the Smad7 codon-optimized nucleic acid sequence includes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32 or 33 codons for serine that have been changed to (AGC). In some embodiments, the Smad7 codon-optimized nucleic acid sequence includes one or more or all of the serine codons at nucleic acid sequence positions 19-21, 46-48, 133-135, 292-294, 349-351, 451-453, 454-456, 460-462, 511-513, 514-516, 544-546, 595-597, 616-618, 634-636, 691-693, 694-696, 739-741, 745-747, 775-777, 847-849, 907-909, 919-921, 943-945, 1006-1008, 1009-1101, 1030-1032, 1054-1056, 1093-1095, 1126-1128, 1192-1194, 1237-1239, 1240-1242, 1273-1275. Of these, 23 codons (19-21, 292-294, 349-351, 451-453, 454-456, 460-462, 511-513, 514-516, 544-546, 616-618, 634-636, 691-693, 694-696, 739-741, 745-747, 775-777, 847-849, 907-909, 919-921, 1009-1101, 1030-1032, 1054-1056, 1093-1095) can be changed without introducing potential alternative open reading frames.

A series of 12 histidine residues in the human Smad7 protein sequence coded for by CAC (9.6% codon usage) has also been identified, and it has been determined that it may be beneficial to efficient protein expression and purification from non-human sources, such as but not limited to bacteria and/or yeast, that one or more, and potentially all the serine codons be modified to CAT (optionally to 12.6% usage). Therefore, in some embodiments, the Smad7 codon-optimized nucleic acid sequence includes at least 1, at least 2, at least 3, at least 4, at least 5, at least 6, at least 7, at least 8, at least 9, at least 10, at least 11, or 12 codons for histidine that have been changed to (CAT). In some embodiments, the Smad7 codon-optimized nucleic acid sequence includes one or more or all of the serine codons at nucleic acid sequence positions 142-144, 214-216, 217-219, 220-222, 226-228, 289-291, 589-591, 778-780, 1072-1074, 1147-1149. Of these, 4 codons (nucleotides 217-219, 220-222, 589-591, 778-780) can be changed without introducing potential alternative open reading frames.

In some embodiments, one or more codon-optimized nucleic acids may include one or more of at least one and any integer up to 22 of its arginine codons modified to CGT, at least one and any integer up to 28 of its serine codons (optionally that are able to be modified with introducing open reading frames) modified to AGC, or at least one and any integer up to 12 of its histidine codons (optionally that are able to be modified with introducing open reading frames) modified to CAT. In some embodiments, one or more codon-optimized nucleic acid may include at least one and any integer up to 22 of its arginine codons modified to CGT, at least one and any integer up to 28 of its serine codons (optionally that are able to be modified with introducing open reading frames) modified to AGC, and at least one and any integer up to 12 (optionally that are able to be modified with introducing open reading frames) of its histidine codons modified to CAT. In some embodiments, one or more codon-optimized nucleic acid may include 22 of its arginine codons modified to CGT, 28 of its serine codons (optionally that are able to be modified with introducing open reading frames) modified to AGC, and 12 of its histidine codons (optionally that are able to be modified with introducing open reading frames) modified to CAT. In some embodiments, one or more codon-optimized nucleic acid may also have a nucleotide substitution in the codon for Met216 (ATG), to form the codon for Leu216 (CTG).

In some embodiments, one or more codon-optimized nucleic acids may have about 65% to 75%, about 65% to 68%, about 68% to 75%, or about 68% to 71% homology to human Smad7 wild-type cDNA (SEQ ID NO: 22), which encodes the amino acid sequence as set forth in SEQ ID NO: 12. In some embodiments, one or more codon-optimized nucleic acid may have about 65%, 66%, 67%, 68%, 69%, 70%, 71%, 72%, 73%, 74%, or 75%, homology to human Smad7 wild-type cDNA (SEQ ID NO: 22). In some embodiments, one or more codon-optimized nucleic acid may also have a nucleotide substitution in the codon for Met216 (ATG), to form the codon for Leu216 (CTG).

A methionine codon (Met216; ATG) that has the potential for being perceived by translation machinery (e.g., such as but not limited bacteria or yeast) as an alternative open reading frame has been identified. Although not intending to be bound by theory, it is believed that the presence of the second potential open reading frame may decrease expression of the Smad7 protein. In some embodiments, one or more Smad7 nucleic acid sequences are modified at nucleotide position (646-648) to encode a human Smad7 protein where Met216 (ATG) is modified to Leu216 (CTG).

It has also been discovered that various truncated forms and fragments of Smad7 protein retain one or more of the activities of full-length human Smad7, such as, but not limited to, increasing proliferation, reducing or inhibiting cell death, reducing excessive inflammation, preventing DNA damage, and/or increasing cell migration, as well as treating or preventing one or more disease or disorders in which such treatment would be helpful as further discussed herein. Such activities can be assessed using one or more assays including, but not limited to, the ability to block phosphorylation of Smad2 and/or nuclear translocation of the NF-κB p50 subunit, increase cell proliferation, reduce apoptosis and/or radiation-induced DNA damage, reduce inflammation and/or angiogenesis, promote healing in oral mucositis, surgical wounds, diabetes wounds, and/or wounds associated with chronic inflammation in mice.

Further, in some embodiments, various truncated forms and fragments of Smad7 protein retain only a subset of the one or more of the activities of full-length human Smad7. For example, the C-terminal MH2 domain of Smad7 may primarily mediate the anti-inflammatory effect of Smad7. Smad7 peptides having this anti-inflammatory function may be sufficient and optionally an improvement for treating chronic inflammation associated conditions, such as but not limited to, oral mucositis, stomatitis, arthritis, and psoriasis, among others. The N-terminal MH1 domain may primarily mediate cell migration and/or blocking TGF-β-induced growth arrest and/or fibrotic response. Smad7 peptides having this cell migration and proliferation function may be sufficient, and optionally an improvement, for enhancing healing that is not associated with excessive inflammation. Types of wounds that might benefit from this form of treatment include, but are not limited to, surgical wounds, fibrotic scarring, and diabetes wounds, defective healing and/or scarring among others.

In some embodiments, nucleic acid molecules (optionally codon-optimized nucleic acid molecules as described above and herein) encode fragments or truncated forms of Smad7 protein (optionally including Leu216). In some embodiments, these fragments and/or truncated forms of Smad7 protein retain one or more or all of the activities of full-length human Smad7 protein. In some embodiments, such truncated nucleic acid sequences encode the N-terminal portion of the Smad7 protein. In some embodiments, such truncated nucleic acid sequences encode the C-terminal portion of the Smad7 protein. In some embodiments, such truncated nucleic acid sequences (nucleotide positions 4-774) encode amino acids 2-258 of the human Smad7 protein. In some embodiments, such truncated nucleic acid sequences (nucleotide positions 775-1278) encode amino acids 259-426 of the human Smad7 protein. In some embodiments, such fragments of the nucleic acid sequences (nucleotide positions 610-774) encode amino acids 204-258 of the human Smad7 protein.

The term "truncated" as used herein in reference to nucleic acid molecules refers to a molecule that contains nucleotide sequences encoding the natural N-terminus of a corresponding protein (with or without a cleaved leader sequence), but lacks one or more nucleotides starting from the C-terminus-encoding portion of the molecule, or a molecule that contains nucleotide sequences encoding the natural C-terminus of a corresponding protein (with or without a cleaved leader sequence), but lacks one or more nucleotides starting from the N-terminus-encoding portion of the molecule. In some embodiments, molecules lacking nucleotides encoding at least about 25, at least about 50, at least about 75, at least about 100, at least about 125, at least about 150, at least about 200, at least about 250, at least about 300, or at least about 350, or at least about 400 amino acids from one or the other terminus are specifically provided. Similarly, the term "truncated" may also be used in reference to protein molecules encoded by truncated nucleic acid molecules. In some embodiments, a "truncated" molecule is biologically active, having (or encoding a polypeptide having) one or more of the Smad7 activities described herein.

The term "fragment" as used herein in reference to nucleic acid molecules refers to a molecule containing contiguous residues of a full length sequence but lacking some 5' and/or 3' sequences of the full length sequence. In some embodiments, a "fragment" includes a portion of one or more of the full length sequences described herein. In some embodiments, the "fragment" does not include sequences encoding either the N-terminal or the C-terminal, but only internal fragments. In some embodiments, a "fragment" encodes a polypeptide that is biologically active, having one or more of the Smad7 activities described herein. In some embodiments, nucleic acid fragments may encode proteins having at least about 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150 amino acids. Similarly, "fragment" may also be used in reference to protein molecules encoded by Smad7 nucleic acid fragments.

The term "N-terminal portion" as used herein in refers to a fragment of a corresponding protein that contains the protein's N-terminus but lacks all sequences C-terminal to an internal residue.

The term "C-terminal portion" as used herein in refers to a fragment of a corresponding protein that contains the protein's C-terminus but lacks all sequences N-terminal to an internal residue.

Although not intending to be bound by theory, the Smad7 protein activity is generally believed to be the result of interactions in both the cytoplasm and nucleus of a cell. For that reason among others, there existed a general belief that Smad7 protein was not a candidate for a therapeutic role. However, it was decided to pursue development of Smad7 as a protein therapeutic, and modify the Smad7 nucleic acid sequence to encode a protein transduction domain (PTD) in frame with the Smad7 nucleic acid sequence (e.g., optionally any nucleic acid sequence described herein encoding Smad7 protein, including human wild-type and codon-optimized sequences, both full-length and biologically active fragments or truncated portions). In some embodiments, the PTD is located at the 3' end of the Smad7 nucleic acid sequence, and in some embodiments the PTD is located at the 5' end of the Smad7 nucleic acid sequence. In some embodiments, there is a linker sequence encoding 1, 2, 3, 4, 5, or 6 amino acids that connects the PTD and the Smad7 nucleic acid sequence.

In some embodiments, the PTD nucleic acid sequence is a Tat nucleic acid sequence. ggccgtaaaaaacgccgtcaacgccgccgt (SEQ ID NO: 1) encoding GRKKRRQRRR (SEQ ID NO: 2), tatggccgtaaaaaacgccgtcaacgccgccgt (SEQ ID NO: 3) encoding YGRKKRRQRRR (SEQ ID NO: 4), or ggccgtaaaaaacgc- cgtcaa (SEQ ID NO: 5) encoding GRKKRRQ (SEQ ID NO: 6).

In some embodiments, the nucleic acid sequence further includes a nucleotide sequence encoding one or more of an epitope tag or a purification tag. In some embodiments, the epitope tag is V5. In some embodiments, the purification tag is one or more of glutathione-S-Transferase (GST) or 6-histidine (H6) (SEQ ID NO: 40).

The term "epitope tag" as used herein in reference to nucleic acid molecules refers to nucleotides encoding peptide sequences that are recognized and bound by the variable region of an antibody or fragment. In some embodiments, the epitope tag is not part of the native protein. In some embodiments, the epitope tag is removable. In some embodiments, the epitope tag is not intrinsic to the protein's native biological activity. Examples of epitope tags include, but are not limited to V5.

The term "purification tag" as used herein in reference to nucleic acid molecules refers to nucleotides encoding peptide sequences that facilitate the purification of the protein, but are generally not necessary for the protein's biological activity. In some embodiments, purification tags may be removed following protein purification. Examples of purification tags include, but are not limited to GST and H-6 (SEQ ID NO: 40).

2. Vectors for Cloning, Gene Transfer and Expression

Within certain embodiments, expression vectors are employed to express the Smad7 polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well-equipped to construct a vector through standard recombinant techniques, which are described, e.g., in Sambrook, et al., *Molecular Cloning* (Cold Spring Harbor Lab Press, 1989), and Ausubel, et al., *Current Protocols in Molecular Biology* (Wiley, 1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism, including promoters and enhancers. In addition to control sequences that govern transcription and translation, vectors and expression vectors may contain nucleic acid sequences that serve other functions, such as transcription termination signals and poly-adenylation sites.

The capacity of certain viral vectors to efficiently infect or enter cells, to integrate into a host cell genome and stably express viral genes, have led to the development and application of a number of different viral vector systems. Robbins, et al., *Pharmacol. Ther.* 80:35-47 (1998). Viral systems are currently used as vectors for ex vivo and in vivo gene transfer. For example, adenovirus, herpes-simplex virus, lentiviruses, retrovirus and adeno-associated virus vectors are being evaluated currently for treatment of diseases such as cancer, cystic fibrosis, Gaucher disease, renal disease and arthritis. Robbins, et al., *Pharmacol. Ther.* 80:35-47 (1998); Imai, et al., *Nephrologie* 19:379-402 (1998); U.S. Pat. No. 5,670,488. The various viral vectors present specific advantages and disadvantages, depending on the particular gene-therapeutic application.

Suitable non-viral methods for nucleic acid delivery for transformation of an organelle, a cell, a tissue or an organism for use with the present technology are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham, et al., *Virology* 52:456-467 (1973); Chen, et al., *Mol. Cell Biol.* 7:2745-2752 (1987); Rippe, et al., *Mol. Cell Biol.* 10:689-695 (1990)); by using DEAE-dextran followed by polyethylene glycol (Gopal, *Mol. Cell Biol.* 5:1188-1190 (1985)); by direct sonic loading (Fechheimer, et al., *PNAS* 84:8463-8467 (1987)); by liposome mediated transfection (Nicolau, et al., *Biochim. Biophys. Acta* 721:185-190 (1982); Fraley, et al., *PNAS* 76:3348-3352 (1979); Nicolau, et al., *Methods Enzymol.* 149: 157-176 (1987); Wong, et al., *Gene* 10:87-94 (1980); Kaneda, et al., *J. Biol. Chem.* 264:12126-12129 (1989); Kato, et al., *J. Biol. Chem.* 266:3361-3364 (1991)); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler, et al., *Plant Cell Rep.* 9:415-418 (1990); U.S. Pat. Nos. 5,302,523 and 5,464,765, each incorporated herein by reference); or by PEG-mediated transformation of protoplasts (Omirulleh, et al., *Plant Mol. Biol.* 21:415-428 (1993); U.S. Pat. Nos. 4,684,611 and 4,952,500, each incorporated herein by reference); by desiccation/inhibition-mediated DNA uptake (Potrykus, et al., *Mol. Gen. Genet.* 199:169-177 (1985)). Through the application of techniques such as these, organelle(s), cell(s), tissue(s) or organism(s) may be stably or transiently transformed.

3. Expression Systems

Numerous expression systems exist that comprise at least a part or all of the compositions discussed above. Prokaryote- and/or eukaryote-based systems can be employed for use with the present technology to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes (e.g., bacteria or yeast), depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KCB, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

B. Smad7 Proteins and Protein Fragments

Mothers against decapentaplegic homolog 7 (Smad7) was previously identified as an antagonist of TGF-β signaling by several mechanisms including: (a) blockade of TGF-β receptor-mediated phosphorylation and nuclear translocation of signaling Smads; (b) increased degradation of TGF-β receptors and signaling Smads through specific ubiquitin-proteasome pathways and (c) inhibition of signaling Smads for their binding to Smad binding elements (SBEs). Smad7 also antagonizes other signaling pathways, like the NF-κB pathway.

Smad7 protein is encoded by the SMAD7 gene, discussed above. Like many other TGF-β family members, Smad7 is involved in cell signaling. It is a TGF-β type 1 receptor antagonist. It blocks TGF-β1 and activin associating with the receptor, blocking access to Smad2. It is an inhibitory Smad (I-SMAD) and is enhanced by SMURF2. Smad7 also enhances muscle differentiation.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, for example, an amino acid analog. As used herein, the terms encompass amino acid chains of any length, including full length proteins, wherein the amino acid residues are linked by covalent peptide bonds.

In one embodiment, the present technology relates to Smad7 protein compositions. In addition to the entire Smad7 molecule, the present technology also relates to truncated portions and fragments of the polypeptide that retain one or more activity associated with Smad7, such as, but not limited to, increasing proliferation, reducing or inhibiting cell death, reducing excessive inflammation, preventing DNA damage, and/or increasing cell migration, as well as treating or preventing one or more disease or disorders in which such treatment would be helpful as further discussed herein. Such activities can be assessed using one or more assays including, but not limited to, the ability to block phosphorylation of Smad2 and/or nuclear translocation of the NF-κB p50 subunit, increase cell proliferation, reduce apoptosis and/or radiation-induced DNA damage, reduce inflammation and/or angiogenesis, promote healing in oral mucositis, surgical wounds, diabetes wounds, and/or wounds associated with chronic inflammation in mice.

Protein fragments may be generated by genetic engineering of translation stop sites within the coding region (discussed below). Alternatively, treatment of the Smad7 molecule with proteolytic enzymes, known as proteases, can produces a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

As used herein, reference to an isolated protein or polypeptide in the present embodiments include full-length proteins, fusion proteins, chimeric proteins, or any fragment (truncated form, portion) or homologue of such a protein. More specifically, an isolated protein can be a protein (including a polypeptide or peptide) that has been removed from its natural milieu (i.e., that has been subject to human manipulation), and can include, but is not limited to, purified proteins, partially purified proteins, recombinantly produced proteins, proteins complexed with lipids, soluble proteins, synthetically produced proteins, and isolated proteins associated with other proteins. As such, "isolated" does not reflect the extent to which the protein has been purified. Preferably, an isolated protein is produced recombinantly.

Variants of Smad7 are also provided—these can be substitutional, insertional or deletion variants. Deletion variants lack one or more residues of the native protein that are not essential for activity, including the truncation mutants described above and herein. Substitutional variants typically contain the exchange of one amino acid for another at one or more sites within the protein, and may be designed to modulate one or more properties of the polypeptide, such as stability against proteolytic cleavage and/or translation and/or transcription (protein expression), without the loss of other functions or properties. Substitutions of this kind preferably are conservative, that is, one amino acid is replaced with one of similar shape and charge. Conservative substitutions are well known in the art and include, for example, each amino acid can be changed or substituted with a different amino acid. In making substitutional variants, the hydropathic index, hydrophilicity, charge and size are normally considered.

Specifically contemplated deletion variants of Smad7 include truncations and fragments, for example, including polypeptide molecules having N-terminal sequences, but not C-terminal sequences, having C-terminal sequences but not N-terminal sequences, or having internal sequences, but not N-terminal or c-terminal sequences. Specifically contemplated Smad7 polypeptide truncations or fragments include, but are not limited to, molecules including amino acid residues 2-258, 259-426, 204-258 corresponding to the native human Smad7 protein sequence.

The term "truncated" as used herein in reference to protein sequences refers to a molecule that contains the natural N-terminus of a corresponding protein (with or without a cleaved leader sequence), but lacks one or more amino acids starting from the C-terminus of the molecule, or a molecule that contains the natural C-terminus of a corresponding protein (with or without a cleaved leader sequence), but lacks one or more amino acids starting from the N-terminus of the molecule. In some embodiments, molecules lacking at least about 25, at least about 50, at least about 75, at least about 100, at least about 125, at least about 150, at least about 200, at least about 250, at least about 300, or at least about 350, or at least about 400 amino acids from one or the other terminus are specifically provided. In some embodiments, a "truncated" molecule is biologically active, having one or more of the Smad7 activities described herein.

The term "fragment" as used herein in reference to polypeptide sequences refers to a molecule containing contiguous residues of a full length sequence but lacking some N-terminal and/or C-terminal residues of the full length sequence. In some embodiments, a "fragment" includes a portion of one or more of the full length sequences described herein. In some embodiments, the "fragment" does not include sequences encoding either the N-terminal or the C-terminal, but only internal fragments. In some embodiments, a "fragment" encodes a polypeptide that is biologically active, having one or more of the Smad7 activities described herein. In some embodiments, polypeptide fragments have at least about 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150 amino acids.

A specialized kind of variant is the fusion protein. This molecule generally has all or a substantial portion of the native molecule, linked at the N- or C-terminus, to all or a portion of a second polypeptide. However, in some embodiments, the fusion protein may include any one of the fragments and/or truncated (N-terminal, C-terminal) Smad7 proteins described throughout the disclosure. For example, fusions may employ leader sequences from other species to permit the recombinant expression of a protein in a heterologous host. Another useful fusion includes the addition of an optional functionally active domain, such as but not limited to an antibody epitope and/or a purification tag (e.g., V5: GKPIPNPLLGLDST (SEQ ID NO: 41); Flag: KYKDDDDK (SEQ ID NO: 42); HA: YPYDVPDYA (SEQ ID NO: 43)). Another type of fusion includes attaching a domain that can act as the target for an activating or inactivating ligand, thereby permitting control of the fusion protein's function once delivered to a subject. Such domains include, for example, steroid ligand binding (e.g., ER, PR, GR), which can be activated by small molecules, e.g., 4-hydroxyl tamoxifen or RU486 that are either uniquely able to activate those steroid ligand binding domains and/or do not exist in nature and will therefore enable full control of the Smad7 function by the presence of these small molecules.

Another specific form of a fusion protein finding particular utility in the present technology is a fusion including a protein transduction domain (PTD), also called a cell delivery domain or cell transduction domain. Such domains have been described in the art and are generally characterized as short amphipathic or cationic peptides and peptide derivatives, often containing multiple lysine and arginine resides (Fischer, *Med. Res. Rev.* 27:755-795 (2007)). In some embodiments, the PTD is one or more variant of TAT protein from HIV (GRKKRRQRRR (SEQ ID NO: 2), YGRKKRRQRRR (SEQ ID NO: 4), or GRKKRRQ (SEQ ID NO: 6)) or alternatively, HSV VP16. Alternate forms of Tat may be used. In some embodiments, a linker may be used to connect one or more PTDs and SMad7. In some embodiments, the PTD (optionally Tat) is fused or linked in frame to the N-terminal and/or C-terminal end of any one of the Smad7 full-length, fragments, and/or truncated (N-terminal, C-terminal) proteins described throughout the disclosure. Other examples of PTDs provided by the present technology are shown in Table 1.

TABLE 1

PROTEIN TRANSDUCTION DOMAINS

| | SEQ ID NO: |
|---|---|
| GALFLGWLGAAGSTMGAKKKRKV | 44 |
| RQIKIWFQNRRMKWKK | 45 |
| RRMKWKK | 46 |
| RRWRRWWRRWWRRWRR | 47 |
| RGGRLSYSRRRFSTSTGR | 48 |
| YGRKKRRQRRR | 4 |
| RKKRRQRRR | 49 |
| YARAAARQARA | 50 |
| RRRRRRRR | 51 |
| KKKKKKKK | 52 |
| GWTLNSAGYLLGKINLKALAALAKXIL | 53 |
| LLILLRRRIRKQANAHSK | 54 |
| SRRHHCRSKAKRSRHH | 55 |
| NRARRNRRRVR | 56 |
| RQLRIAGRRLRGRSR | 57 |
| KLIKGRTPIKFGK | 58 |
| RRIPNRRPRR | 59 |
| KLALKLALKALKAALKLA | 60 |
| KLAKLAKKLAKLAK | 61 |
| GALFLGFLGAAGSTNGAWSQPKKKRKV | 62 |
| KETWWETWWTEWSQPKKKRKV | 63 |
| LKKLLKKLLKKLLKKLLKKL | 64 |
| QAATATRGRSAASRPTERPRAPARSASRPRRPVE | 65 |
| MGLGLHLLVLAAALQGAKSKRKV | 66 |
| AAVALLPAVLLALLAPAAANYKKPKL | 67 |
| MANLGYWLLALFVTMWTDVGLCKKRPKP | 68 |
| LGTYTQDFNKFHTFPQTAIGVGAP | 69 |
| DPKGDPKGVTVTVTVTVTGKGDPXPD | 70 |
| PPPPPPPPPPPPPP | 71 |
| VRLPPPVRLPPPVRLPPP | 72 |
| PRPLPPPRPG | 73 |
| SVRRRPRPPYLPRPRPPPFFPPRLPPRIPP | 74 |
| TRSSRAGLQFPVGRVHRLLRK | 75 |
| GIGKFLHSAKKFGKAFVGEIMNS | 76 |
| KWKLFKKIEKVGQNIRDGIIKAGPAVAVVGQATQIAK | 77 |
| ALWMTLLKKVLKAAAKAALNAVLVGANA | 78 |
| GIGAVLKVLTTGLPALISWIKRKRQQ | 79 |
| INLKALAALAKKIL | 80 |

TABLE 1-continued

PROTEIN TRANSDUCTION DOMAINS

| | SEQ ID NO: |
|---|---|
| GFFALIPKIISSPLPKTLLSAVGSALGGSGGQE | 81 |
| LAKWALKQGFAKLKS | 82 |
| SMAQDIISTIGDLVKWIIQTVNXFTKK | 83 |
| LLGDFFRKSKEKIGKEFKRIVQRIKQRIKDFLANLVPRTES | 84 |
| PAWRKAFRWAWRMLKKAA | 85 |
| KLKLKLKLKLKLKLKLKL | 86 |

In particular embodiments, the present technology provides for sequence variants of Smad7 in which one or more residues have been altered. For example, in one embodiment, the methionine residue found at position 216 of the human Smad7 sequence is modified to a leucine residue (ATG to CTG).

C. Methods of Treatment

Smad7-treatable diseases and disorders may include those including one or more of reduced cell proliferation, reduced cell migration, increased cell death, excessive inflammation, and/or DNA damage. Smad7-related diseases and disorders may include those where treatment with a Smad7 protein and biologically active fragments and derivatives thereof that have one or more activities including but not limited to increasing proliferation, reducing or inhibiting cell death, reducing excessive inflammation, preventing DNA damage, and/or increasing cell migration is helpful. Such diseases and/or disorders may include but are not limited to acute (e.g., through surgery, combat, trauma) and chronic wounds (e.g., ulcers, such as diabetic, pressure, venous), scarring, fibrosis, and aberrant healing, mucositis (e.g., oral and/or gastro-intestinal), stomatitis, proctitis, autoimmune disease (e.g., psoriasis, arthritis), and cancer.

In some embodiments, one or more of the diseases and or disorders described herein may be prevented, treated, and/or ameliorated by providing to a subject in need of such treatment a therapeutically effective amount of one or more of the Smad7 proteins (e.g., full-length or biologically active truncated (e.g., N-terminal or C-terminal) or fragment thereof) described in the disclosure. In some embodiments, the one or more Smad7 proteins are fusion proteins including a PTD domain. In some embodiments, the one or more Smad7 proteins includes Leu216. In some embodiments, the Smad7 proteins make part of a pharmaceutical composition including one or more pharmaceutically acceptable excipients.

In some embodiments, one or more of the diseases and or disorders described herein may be prevented, treated, and/or ameliorated by providing to a subject in need of such treatment a therapeutically effective amount of one or more of the nucleic acid molecules encoding one or more Smad7 proteins (e.g., full-length or biologically active truncated (e.g., N-terminal or C-terminal) or fragment thereof) described in the disclosure. In some embodiments, the one or more nucleic acid molecules include codon-optimized nucleotide sequences and/or sequences that encode Leu216. In some embodiments, the one or more Smad7 nucleic acid molecules are provided to the subject in a construct including an expression vector. In some embodiments, the Smad7 nucleic acid molecules (optionally part of an expression vector) make part of a pharmaceutical composition including one or more pharmaceutically acceptable excipients.

The term "subject" or "patient" as used herein refers to persons or non-human animals in need of treatment and or prevention using one or more of the treatments described herein. In some embodiments, non-human animals include laboratory animals such as monkeys, mice, rats, and rabbits, domestic pets such as dogs and cats, and livestock such as cattle, horses, pigs, goats and sheep.

1. Chronic Wounds

A chronic wound is a wound that does not heal in an orderly set of stages and in a predictable amount of time the way most wounds do; wounds that do not heal within three months are often considered chronic. Chronic wounds seem to be detained in one or more of the phases of wound healing. For example, chronic wounds often remain in the inflammatory stage for too long. In acute wounds, there is a precise balance between production and degradation of molecules such as collagen; in chronic wounds this balance is lost and degradation plays too large a role.

As described in more detail elsewhere herein, PTD-Smad7 has been shown to enhance wound healing in a mouse skin model and a mucosal model. Application of PTD-Smad7 was effective through a topical route, which is desirable for wound treatment. Although not intending to be bound by theory, it is believed that PTD-Smad7 may act to treat or ameliorate chronic wounds through multiple routes, which may include one or more of reducing inflammation, increasing cell proliferation (e.g., keratinocytes), increasing cell migration (e.g., keratinocytes), or reducing fibrosis (e.g., through modulation of collagen), among others.

Chronic wounds may never heal or may take years to do so. These wounds cause patients severe emotional and physical stress as well as creating a significant financial burden on patients and the whole healthcare system. Acute and chronic wounds are at opposite ends of a spectrum of wound healing types that progress toward being healed at different rates. The vast majority of chronic wounds can be classified into three categories: venous ulcers, diabetic, and pressure ulcers. A small number of wounds that do not fall into these categories may be due to causes such as radiation poisoning or ischemia.

Venous and Arterial Ulcers.

Venous ulcers, which usually occur in the legs, account for about 70% to 90% of chronic wounds and mostly affect the elderly. They are thought to be due to venous hypertension caused by improper function of valves that exist in the veins to prevent blood from flowing backward. Ischemia results from the dysfunction and, combined with reperfusion injury, causes the tissue damage that leads to the wounds.

Diabetic Ulcers.

Another major cause of chronic wounds, diabetes, is increasing in prevalence. Diabetics have a 15% higher risk for amputation than the general population due to chronic ulcers. Diabetes causes neuropathy, which inhibits nociception and the perception of pain. Thus patients may not initially notice small wounds to legs and feet, and may therefore fail to prevent infection or repeated injury. Further, diabetes causes immune compromise and damage to small blood vessels, preventing adequate oxygenation of tissue, which can cause chronic wounds. Pressure also plays a role in the formation of diabetic ulcers.

Pressure Ulcers.

Another leading type of chronic wounds is pressure ulcers, which usually occur in people with conditions such as paralysis that inhibit movement of body parts that are commonly subjected to pressure such as the heels, shoulder blades, and sacrum. Pressure ulcers are caused by ischemia that occurs when pressure on the tissue is greater than the pressure in capillaries, and thus restricts blood flow into the area. Muscle tissue, which needs more oxygen and nutrients than skin does, shows the worst effects from prolonged pressure. As in other chronic ulcers, reperfusion injury damages tissue.

Chronic wounds may affect only the epidermis and dermis, or they may affect tissues all the way to the fascia. They may be formed originally by the same things that cause acute wounds, such as surgery or accidental trauma, or they may form as the result of systemic infection, vascular, immune, or nerve insufficiency, or comorbidities such as neoplasias or metabolic disorders. Although not intending to be bound by theory, the reason a wound becomes chronic is that the body's ability to deal with the damage is overwhelmed by factors such as repeated trauma, continued pressure, ischemia, or illness. Some of the major factors that lead to chronic wounds include, but are not limited to, ischemia, reperfusion injury, and bacterial colonization.

Ischemia.

Ischemia is an important factor in the formation and persistence of wounds, especially when it occurs repetitively (as it usually does) or when combined with a patient's old age. Ischemia causes tissue to become inflamed and cells to release factors that attract neutrophils such as interleukins, chemokines, leukotrienes, and complement factors.

While they fight pathogens, neutrophils also release inflammatory cytokines and enzymes that damage cells. One of their important functions is to produce Reactive Oxygen Species (ROS) to kill bacteria, for which they use an enzyme called myeloperoxidase. The enzymes and ROS produced by neutrophils and other leukocytes damage cells and prevent cell proliferation and wound closure by damaging DNA, lipids, proteins, the ECM, and cytokines that speed healing. Neutrophils remain in chronic wounds for longer than they do in acute wounds, and contribute to the fact that chronic wounds have higher levels of inflammatory cytokines and ROS. Because wound fluid from chronic wounds has an excess of proteases and ROS, the fluid itself can inhibit healing by inhibiting cell growth and breaking down growth factors and proteins in the ECM.

Bacterial Colonization.

Since more oxygen in the wound environment allows white blood cells to produce ROS to kill bacteria, patients with inadequate tissue oxygenation, for example, those who suffered hypothermia during surgery, are at higher risk for infection. The host's immune response to the presence of bacteria prolongs inflammation, delays healing, and damages tissue. Infection can lead not only to chronic wounds but also to gangrene, loss of the infected limb, and death of the patient.

Like ischemia, bacterial colonization and infection damage tissue by causing a greater number of neutrophils to enter the wound site. In patients with chronic wounds, bacteria with resistance to antibiotics may have time to develop. In addition, patients carrying drug resistant bacterial strains, such as methicillin-resistant *Staphylococcus aureus* (MRSA), have more chronic wounds.

Growth Factors and Proteolytic Enzymes.

Chronic wounds also differ in makeup from acute wounds in that their levels of proteolytic enzymes such as elastase and matrix metalloproteinases (MMPs) are higher, while their concentrations of growth factors such as Platelet-derived growth factor and Keratinocyte Growth Factor are lower.

Since growth factors (GFs) are imperative in timely wound healing, inadequate GF levels may be an important factor in chronic wound formation. In chronic wounds, the formation and release of growth factors may be prevented, the factors may be sequestered and unable to perform their metabolic roles, or degraded in excess by cellular or bacterial proteases.

Chronic wounds such as diabetic and venous ulcers are also caused by a failure of fibroblasts to produce adequate ECM proteins and by keratinocytes to epithelialize the wound. Fibroblast gene expression is different in chronic wounds than in acute wounds.

Although all wounds require a certain level of elastase and proteases for proper healing, too high a concentration is damaging. Leukocytes in the wound area release elastase, which increases inflammation, destroys tissue, proteoglycans, and collagen, and damages growth factors, fibronectin, and factors that inhibit proteases. The activity of elastase is increased by human serum albumin, which is the most abundant protein found in chronic wounds. However, chronic wounds with inadequate albumin are especially unlikely to heal, so regulating the wound's levels of that protein may in the future prove helpful in healing chronic wounds.

Excess matrix metalloproteinases, which are released by leukocytes, may also cause wounds to become chronic. MMPs break down ECM molecules, growth factors, and protease inhibitors, and thus increase degradation while reducing construction, throwing the delicate compromise between production and degradation out of balance.

Oral Ulcers.

A mouth ulcer (also termed an oral ulcer, or a mucosal ulcer) is an ulcer that occurs on the mucous membrane of the oral cavity. More plainly, a mouth ulcer is a sore or open lesion in the mouth. Mouth ulcers are very common, occurring in association with many diseases and by many different mechanisms, but usually there is no serious underlying cause. The two most common causes of oral ulceration are local trauma (e.g., rubbing from a sharp edge on a filling) and aphthous stomatitis ("canker sores"), a condition characterized by recurrent formation of oral ulcers for largely unknown reasons. Some consider ulcers on the lips or on the skin around the mouth to be included under the general term oral ulceration (e.g., an ulcer left by rupture of a blister caused by herpes labialis, i.e., a cold sore). Mouth ulcers often cause pain and discomfort, and may alter the person's choice of food while healing occurs (e.g., avoiding acidic or spicy foods and beverages). They may occur singly or multiple ulcers may occur at the same time (a "crop" of ulcers). Once formed, the ulcer may be maintained by inflammation and/or secondary infection. Rarely, a mouth ulcer that does not heal for many weeks may be a sign of oral cancer. Other causes include burns, chemical injury, or infection.

A mucosal ulcer is an ulcer which specifically occurs on a mucous membrane. An ulcer is a tissue defect which has penetrated the epithelial-connective tissue border, with its base at a deep level in the submucosa, or even within muscle or periosteum. An ulcer is a deeper breech of the epithelium than an erosion or an excoriation, and involves damage to both epithelium and lamina propria. An erosion is a superficial breach of the epithelium, with little damage to the underlying lamina propria. A mucosal erosion is an erosion which specifically occurs on a mucous membrane. Only the superficial epithelial cells of the epidermis or of the mucosa are lost, and the lesion can reach the depth of the basement membrane. Erosions heal without scar formation. Excoriation is a term sometimes used to describe a breach of the epithelium which is deeper than an erosion but shallower than an ulcer. This type of lesion is tangential to the rete pegs and shows punctiform (small pinhead spots) bleeding, caused by exposed capillary loops.

2. Acute Wounds/Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present technology provides for treatment of trauma, including both pre-treatment (in the case of a medical procedure) and treatment after trauma injury has occurred.

As described in more detail elsewhere herein (and briefly mentioned above), PTD-Smad7 has been shown to enhance wound healing in a mouse skin model and a mucosal model. Application of PTD-Smad7 was effective through a topical route, which is desirable for wound treatment. Although not intending to be bound by theory, it is believed that PTD-Smad7 may act to treat or ameliorate wounds through multiple routes, which may include one or more of reducing inflammation, increasing cell proliferation (e.g., keratinocytes), increasing cell migration (e.g., keratinocytes), or reducing fibrosis (e.g., through modulation of collagen), among others. As described briefly below, reduced inflammation could significantly contribute to accelerated wound healing, optionally through reduced angiogenesis and collagen production and/or reduced leukocyte infiltration leading to reduction of cytokines and chemokines normally released by leukocytes, which are angiogenic and fibrogenic. Temporal treatment with Smad7 may allow early stage angiogenesis and collagen production required for wound repair, while preventing prolonged angiogenesis and collagen production. These changes could potentially accelerate wound stromal remodeling and prevent excessive scarring due to unresolved inflammation or collagen overproduction. For surgical procedures (as well as everyday injuries), particularly where the potential for scarring is an issue, treatment with Smad7 may be beneficial.

Surgery.

Surgery uses operative manual and instrumental techniques on a patient to investigate and/or treat a pathological condition such as disease or injury, to help improve bodily function or appearance, or sometimes for some other reason. The present technology can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classified by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

3. Autoimmune/Inflammatory Disease

The present technology contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

In general, autoimmune diseases are associated with an overactive immune response of a body against substances and tissues normally present in the body, and not normally the focus of an immune response. There are more than 80 types of autoimmune diseases, some of which have similar symptoms, and they may arise from a similar underlying cause. The classic sign of an autoimmune disease is inflammation, which as disclosed herein is amenable to treatment with Smad7 (optionally PTD-Smad7) compositions.

4. Chemotherapy, Radiotherapy and Cytokine Therapy Toxicity

Various forms of cancer therapy, including chemotherapy, radiation, and cytokines, are associated with toxicity, sometimes severe, in the cancer patient. The present technology seeks to reduce this toxicity using the pharmaceutical compositions of the present technology, thereby reducing or alleviating discomfort on the part of the patient, as well as permitting higher doses of the therapy.

As described at length throughout this disclosure, it has been found that PTD-Smad7 acts to heal as well as to prevent oral mucositis in a mouse model. PTD-Smad7 was shown to be more effective than palifermin, the existing approved drug for preventing oral mucositis, in direct comparisons.

Oral cancer, the 6th most common cancer worldwide, is a subtype of head and neck cancer, and includes any cancerous tissue growth located in the oral cavity. It may arise as a primary lesion originating in any of the oral tissues, by metastasis from a distant site of origin, or by extension from a neighboring anatomic structure, such as the nasal cavity or the oral cancers may originate in any of the tissues of the mouth, and may be of varied histologic types: teratoma, adenocarcinoma derived from a major or minor salivary gland, lymphoma from tonsillar or other lymphoid tissue, or melanoma from the pigment-producing cells of the oral mucosa. There are several types of oral cancers, but around 90% are squamous cell carcinomas, originating in the tissues that line the mouth and lips. Oral or mouth cancer most commonly involves the tongue. It may also occur on the floor of the mouth, cheek lining, gingiva (gums), lips, or palate (roof of the mouth). Most oral cancers look very similar under the microscope and are called squamous cell carcinoma. These are malignant and tend to spread rapidly.

Over 80% of oral cancer patients are treated with radiation therapy and at least 75% of these individuals will develop oral mucositis. Oral mucositis is a chronic oral ulceration. This disease frequently occurs in radiation-treated patients of all cancer types, including but not limited to patients who are radiation-treated for organ transplants (to eliminate rejection of the transplants), and patients undergoing routine chemotherapy. Severe oral mucositis is extremely painful and impairs food/liquid intake, hence is often the most severe complication of cancer therapy. Oral mucositis is a major factor in determining the maximum dose possible of radiation and chemotherapy to the head and neck region; it can significantly complicate cancer treatment, extend hospitalization, decrease quality of life and increase costs.

Currently, there is no established therapy to effectively treat severe oral mucositis. To date, palifermin (KEPIVANCE®), a recombinant protein of human keratinocyte growth factor (KGF), is the only FDA approved drug for intravenous (i.v.) injections for severe oral mucositis in bone-marrow transplant patients, and its use in cancer patients remains to be determined. It is also used for prevention of oral mucositis. Hence, this drug is available for only 4% of the at-risk population. It also suffers from the need for medical service providers due to the i.v. administration route. Other potential therapies include topical rinses, such as viscous 2% lidocaine rinses, or baking soda and saline solutions, or a cocktail solution, for instance BAX (lidocaine, diphenhyramine, sorbitol and MYLANTA®). Other investigative or mucoprotective adjuvant therapies include, but are not limited to, beta carotene, tocopherol, laser irradiation, prophylactic brushing the oral mucosa with silver-nitrate, misoprostol, leucovorin, systemic KGF, pentoxifylline, allopurinol mouthwash, systemic sucralfate, chlorhexidine gluconate, and cryotherapy.

Chemotherapy- and radiation-induced gut mucositis is an inflammatory condition that arises as a result of the acute death of rapidly dividing intestinal epithelial cells. Most chemotherapeutic drugs used for treatment of solid tumors, alone, in a combination of drugs, or with radiation, will result in the death of a large number of intestinal epithelial cells. The clinical manifestations of the ensuing mucositis include digestive symptoms such as nausea and vomiting, serious diarrhea, acute weight loss and wasting. This is fast becoming one of the limiting factors for administering chemotherapy for many cancer patients. The ability of Tat-Smad7 to protect intestinal epithelial cells from either chemotherapeutic agents, radiation, or a combinations of those, will significantly decrease the undesirable side effects of cancer therapies, and enable more aggressive ways to treat the disease with existing tools.

Bone marrow failure syndromes are a set of conditions that develop when the hematopoietic stem cell compartment is compromised and fails to give rise to normal cell types. Bone marrow failure occurs as a result of inherited genetic abnormalities, exposure to a noxious substance, such as toxins, chemicals or viruses. Although the nature and identity of environmental factors that can lead to the development of acquired bone marrow failure is still not completely understood, a few factors have been linked to the development of acquired bone marrow failure among military personnel including exposure to mustard gas, ionizing radiation, and infectious agents such as visceral leishmaniasis or African trypanosomiasis. The best approach for management of bone marrow failure syndromes is still the transplantation of hematopoietic stem cells (HSCs), unless a sufficient number of the remaining resident bone marrow HSCs can be spared from these stresses and encouraged to repopulate the hematopoietic compartment. The modulation of Smad 7, as described here, should enable for the deliberate protection of the remaining resident HSCs in patients that exhibit clinical signs consistent with bone marrow failure.

5. Cancer

TGF-β and NF-κB activations are known to promote cancer invasion and metastasis. Currently, TGF-β inhibitors are in clinical trials for treating metastatic cancer and NF-κB inhibitors are used in cancer prevention. The demonstrated effect of Smad7 on blocking both TG and NF-κB signaling present the possibility that it is an even stronger anti-cancer/anti-metastasis agent than other inhibitors that inhibit only one of these two pathways. Smad7 has been shown to prevent angiogenesis and fibrogenesis, and may therefore be particularly useful in situations where the tumor needs to develop a blood supply and/or stroma.

The cancer may be selected from the group consisting of brain, lung, liver, spleen, kidney, lymph node, small intestine, pancreas, blood cells, colon, stomach, breast, endometrium, prostate, testicle, cervix, uterus, ovary, skin, head & neck, esophagus, bone marrow and blood cancer. The cancers may be metastatic or primary, recurrent or multi-drug resistant. In some embodiments, the cancer is a solid tumor (organ tumor). Solid tumors refer to a mass of cells that grow in organ systems and can occur anywhere in the body. Two types of solid tumors include epithelial tumors (carcinomas) that occur in the epithelial tissue inside or outside an organ, and sarcomas (connective tissue tumors) that occur in connective tissue such as, but not limited to, muscles, tendons, fat, nerves and other connective tissues that support, surround, or connect structures and organs in the body. In some embodiments the cancer is a liquid tumor or cancer of the blood, bone marrow, or lymph nodes. These tumors include, but are not limited to, leukemia, lymphoma, and myeloma.

6. Scarring, Fibrosis, and Aberrant Healing

In addition to accelerated re-epithelialization (e.g., through increasing cell proliferation and/or increasing cell migration), Smad7 effects on wound stroma include one or more of reducing inflammation, angiogenesis, or collagen production, among others. Although not intending to be bound by theory these effects may be mediated through reduction of NF-κB signaling (evidenced by reduced p50), and blocking TGF-β signaling (evidenced by reduced pSmad2). As a result, reduced inflammation could significantly contribute to accelerated wound healing, optionally through reduced angiogenesis and collagen production and/or reduced leukocyte infiltration leading to reduction of cytokines and chemokines normally released by leukocytes, which are angiogenic and fibrogenic. Temporal treatment with Smad7 may allow early stage angiogenesis and collagen production required for wound repair, while preventing prolonged angiogenesis and collagen production. These changes could potentially accelerate wound stromal remodeling and prevent excessive scarring due to unresolved inflammation or collagen overproduction.

7. Stomatitis

Stomatitis is an inflammation of the mucous lining of any of the structures in the mouth, which may involve the cheeks, gums, tongue, lips, throat, and roof or floor of the mouth. The inflammation can be caused by conditions in the mouth itself, such as poor oral hygiene, dietary protein deficiency, poorly fitted dentures, or from mouth burns from hot food or drinks, toxic plants, or by conditions that affect the entire body, such as medications, allergic reactions, radiation therapy, or infections. Severe iron deficiency anemia can lead to stomatitis. Iron is necessary for the upregulation of transcriptional elements for cell replication and repair. Lack of iron can cause the genetic downregulation of these elements, leading to ineffective repair and regeneration of epithelial cells, especially in the mouth and lips. This condition is also prevalent in people who have a deficiency in vitamin $B_2$ (Riboflavin), $B_3$ (Niacin), $B_6$ (Pyridoxine), $B_9$ (folic acid) or $B_{12}$ (cobalamine) When it also involves an inflammation of the gingiva (gums), it is called gingivostomatitis. It may also be seen in ariboflavinosis (riboflavin deficiency) or neutropenia.

Irritation and fissuring in the corners of the lips is termed angular stomatitis or angular cheilitis. In children, angular stomatitis is a frequent cause is repeated lip-licking and in adults it may be a sign of underlying iron deficiency anemia, or vitamin B deficiencies (e.g., $B_2$-riboflavin, $B_9$-folate or $B_{12}$-cobalamin), which in turn may be evidence of poor diets or malnutrition (e.g., celiac disease). Also, angular cheilitis can be caused by a patient's jaws at rest being "overclosed" due to edentulousness or tooth wear, causing the jaws to come to rest closer together than if the complete/unaffected dentition were present. This causes skin folds around the angle of the mouth which are kept moist by saliva which in turn favours infection; mostly by *Candida albicans* or similar species. Treatment usually involves the administration of topical nystatin or similar antifungal agents. Another treatment can be to correct the jaw relationship with dental treatment (e.g., dentures or occlusal adjustment).

Migratory stomatitis is a condition in which extensive areas in the oral cavity mucosa are affected by annular atrophic red lesions that are surrounded by a thin white rim. This is a relatively uncommon form of the geographic tongue condition, that, as opposed to migratory stomatitis, is confined to the dorsal and lateral aspects of the tongue mucosa only.

8. Proctitis

Proctitis is inflammation of the lining of the rectum, the lower end of the large intestine leading to the anus. With proctitis, inflammation of the rectal lining—called the rectal mucosa—is uncomfortable and sometimes painful. The condition may lead to bleeding or mucous discharge from the rectum, among other symptoms. Some causes of proctitis include, but are not limited to: sexually transmitted diseases (STDs), such as those that can be transmitted during anal sex (e.g., gonorrhea, chlamydia, syphilis, and herpes); non-STD infections from, for example, food borne bacteria (e.g., *Salmonella* and *Shigella*); anorectal trauma from, for example, anal sex or the insertion of objects or substances into the rectum (e.g., chemicals from enemas); ulcerative colitis and Crohn's disease or other inflammatory bowel diseases, may cause ulcers (e.g., sores) in the inner lining of the colon and rectum; radiation therapy, particularly of the pelvic area (e.g., rectal, ovarian, or prostate cancer) which may lead to rectal bleeding; antibiotics which lead to a loss of commensal bacteria allowing harmful bacteria (e.g., *Clostridium difficile*) to cause disease.

9. Formulations and Routes of Administration

Where clinical applications are contemplated, it will be necessary to prepare pharmaceutical compositions—proteins, expression vectors, virus stocks, proteins and drugs—in a form appropriate for the intended application. Generally, this will entail preparing compositions that are essentially free of pyrogens, as well as other impurities that could be harmful to humans or animals.

PTD-Smad7 (and truncated variants) were purified extensively prior to use in animal models. PTD-Smad7 (and truncated versions) were prepared for topical and trans-mucosal application using a mixture of glycerol and PBS.

One will generally desire to employ appropriate salts and buffers to render delivery vectors stable and allow for uptake by target cells. Buffers also will be employed when recombinant cells are introduced into a patient. Aqueous compositions of the present technology comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present technology, its use in therapeutic compositions is contemplated. Supplementary active ingredients also can be incorporated into the compositions.

The active compositions of the present technology may include classic pharmaceutical preparations. Administration of these compositions according to the present technology will be via any common route so long as the target tissue is available via that route. Such routes of administration may include oral parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), nasal, buccal, urethral, rectal, vaginal, mucosal, dermal, or topical (including dermal, buccal, and sublingual). Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

Solutions of the active compounds as free base or pharmacologically acceptable salts can be prepared in water suitably mixed with a surfactant, such as hydroxypropylcellulose.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present technology may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The formulations are easily administered in a variety of dosage forms. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

For oral administration the polypeptides of the present technology may be incorporated with excipients and used in the form of non-ingestible mouthwashes and dentifrices. It is anticipated that virtually any pill or capsule type known to one of skill in the art including, e.g., coated, and time delay, slow release, etc., may be used with the present technology. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, creams, powders and slurries. The active ingredient may be added in a therapeutically effective amount to a paste dentifrice that may include water, binders, abrasives, flavoring agents, foaming agents, and humectants.

Pharmaceutical compositions suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions.

In one embodiment, an active agent compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the active agent compounds may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present technology may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT®), zein, shellac, and polysaccharides.

Powdered and granular compositions of a pharmaceutical preparation may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of pharmaceutical compositions which are suitable for oral administration may be prepared, packaged, and sold either in liquid form or in the form of a dry product intended for reconstitution with water or another suitable vehicle prior to use.

A tablet containing one or more active agent compounds described herein may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present technology may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as antioxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

Compositions for rectal delivery include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for administration in the mouth include lozenges.

In accordance with these embodiments, oral (topical, mucosal, and/or dermal) delivery materials can also include creams, salves, ointments, patches, liposomes, nanoparticles, microparticles, timed-release formulations and other materials known in the art for delivery to the oral cavity, mucosa, and/or to the skin of a subject for treatment and/or prevention of a condition disclosed herein. Certain embodiments concern the use of a biodegradable oral (topical, mucosal, and/or dermal) patch delivery system or gelatinous material. These compositions can be a liquid formulation or a pharmaceutically acceptable delivery system treated with a formulation of these compositions, and may also include activator/inducers.

The compositions for use in the methods of the present technology may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multilayer patches where the active agents are contained in a layer separate from the adhesive layer. Both types of patches also generally contain a backing layer and a liner that is removed prior to attachment to the recipient's skin. Transdermal drug delivery patches may also be comprised of a reservoir underlying the backing layer that is separated from the skin of the recipient by a semi-permeable membrane and adhesive layer. Transdermal drug delivery may occur through passive diffusion, electrotransport, or iontophoresis.

In certain embodiments, a patch contemplated herein may be a slowly dissolving or a time-released patch. In accordance with these embodiments, a slowly dissolving patch can be an alginate patch. In certain examples, a patch may contain a detectible indicator dye or agent such as a fluorescent agent. In other embodiments, a tag (e.g., detectible tag such as a biotin or fluorescently tagged agent) can be associated with a treatment molecule in order to detect the molecule after delivery to the subject. In certain embodiments, one or more oral delivery patches or other treatment contemplated herein may be administered to a subject three times daily, twice daily, once a day, every other day, weekly, and the like, depending on the need of the subject as assessed by a health professional. Patches contemplated herein may be oral-biodegradable patches or patches for exterior use that may or may not degrade. Patches contemplated herein may be 1 mm, 2 mm, 3 mm, 4 mm to 5 mm in size or more depending on need. In addition, skin patches are contemplated herein for use for example in a subject suffering from psoriasis. In treating psoriasis and chronic wounds, Smad7 can be delivered topically using vehicles such as glycerol, carboxymethycellulose. It can also use transdermal system (e.g., commercially available from 3M) for delivery. Subcutaneous injection into the lesion (in normal saline or PBS) can also be used.

In some embodiments, compositions may include short-term, rapid-onset, rapid-offset, controlled release, sustained release, delayed release, and pulsatile release compositions, providing the compositions achieve administration of a compound as described herein. See *Remington's Pharmaceutical Sciences* (18th ed.; Mack Publishing Company, Eaton, Pa., 1990), herein incorporated by reference in its entirety.

In certain embodiments, the compounds and compositions disclosed herein can be delivered via a medical device. Such delivery can generally be via any insertable or implantable medical device, including, but not limited to stents, catheters, balloon catheters, shunts, or coils. In one embodiment, the present technology provides medical devices, such as stents, the surface of which is coated with a compound or composition as described herein. The medical device of this technology can be used, for example, in any application for treating, preventing, or otherwise affecting the course of a disease or condition, such as those disclosed herein.

It is contemplated that any molecular biology, cellular biology or biochemical technique known in the art may be used to generate and/or test treatments provided herein. In addition, protein chemistry techniques are contemplated to assess utility of treatments in model systems developed herein (e.g., mouse model system).

10. Combination Therapies

It is common in many fields of medicine to treat a disease with multiple therapeutic modalities, often called "combination therapies." Many of the diseases described herein (e.g., inflammatory disease and cancer) are no exception. In some embodiments, to treat inflammatory disorders using the methods and compositions of the present technology, one would contact a target cell, organ or subject with a Smad7 protein, expression construct or activator and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the Smad7 agent and the other includes the other agent.

Alternatively, the Smad7 agent may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the Smad7 agent or the other therapy will be desired. Various combinations may be employed, where the Smad7 agent is "A," and the other therapy is "B," as exemplified below:

| | | | | |
|---|---|---|---|---|
| A/B/A | B/A/B | B/B/A | A/A/B | B/A/A |
| A/B/B | B/B/B/A | B/B/A/B | A/A/B/B | A/B/A/B |
| A/B/B/A | B/B/A/A | B/A/B/A | B/A/A/B | B/B/B/A |
| A/A/A/B | B/A/A/A | A/B/A/A | A/A/B/A | A/B/B/B |
| B/A/B/B | B/B/A/B | | | |

Other combinations are provided. Other agents suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation. A particular agent for combination use is an anti-TGF-β antibody.

The skilled artisan is directed to *Remington's Pharmaceutical Sciences*, 15th Edition, chapter 33, in particular, pages 624-652, 1990. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

As discussed above, the present technology has particular relevance to the treatment of DNA damage and/or inflammation resulting from certain anti-cancer therapies, and for the treatment of cancer. Thus, in particular, the present technology may be applied as a combination with cancer therapies. This process may involve contacting the cells, organ, or patient with the agents/therapies at the same time, including by contacting the cells, organ or patient with a single composition or pharmacological formulation that includes both agents, or with two distinct compositions or formulations at the same time, wherein one composition includes the Smad7 agent and the other includes the other agent. Alternatively, analogous to the chart set forth above, the compositions can be delivered at different times, including repeated doses of one or both agents.

Agents or factors suitable for use in a combined therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," are intended to be of use in the combined treatment methods disclosed herein. In treating cancer according to the present technology, one would contact the tumor cells with an agent in addition to the expression construct. This may be achieved by irradiating the localized tumor site; alternatively, the tumor cells may be contacted with the agent by administering to the subject a therapeutically effective amount of a pharmaceutical composition.

Various classes of chemotherapeutic agents are provided for use with in combination with peptides of the present technology. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The present technology also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore provided for use in combination cancer therapy in accordance with the present technology.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to *Remington's Pharmaceutical Sciences*, 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining Smad7 therapies with chemo- and radiotherapies, it also is contemplated that combination with immunotherapy, hormone therapy, toxin therapy and surgery. In particular, one may employ targeted therapies such as AVASTIN®, ERBITUX®, GLEEVEC®, HERCEPTIN®, and RITUXAN®.

In other embodiments, to assess the roles and mechanisms of Smad7 within the context of oral mucositis, "gene-switch" transgenic mouse models were developed to allow control of the level and duration of Smad7 transgene expression specifically in oral epithelia. In accordance with these embodiments, these models may be used to test other genes or downstream molecules for their effects on oral epithelia and oral mucosa. Thus, these models can be used for, but are not limited to, further analysis of oral wound healing biology and testing therapeutic approaches to oral wound healing. Molecular Smad7 targets identified in these studies can provide additional therapeutic targets for subjects suffering from oral mucositis. Models and resources developed herein can provide unique tools for analytical studies to identify biomarkers and therapeutic targets related to Smad7 overexpression and control, for example, downstream molecules turned on or bound by Smad7 can be identified as additional therapeutic targets for example, to treat oral mucositis, psoriasis and other conditions aggravated by TGF-β activities and NF-κB activities.

D. Kits

In certain embodiments, a kit provided herein may include compositions discussed above for treating a subject having a condition provided herein, such as but not limited to oral mucositis, psoriasis, or wound healing. The kits can include one or more containers containing the therapeutic Smad7 compositions of the present technology. Any of the kits will generally include at least one vial, test tube, flask, bottle, syringe or other container, into which compositions may be preferably and/or suitably aliquoted. Kits herein may also include a kit for assessing biological targets that contribute to a condition provided herein.

E. Methods of Predicting or Evaluating Responses

Also provided are methods for predicting and/or evaluating a response to treatment with Smad7 using by assessing the level of expression of one or more markers associated with exposure to Smad7. Such markers may include, but are not limited to, Rac1 for cell migration, NF-κB for inflammation, and TGF-β for growth arrest and inflammation. As is discussed in the Examples, methods for detection of and/or changes in the levels of one or more markers associated with Smad7 activity are provided and/or known in the art. In some embodiments, the level of expression of one or more of the Smad7 markers in a subject may be assessed, and based on the level detected, a decision may be made to treat (or to continue or discontinue treatment) with Smad7, or to employ an alternate treatment.

The term "detection of" as used herein refers to the ability to measure the presence or absence of a marker at some repeatable and controlled level. Typically, detection is performed over background values, which may include the noise (or detection limits) inherent in the testing system. As such, there is typically a "lower limit" of detection associated with an assay, and in order to be detected, a change may need to be above a certain cut-off level, for example. Determination of such limits is well-known in the art.

In some embodiments, detection is performed as compared to controls, which may include, but are not limited to, a comparison with data from normal subjects and/or comparable normal tissue (in the same or different subjects) absent the disease or disorder present in the subject (or the specific tissue of the subject tested). In some embodiments, the comparison may be between levels detected at a variety of time intervals (and/or locations) in a patient. In some embodiments, the detection needs to be statistically significant as compared to background or control levels; the ability to assess significance is well-known in the art, and exemplified in the Examples.

The term "changes in the levels" as used herein refers to a detectable change from a control or background level, and or a previously detected level. In some embodiments, the change is an increase as compared to another level, and in some embodiments the change is a decrease as compared to another level. In some embodiments, the detectable change (increase or decrease) is statistically significant. In some embodiments, such changes can be assessed quantitatively as at least about a 5%, 10%, 25%, 50%, 100%, 200%, 500% or greater change, and/or about a 5-10%, 10-25%, 10-50%, 25-50%, 50-75%, 50-100%, 100-150%, 100-200%, 200-300%, 300-500%, or 500-1000% change.

F. Method of Screening for Additional Biologically Active Fragments

In another aspect, methods of screening for additional biologically active fragments (including, but not limited to truncations) of Smad7 are contemplated. In some embodiments, biological activity may be assessed using one of the methods described herein, including those described below in Examples 5 and 8. Some of the biological activities that can be assessed include, but are not limited to, increasing cell proliferation, reducing or inhibiting cell death, reducing excessive inflammation, preventing DNA damage, and/or increasing cell migration, as well as animal models treating or preventing one or more disease or disorders in which such treatment would be helpful as further discussed herein. Such activities can be assessed using one or more assays including, but not limited to, the ability to block phosphorylation of Smad2 and/or nuclear translocation of the NF-κB p50 subunit, increase cell proliferation, reduce apoptosis and/or radiation-induced DNA damage, reduce inflammation and/or angiogenesis, promote healing in oral mucositis, surgical wounds, diabetes wounds, and/or wounds associated with chronic inflammation in mice and other laboratory models. Some specific examples include, but are not limited to, immunofluorescence (IF), immunohistochemistry (IHC), and TUNEL assay for apoptosis.

In some embodiments, biologically active fragments are those that are selected to include one or more or all of the activities described herein. In some embodiments, biologically active fragments selected to include only or primarily 1, only or primarily 2, only or primarily 3, only or primarily 4, or only or primarily 5 of the activities described herein. In some embodiments, biologically active fragments selected to exclude only or primarily 1, only or primarily 2, only or primarily 3, only or primarily 4, or only or primarily 5 of the activities described herein. In some embodiments, the biologically active fragments are selected to include or to exclude a specific subset of the activities described herein. For instance, increased proliferation and migration may be sufficient for treating diabetic wounds, whereas anti-inflammation is needed in chronic inflammatory wounds. Reduced apoptosis and DNA damage activities are needed for treating oral mucositis but not for treating surgical wounds The term "primarily includes" as used herein refers to fragments in which although some level of other biological activity may remain, that activity is reduced as compared with full-length fragments, whereas the activity that is considered "primary" remains at about the same or an increased level as that observed in the full-length native protein. Similarly, the term "primarily excludes" as used herein refers to fragments in which although some level of a particular biological activity may remain, the level of that particular activity is reduced (optionally significantly and/or statistically significantly reduced) as compared with full-length fragments, whereas one or more other biological activities remains at about the same or increased level as that observed in the full-length native protein.

In some embodiments involving selection of biologically active fragments, the methods include assessing changes in the level of expression of one or more biological activities, including increases and decreases of one or more activities in a selected fragment are assessed as changes in reference to the activities observed in the full-length protein. In some embodiments, one or more biological activities are being selected to remain the same as that observed in the full-length fragments while other activities may be increased or decreased or even eliminated (e.g., such fragments would lack one or more of the activities discussed). In some embodiments, the change is an increase as compared to another level, and in some embodiments the change is a decrease as compared to another level. In some embodiments, the detectable change (increase or decrease) is statistically significant. In some embodiments, such changes can be assessed quantitatively as at least about a 5%, 10%, 25%, 50%, 100%, 200%, 500% or greater change, and/or about a 5-10%, 10-25%, 10-50%, 25-50%, 50-75%, 50-100%, 100-150%, 100-200%, 200-300%, 300-500%, or 500-1000% change. In some embodiments, an activity that "remains the same" can still be observed to have some change from the activity of the full-length protein, but such change might be limited to, for example, about a 1%, 2%, 5%, 10%, or 20% change or less.

In a non-limiting example, fragments of interest may include those that primarily mediate the anti-inflammatory effect of Smad7. Smad7 peptides having this anti-inflammatory function may be sufficient and optionally an improvement for treating chronic inflammation associated conditions, such as but not limited to, oral mucositis, stomatitis and psoriasis, among others. In another non-limiting example, fragments of interest may include those that primarily mediate cell migration and/or blocking TGF-β-induced growth arrest and/or fibrotic response. Smad7 peptides having this cell migration and proliferation function may be sufficient, and optionally an improvement, for enhancing healing that is not associated with excessive inflammation. Types of wounds that might benefit from this form of treatment include, but are not limited to, surgical wounds, fibrotic scarring, and diabetes wounds, defective healing and/or scarring among others.

G. Methods of Producing Smad7 Protein

In another aspect, methods for producing Smad7 protein, including any of the Smad7 variants, fragments, truncations, fusion proteins (e.g., PTD-Smad7) described herein are contemplated. The inventors have discovered methods of producing Smad7 protein at levels and purity sufficient for research, development, or commercialization that include nucleic acid codon optimization. As a result, methods for producing Smad7 including the use of one or more of the codon-optimized Smad7 nucleic acid molecules described herein (e.g., within the Examples) are expressly contemplated.

EXAMPLES

The following examples are included to illustrate various embodiments. It should be appreciated by those of skill in the art that the techniques disclosed in the examples that follow represent techniques discovered to function well in the practice of the claimed methods, compositions and apparatus. However, those of skill in the art should, in light of the present disclosure, appreciate that many changes may be made in the specific embodiments which are disclosed and still obtain a like or similar result without departing from the spirit and scope of the present technology.

Example 1

K5.Smad7 Mice are Resistant to Oral Mucositis

Figure 7:
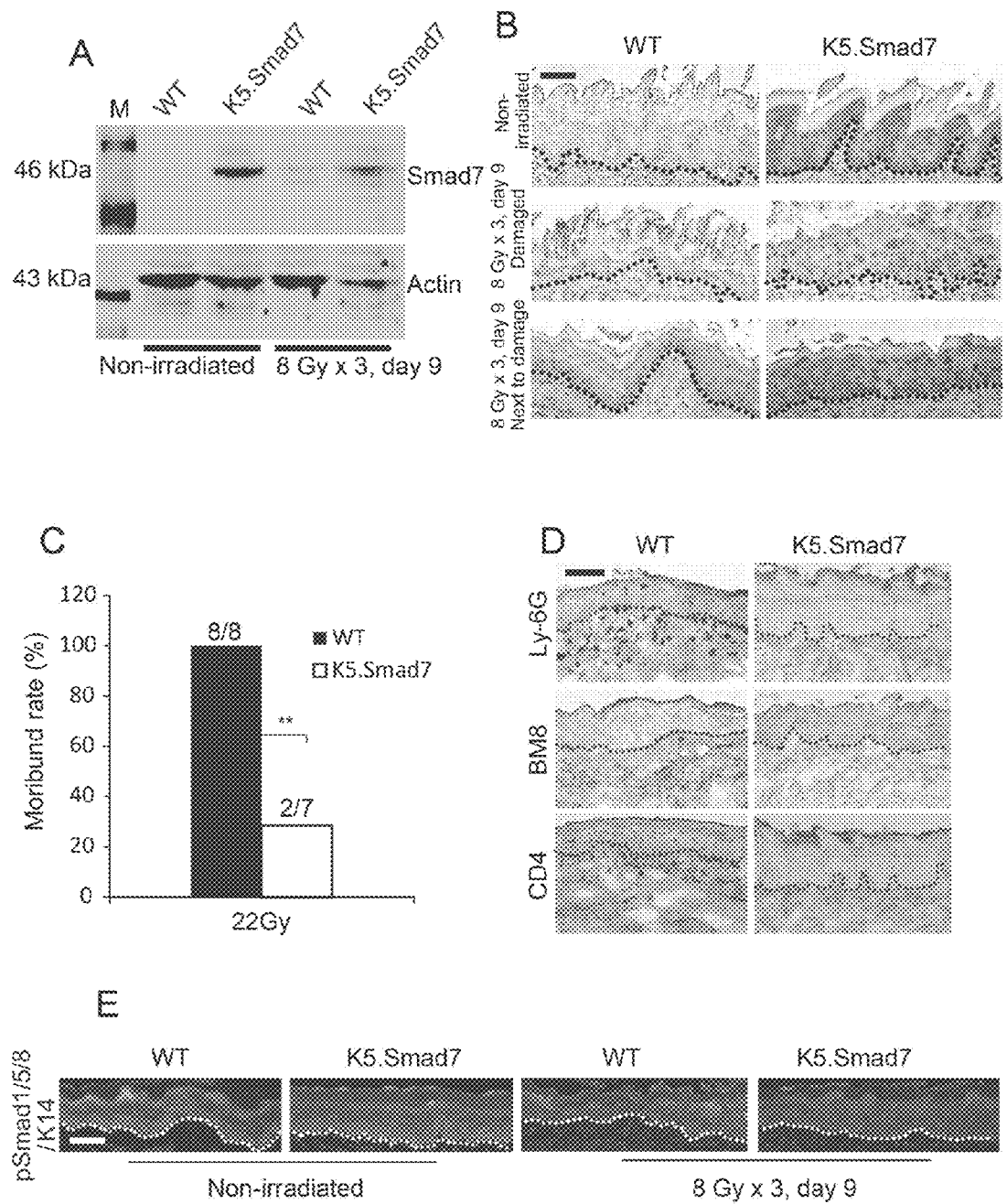
FIGS. 7A-E provide an illustrative embodiment of data showing K5.Smad7 oral mucosal tissues were resistant to radiation-induced oral mucositis.

A transgenic mouse model expressing a human Smad7 protein in keratinocytes (K5.Smad7) was generated as previously described (Han et al., *Dev. Cell*, 11:301-312, 2006). Transgene expression in oral epithelia was confirmed (FIGS. 7A-B). The mice were bred into in the C57BL/6 background, and 8-10 weeks old male and female transgenic mice and wild-type littermates were used in studies. These mice showed improved healing of excisional skin wounds (Han et al., *Am. J. Pathol.*, 179:1768-1779, 2011) and radiation-induced oral mucositis.

K5.Smad7 mice and wild-type littermates were exposed to cranial radiation to determine the biological equivalent dose (BED) required to induce oral mucositis in mice. It was determined that 8 Gy×3 (BED=43.2), a regimen relevant to hypo-fractionated radiotherapy in clinic, was the minimal dose needed to induce oral mucositis (FIGS. 1A-B). To evaluate the potency of Smad7 effects, they also tested single doses of cranial radiation and found that oral mucositis severity correlated with BED values between 18 Gy (BED=50.4) and 22 Gy (BED=70.4) (FIGS. 1A-B, FIG. 7C). By day 9 after initiation of radiation, wild-type mice developed oral ulcers (FIGS. 1A-B).

K5.Smad7 oral mucosa prior to irradiation had morphology similar to wild-type mice, but exhibited resistance to radiation-induced oral mucositis (FIGS. 1A-B). Histological analyses revealed that wild-type mice developed oral mucositis (FIG. 1A) similar to that in humans (FIG. 1C). The First Affiliated Hospital of Kunming Medical University, China provided de-identified archived human tissue paraffin sections and approved the study as an exempt for human subjects. Oral mucositis lesions were from the tongue, buccal or oropharyngeal mucosa adjacent to recurrent oral cancers that had undergone radiotherapy. Non-irradiated oral mucosa sections were from surgically removed sleep apnea oral tissues and a tongue biopsy adjacent to a cyst (mucocele).

K5.Smad7 oral epithelia typically showed radiation dose-dependent damage, i.e., thinning epithelium and flattened tongue papillae after 8 Gy×3 radiation, and more damaged (hypo- or hypertrophic) epithelial cells after 18 Gy and 22 Gy radiation (FIG. 1A). Consistent with increased leukocyte infiltration in human oral mucositis lesions (FIG. 1C), lesions in wild-type mice harbored numerous infiltrated leukocytes (FIGS. 1D-E) consisting of neutrophils, macrophages, and lymphocytes (FIG. 7D); all were substantially reduced in K5.Smad7 oral mucosa (FIGS. 1D-E and 7D).

Because it is difficult to capture human oral mucositis pathology at the acute phase, a mouse model was utilized to assess proliferation and apoptosis when ulcers are just formed. Similar to previous reports, proliferative cells were sparse in irradiated wild-type oral epithelium, but were seen more in irradiated K5.Smad7 oral epithelium (FIGS. 1D and 1F). Conversely, apoptotic cells were significantly reduced in irradiated K5.Smad7 oral mucosa compared to wild-type mice (FIGS. 1D and 1G).

Figure 2:
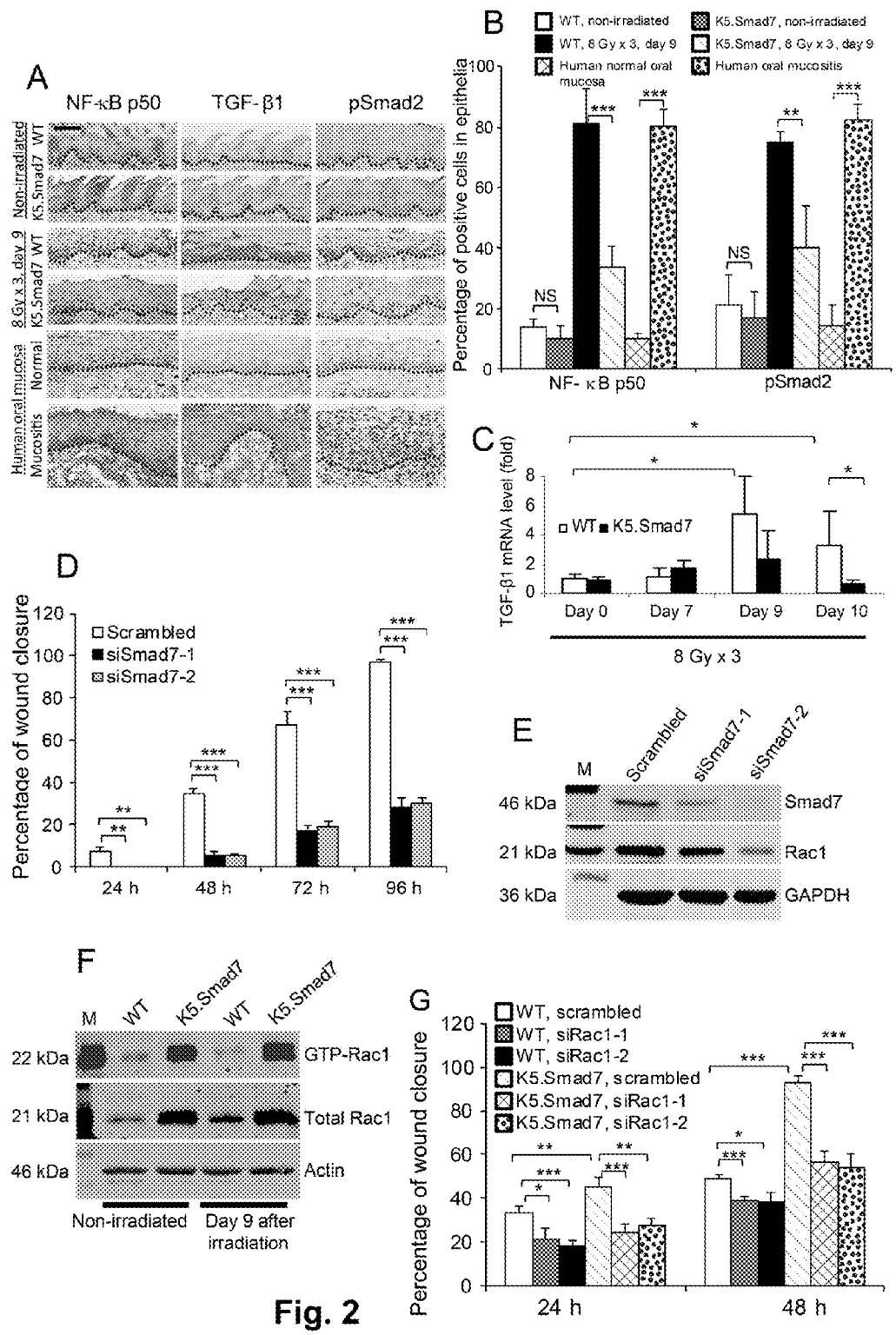
FIGS. 2A-G provide an illustrative embodiment of data showing molecular alterations attenuated by Smad7.

As expected, cells with nuclear NF-κB p50 subunit were significantly increased in oral mucositis compared to non-irradiated wild-type oral mucosa (FIGS. 2A-B). Interestingly, TGF-β1, an immune suppressant in internal organ, but pro-inflammatory in oral mucosa, together with its activated signaling mediator, phosphorylated (p) Smad2, were also increased in oral mucositis compared to non-irradiated oral mucosa in wild-type mice (FIGS. 2A-B). Similar changes were also detected in human oral mucositis lesions (FIGS. 2A-B).

Irradiated K5.Smad7 oral epithelia significantly reduced cells positive for nuclear NF-κB p50 and pSmad2, even though they still had abundant TGF-β1 protein (FIGS. 2A-B). TGF-β1 mRNA in irradiated wild-type oral mucosa was significantly increased on day 9 and day 10 (FIG. 2C). TGF-β1 mRNA level in K5.Smad7 mucosa was similar to wild-type mucosa at earlier time points, but was back to normal by day 10 (FIG. 2C). Although not wishing to be bound by any theory, these data suggest that TGF-β1 transcription is not inhibited by Smad7, but its more rapid decline in K5.Smad7 mucosa could be a consequence of accelerated healing.

Phospho-Smad1/5/8, markers for activated BMP signaling, were not affected by Smad7 before and after radiation (FIG. 7E). This result is consistent with the ability of Smad7 to preferentially inhibit TGF-β signaling.

Example 2

Rac1 Contributes to Smad7-Mediated Keratinocyte Migration

Figure 8:
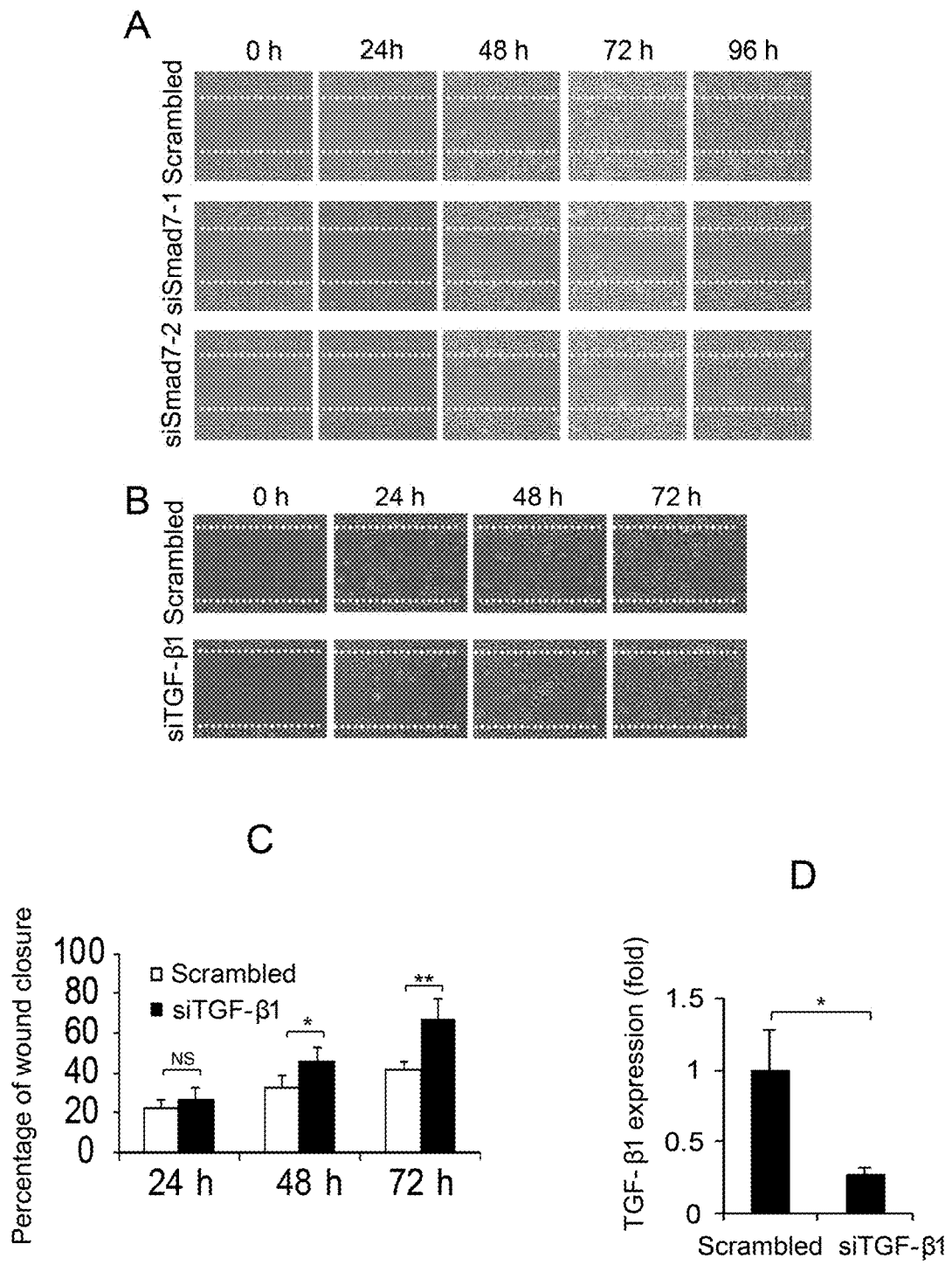
FIGS. 8A-D provide an illustrative embodiment of data showing migration in spontaneously immortalized human oral epithelial cells (NOK-SI) was delayed by knocking down Smad7 but accelerated by knocking down TGF-β1.

To determine if Smad7 contributes to healing in human oral keratinocytes, Smad7 was knocked down in spontaneously immortalized human oral keratinocytes (NOK-SI) Smad7 knockdown blunted keratinocyte migration after wounding (FIG. 2D and FIG. 8A). Conversely, knocking down TGF-β1 accelerated keratinocyte migration (FIGS. 8B-8D), consistent with accelerated wound healing seen in mice null for TGF-β1 or Smad3.

To search for molecular mechanisms associated with Smad7-mediated keratinocyte migration, Rac1, a protein indispensable for oral wound healing was examined Rac1 was reduced after Smad7 knockdown (FIG. 2E). It was expected that TGF-β1 overexpression in oral mucositis would activate Rac1 through a Smad-independent mechanism. However, although total Rac1 protein increased by 2-fold after irradiation, activated Rac1 protein did not change considerably in wild-type tongues (FIG. 2F).

Figure 9:
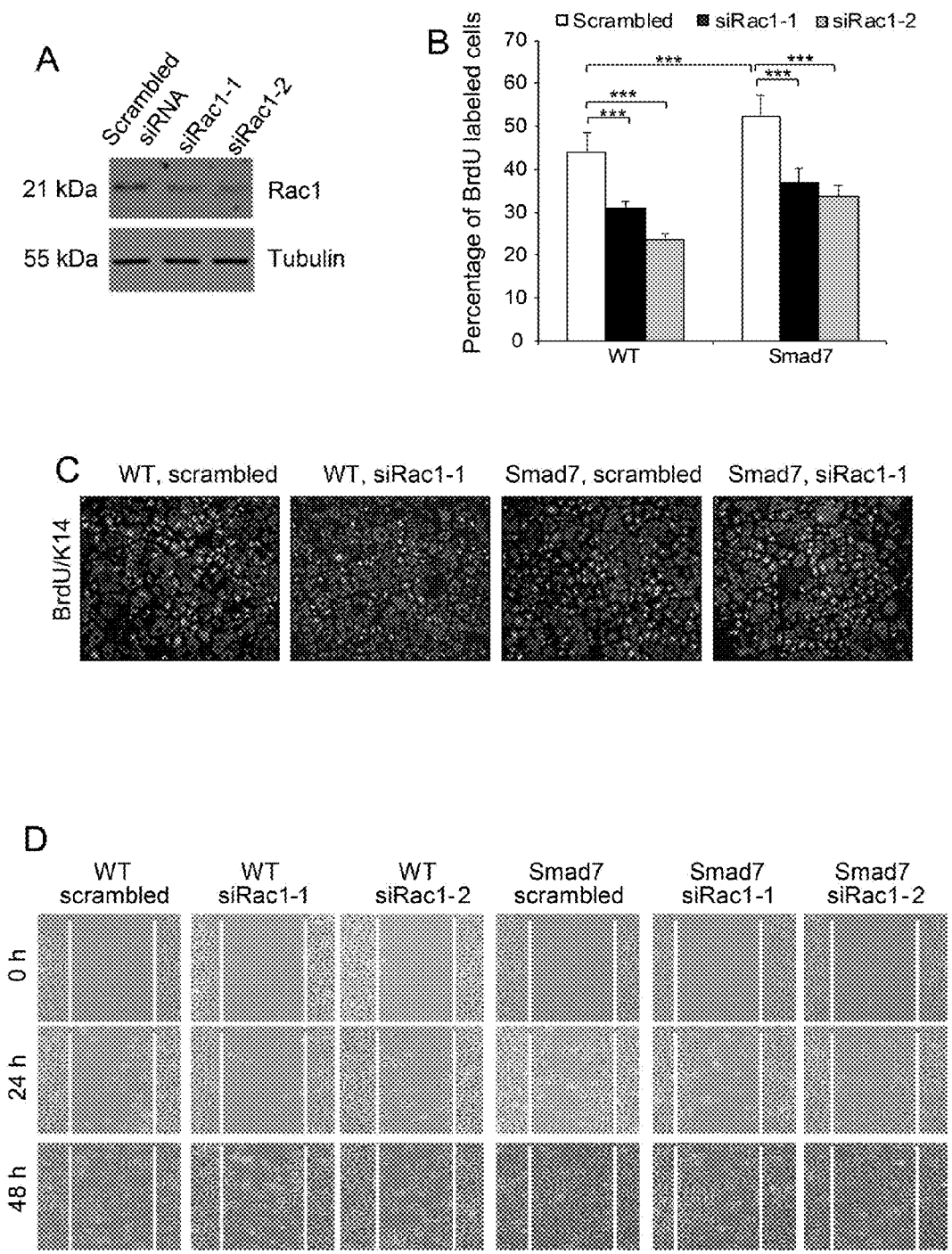
FIGS. 9A-D provide an illustrative embodiment of data showing knocking down Rac1 reduced proliferation and migration of wild-type (WT) and Smad7 transgenic keratinocytes.

In K5.Smad7 oral mucosa, both total and activated Rac1 were significantly increased by 4-fold and 8-fold, respectively, compared to wild-type oral mucosa (FIG. 2F). To determine the functional significance of Smad7-induced Rac1 activation, Rac1 was knocked down in primary keratinocytes isolated from wild-type and Smad7 transgenic neonatal skin, and assays for cell proliferation and migration were performed. Rac1 knockdown showed modestly reduced proliferation in wild-type and Smad7 keratinocytes (FIGS. 9A-9C), but almost completely abrogated Smad7-induced migration (FIG. 2G and FIG. 9D), suggesting that increased Rac1 contributes to Smad7-mediated cell migration.

Figure 10:
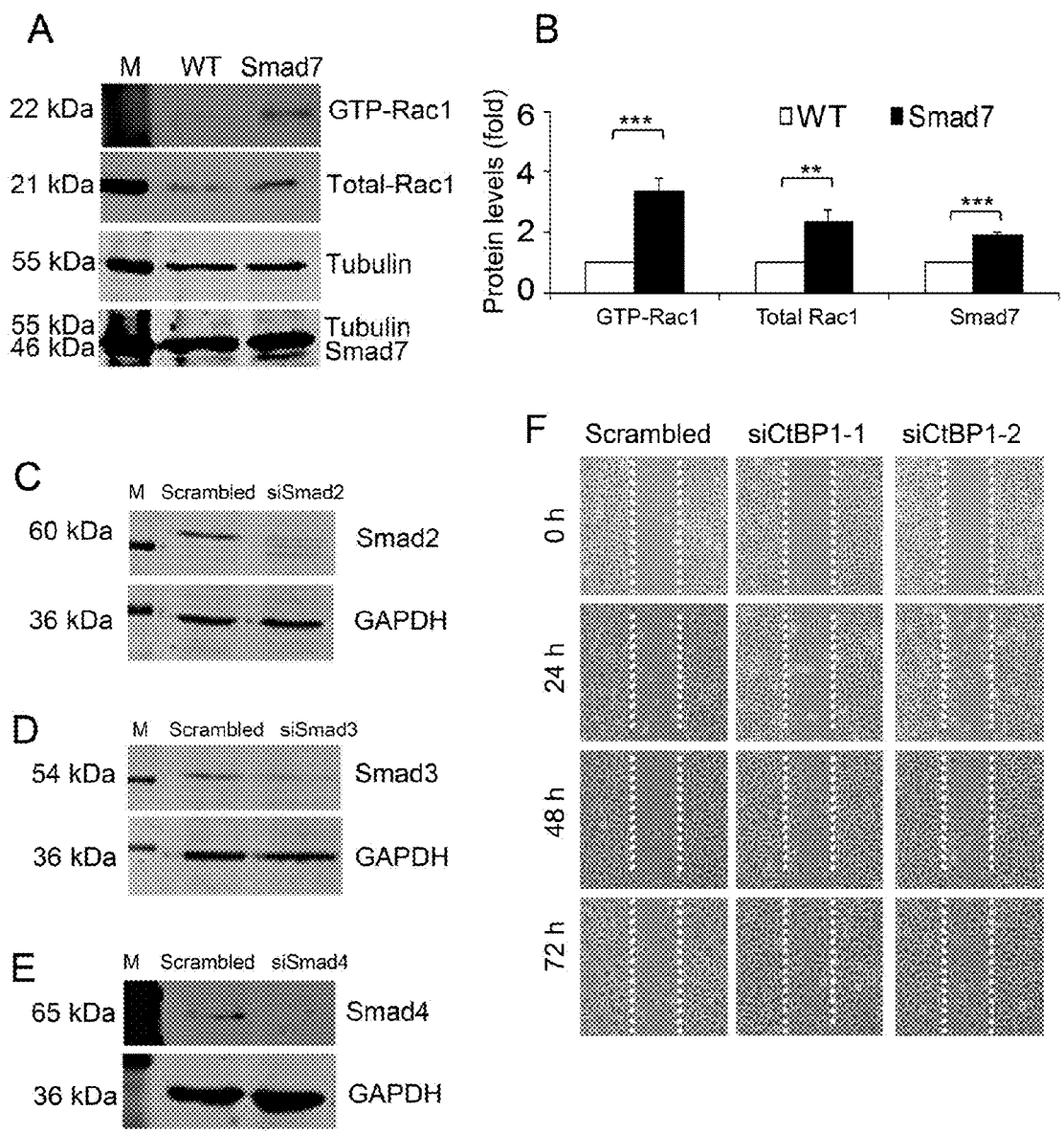
FIGS. 10A-F provide an illustrative embodiment of data showing Smad7 increased Rac1 expression by repressing Smad and CtBP1 binding to the SBE of the Rac1 promoter.

It was observed that increased Rac1 mRNA levels in Smad7 transgenic keratinocytes correlated with total and active Rac1 protein levels (FIGS. 3A-B and FIGS. 10A-B), suggesting that increased Rac1 activation in Smad7 keratinocytes is, at least in part, a consequence of increased Rac1 transcripts. Further, Rac1 protein increased by ~3-fold (FIG. 3C) after knockdown of individual Smads in NOK-SI cells (FIGS. 10C-10E). These data suggest that normal Smad signaling represses Rac1 transcription.

Figure 3:
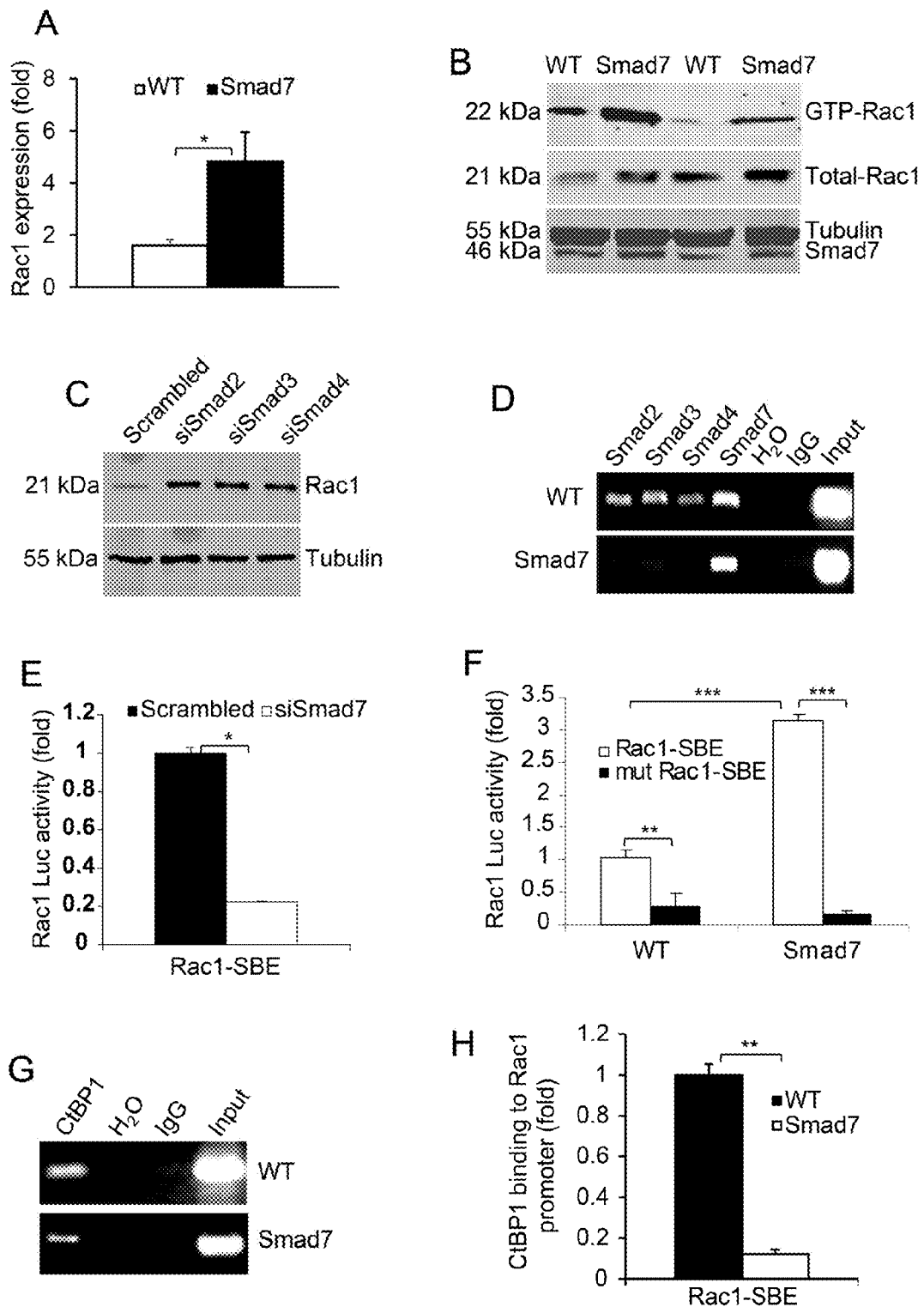
FIGS. 3A-H provide an illustrative embodiment of data showing Smad7 increased Rac1 expression by repressing individual Smad and CtBP1 binding to the SBE of the Rac1 promoter.

Among the two putative Smad binding elements (SBEs) in the mouse Rac1 promoter (−2.1 Kb and −1.5 Kb upstream of the coding sequence), which are in similar regions of the human Rac1 promoter, chromatin immunoprecipitation (ChIP) identified Smad-2, -3, -4, and -7 binding to the −1.5 Kb site (FIG. 3D), but not the −2.1 Kb site in wild-type keratinocytes; binding of Smad-2, -3 and -4 was significantly reduced in Smad7 transgenic keratinocytes (FIG. 3D).

Luciferase reporter assays using a SBE-containing Rac1-Luc construct show that knockdown of Smad7 in wild-type keratinocytes significantly reduced luciferase activity (FIG. 3E). Conversely, Smad7 transgenic cells had increased luciferase activity compared to wild-type cells, and mutating the SBE attenuated this increase (FIG. 3F). Thus, Smad7 binding to SBE appears necessary to expel signaling Smads to abrogate Rac1 repression.

Among known Smad transcriptional co-repressors, it was found that CtBP1 bound to the Rac1 promoter SBE-1.5 Kb site in wild-type keratinocytes (FIG. 3G), and Smad7 transgene expression significantly reduced CtBP1 binding to the SBE (FIGS. 3G-H). When CtBP1 was knocked down in NOK-SI cells, Rac1 protein and Rac1-Luc activity were increased compared to keratinocytes transfected with scrambled siRNA (FIGS. 4A-B), suggesting that CtBP1 binding to SBE-1.5 Kb represses Rac1 expression. Further, knocking down CtBP1 in NOK-SI cells increased their migration (FIG. 4C and FIG. 10F).

Figure 4:
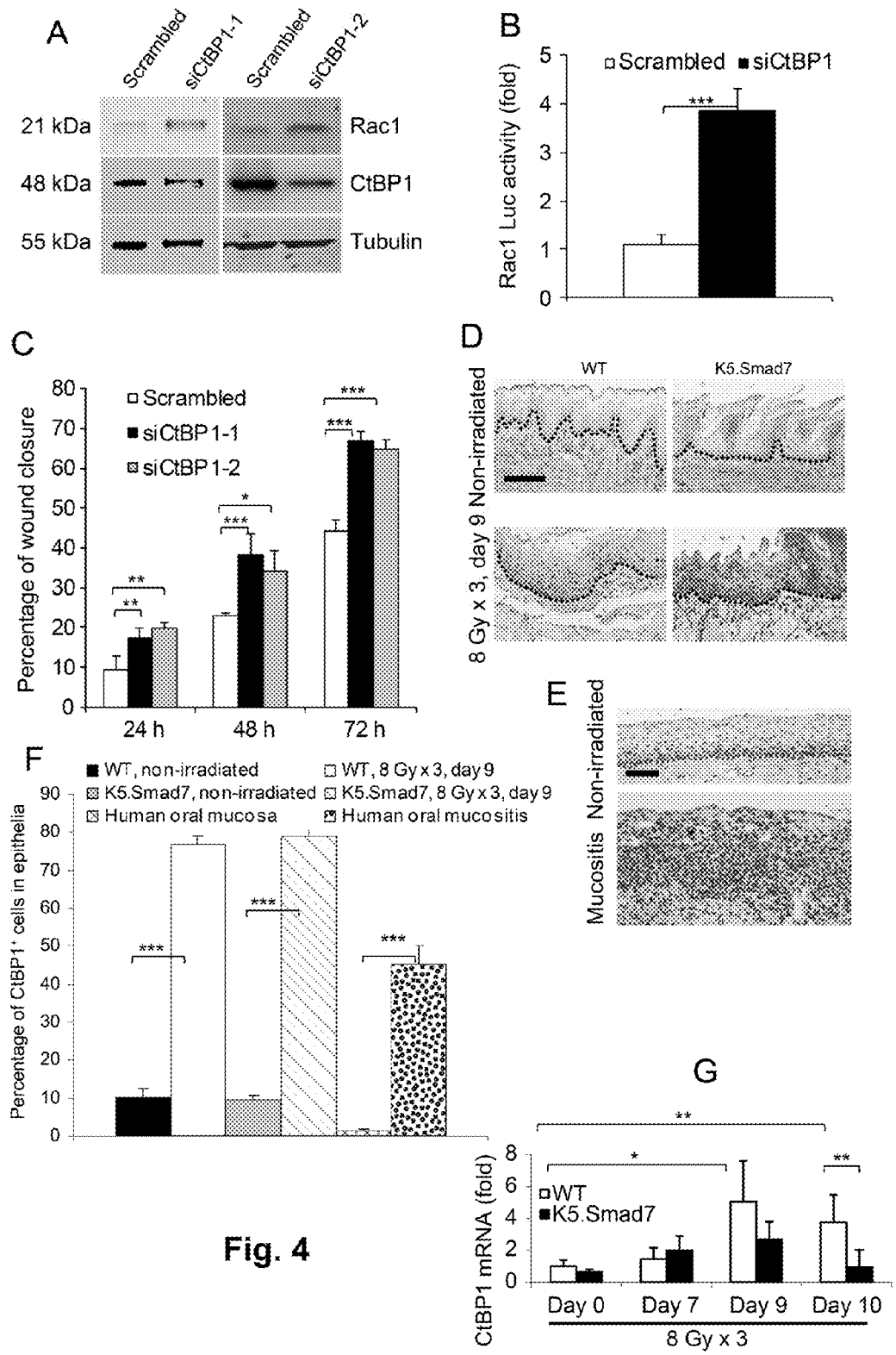
FIGS. 4A-G provide an illustrative embodiment of data showing CtBP1-associated Rac1 repression contributed to inhibition of keratinocyte migration.

Upon examination of CtBP1 protein in radiation-induced oral mucositis, it was found that CtBP1 is barely detectable in non-irradiated mouse and human oral mucosa (FIGS. 4D-4F); however, CtBP1 positive cells were significantly increased in irradiated oral mucosa of wild-type and K5.Smad7 mice as well as in human oral mucositis (FIGS. 4D-4F). Additionally, CtBP1 mRNA in irradiated wild-type oral mucosa was significantly increased on day 9 and day 10 (FIG. 4G). CtBP1 mRNA level in K5.Smad7 mucosa was similar to wild-type mucosa at earlier time points, but declined to normal by day 10 (FIG. 4G). These results indicate that Smad7 does not reduce CtBP1 mRNA but instead inhibits CtBP1 binding to the Rac1 promoter by repelling the Smad/CtBP1 complex from the SBE binding site; further, more rapid CtBP1 reduction in K5.Smad7 mucosa serves as a marker of healing.

Example 3

Tat-Smad7 Alleviates Radiation-Induced Oral Mucositis

Smad7 transgene's ability to block multiple pathological processes of oral mucositis prompted us to explore if localized Smad7 delivery can be used to prevent and treat oral mucositis. Because Smad7 is a nuclear protein, local Smad7 delivery needs to allow Smad7 to rapidly enter into cells before saliva washes off the protein. Thus, a recombinant human Smad7 with an N-terminal Tat-tag allowing proteins to rapidly permeate the cell membrane and enter the nucleus was produced. A V5 epitope was added to the C-terminal end of the Tat-Smad7 protein to track Tat-Smad7 cell penetration (FIGS. 11A-11D).

Figure 11:
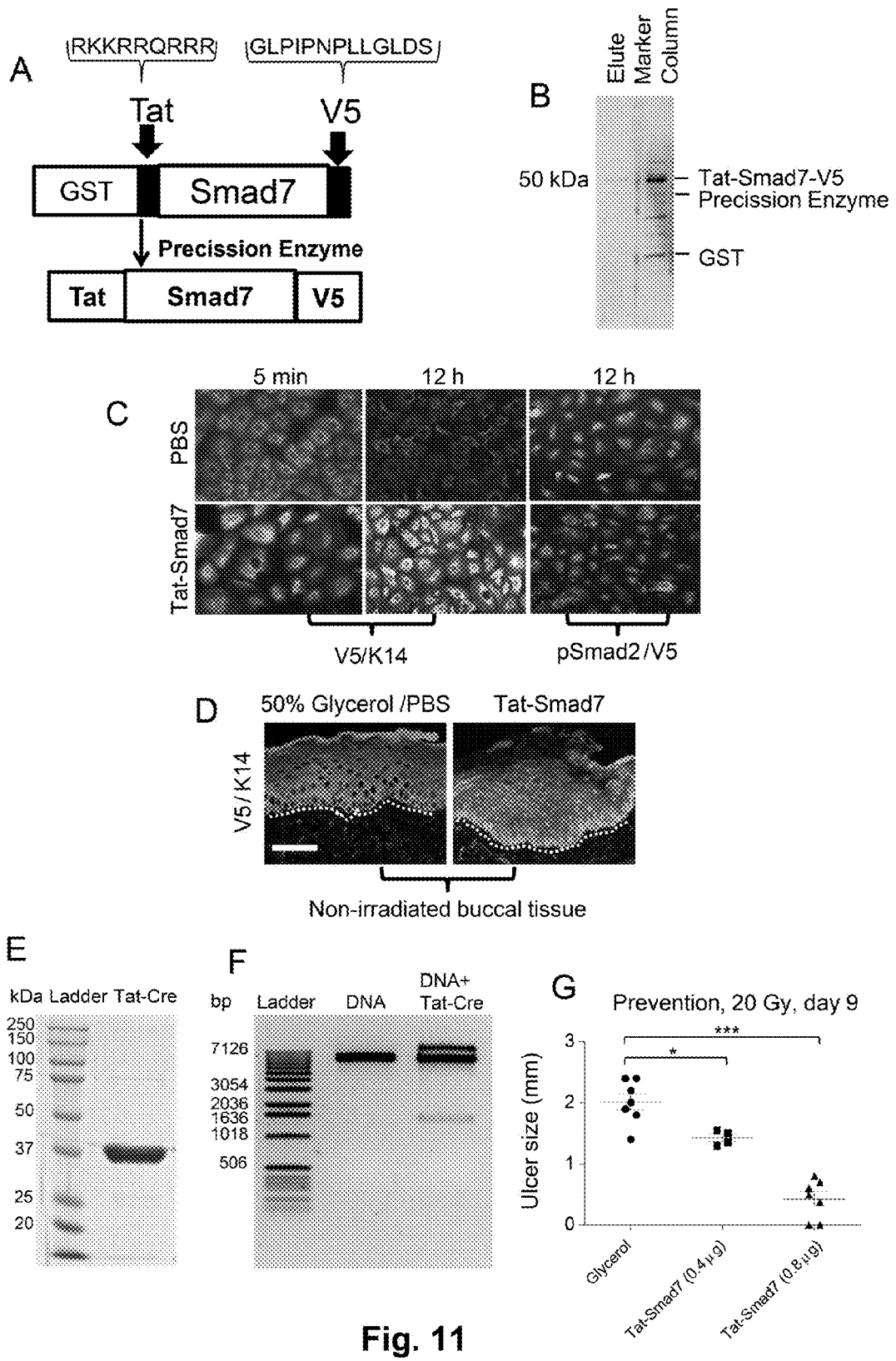
FIGS. 11A-G provide an illustrative embodiment of data showing the purification and characterization of Tat-Smad7 and Tat-Cre proteins.
Figure 12:
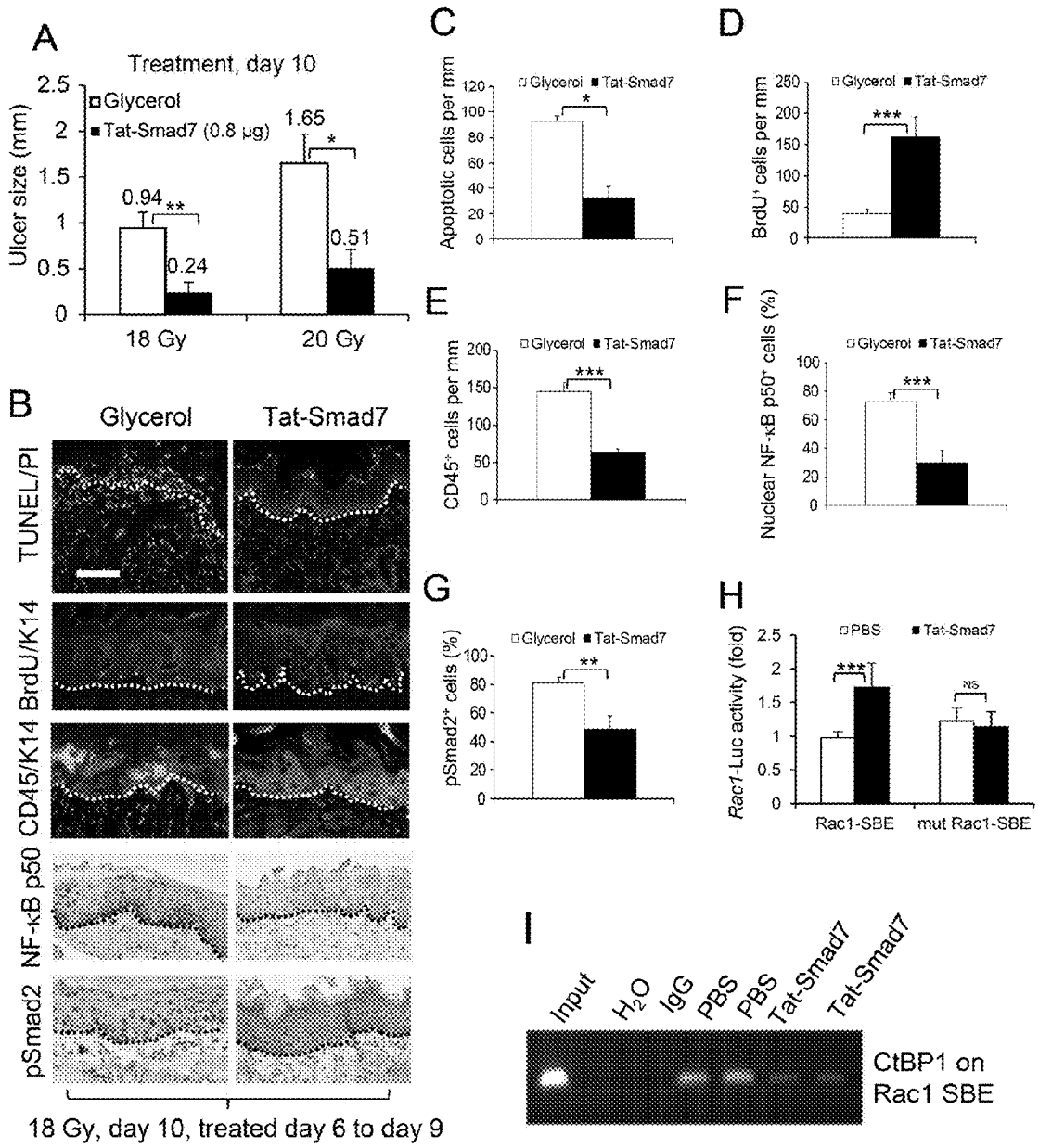
FIGS. 12A-I provide an illustrative embodiment of data showing effects of Tat-Smad7 treatment on oral mucositis.

Using its ability to block Smad2 phosphorylation, Tat-Smad7 bioactivity was tested (FIG. 11C). Tat-Cre recombinant protein with the same tags as a control (FIGS. 11E-F) was produced, and cloned into the pET101-Topo protein expression vector (Invitrogen) that contains a sequence encoding C-terminal 6×His (SEQ ID NO: 40). Tat-Cre was transformed into BL-21 STAR™ E. coli (Invitrogen) to produce Tat-Cre protein and was purified with Ni-NTA column.

The purity and size of both proteins was verified using SDS-PAGE electrophoresis. To evaluate transduction and activity of Tat-Smad7 protein in vitro, Tat-Smad7 was added to primary mouse keratinocytes. Slides were fixed in cold methanol for 5 minutes and stained for V5 and pSmad2. Tat-Cre activity was verified by digesting a 1,460 bp floxed fragment from the 7,650 bp vector pLL3.7 (Addgene). For in vivo treatments, 30 µL 50% glycerol/PBS as a vehicle control and Tat-Cre as a non-irrelevant protein control were used. Tat-Smad7 or Tat-Cre (in 30 µL 50% glycerol/PBS, doses and regimens are specified in each figure) was topically applied to mouse oral cavity and mice were restricted from oral intake for 1 hour.

For oral mucositis prevention, both Tat-Smad7 and Tat-Cre (in 50% glycerol/PBS) were topically applied to the oral cavity of 8-10 week old C3H females (Jackson Laboratory) or C57BL/6 mice daily, starting 24 hours prior to radiation through day 8 after initiation of radiation. Treated tissues were examined on day 9. Mouse tongues were harvested, fixed in 10% formalin, embedded in paraffin, and cut into 5 µm sections. Histological changes were analyzed and ulcers were measured using H&E stained slides. An additional group received Palifermin treatment with a clinical regimen, i.e., 6.25 mg kg$^{-1}$ (i.p.) daily for 3 days prior to irradiation, and daily for 3 days 24 hours after the last dose of radiation.

Figure 5:
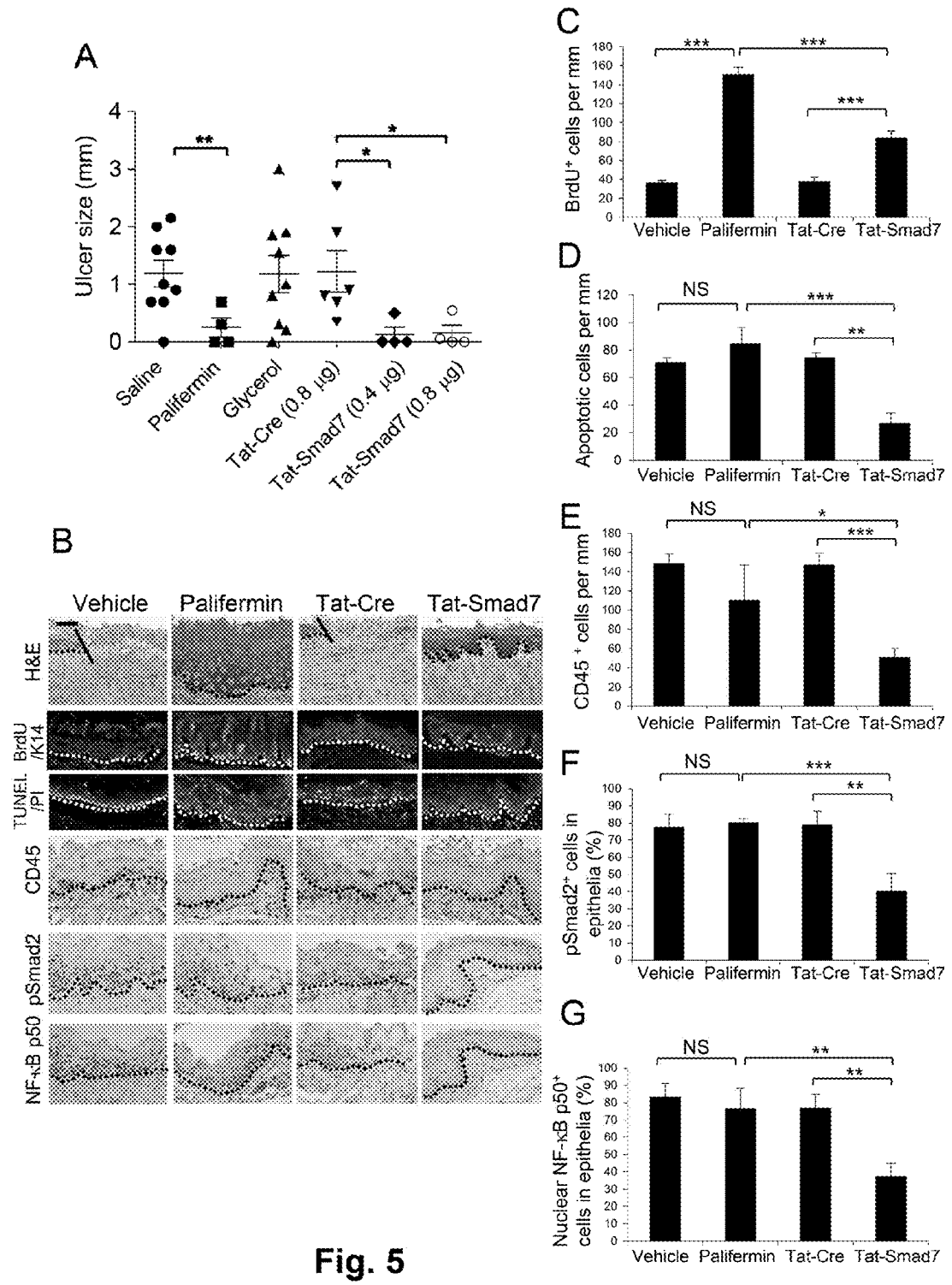
FIGS. 5A-G provide an illustrative embodiment of data showing oral Tat-Smad7 application prevented radiation-induced oral mucositis in mice.

Tat-Cre showed no effect compared to vehicle controls (FIGS. 5A-B). Tat-Smad7 treatments showed preventive effects on ulcer formation similar to Palifermin (FIG. 5A). The dose-dependent effect of Tat-Smad7 was more obvious when used on animals given a 20 Gy (BED=60) single dose of radiation that induced larger oral ulcers than fractionated radiation (FIG. 11G). Microscopically, both Palifermin and Tat-Smad7 treated oral mucosa prevented open ulceration in the majority of cases (FIG. 5B). Palifermin-treated mucosa exhibited more keratinocyte down-growth but also more damaged keratinocytes (condensed or charcoal-like nuclei, swelled mono- or multi-nucleated cells and shattered nuclear fragments in conified layers) than Tat-Smad7-treated mucosa (FIG. 5B). Immunostaining revealed that Palifermin increased proliferation more significantly than Tat-Smad7. Tat-Smad7 reduced apoptosis, leukocyte infiltration, nuclear pSmad2 and NF-κB p50, but Palifermin did not (FIGS. 5B-5G).

Figure 6:
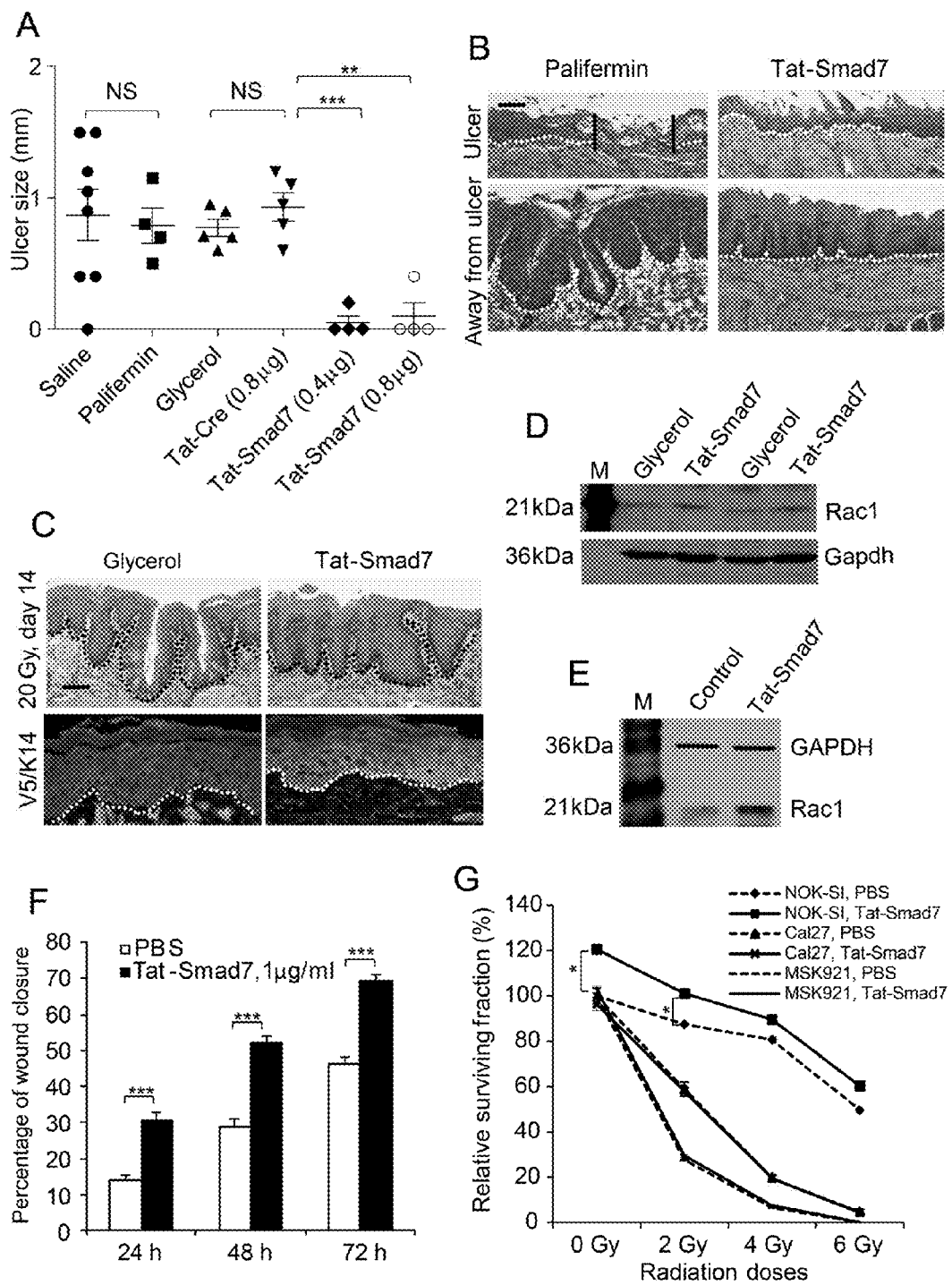
FIGS. 6A-G provide an illustrative embodiment of data showing Tat-Smad7 treatment on oral mucositis.

To test whether Tat-Smad7 can be used to treat existing oral mucositis, mice were exposed to fractionated (8 Gy×3) cranial radiation and Tat-Smad7 (topically) or Palifermin (6.25 mg kg$^{-1}$, i.p.) was applied daily from day 6 after initiation of radiation (when mucosal damage was obvious) till day 9. Treated tissues were examined on day 10. Although beginning post-radiation administration of Palifermin at earlier time points than the current protocol reduced oral mucositis in mice, Palifermin administration with the current protocol did not accelerate ulcer closure (FIG. 6A), regardless of its hyperproliferative effect on the entire oral mucosa (FIG. 6B). This is not surprising, as Palifermin is approved to prevent but not treat oral mucositis.

Tat-Smad7 treated oral mucositis reduced ulcer sizes and pathological alterations after both fractionated and single dose radiation (FIGS. 6A-B and FIGS. 12A-12G). Away from ulcers, Tat-Smad7 treated oral mucosa exhibited less hyperplasia and more differentiated epithelia than Palifermin-treated oral mucosa (FIG. 6B). With a 20 Gy single dose radiation that caused slower healing than fractionated radiation, the effect of Tat-Smad7 on recovery after wound closure was more obvious. When vehicle treated ulcer was just re-epithelialized, Tat-Smad7 treated mucosa had almost recovered to normal morphology (FIG. 6C).

Consistent with observations in K5.Smad7 mice, Tat-Smad7 increased Rac1 promoter activity and reduced CtBP1 binding to the SBE of the mouse Rac1 promoter (FIGS. 12G and 12I), and increased Rac1 protein in mouse oral mucositis and human oral keratinocytes (FIGS. 6D-E).

Figure 13:
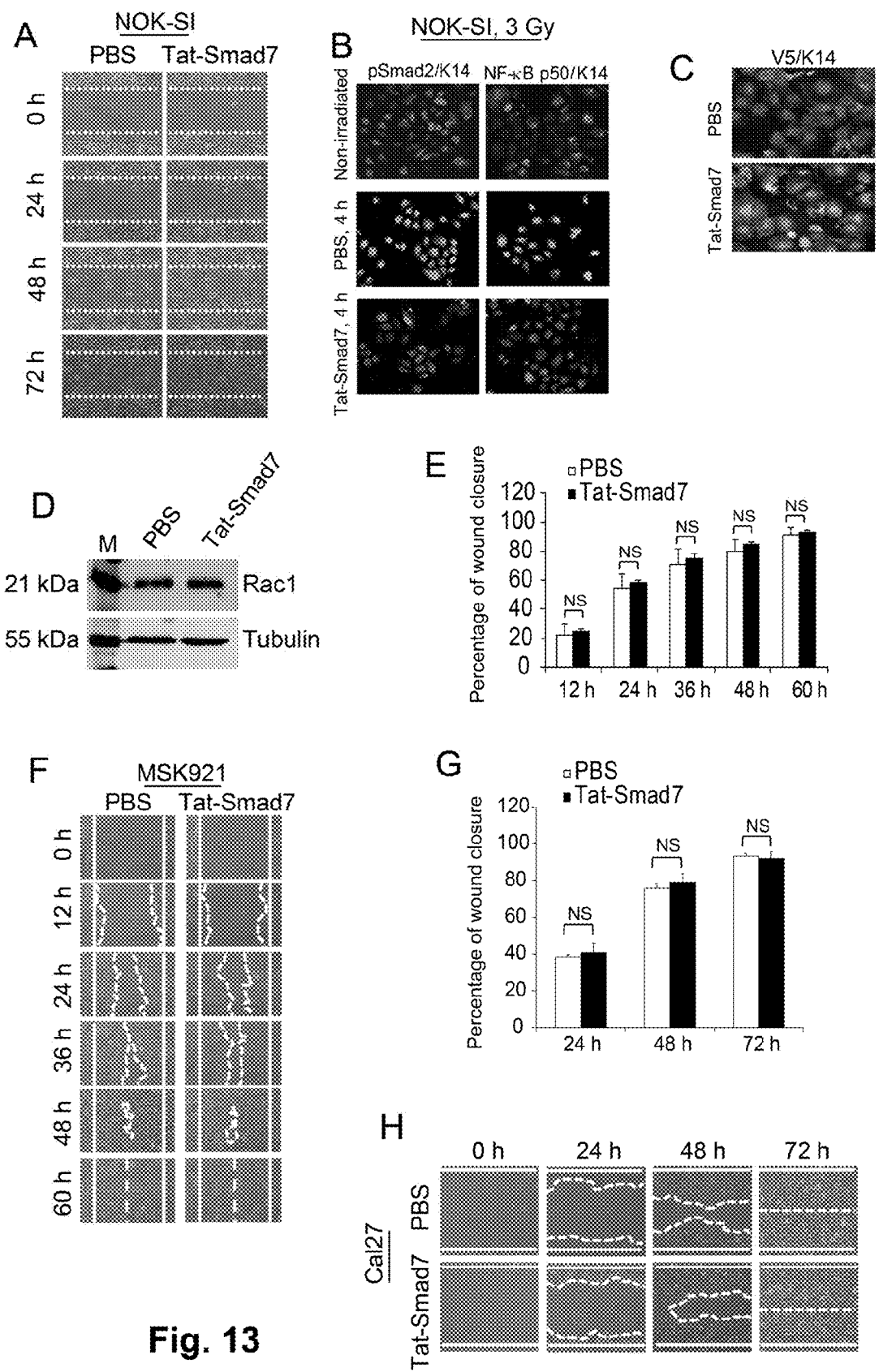
FIGS. 13A-H provide an illustrative embodiment of data showing effects of Tat-Smad7 treatment on migration of human keratinocytes and tumor cell lines.

Tat-Smad7-treated human oral keratinocytes after wound scratch had accelerated wound closure (FIG. 6F and FIG. 13A). Further, irradiated human oral keratinocytes increased nuclear pSmad2 and NF-κB p50, which were attenuated by Tat-Smad7 treatment (FIG. 13B). In contrast, although Tat-Smad7 penetrated oral cancer cells efficiently (FIG. 13C), it did not further elevate Rac1 protein level that is already abundant in cancer cells (FIG. 13D). This result could account for faster migration of cancer cells than normal keratinocytes (FIG. 6F and FIGS. 13A, 13E-13H), and the lack of an effect of Tat-Smad7 on migration in two oral cancer cell lines: MSK921 which does not contain genetic loss of TGF-β signaling components; and Cal27 which has a mutated Smad4 (FIGS. 13E-13H).

Colony assays show that survival of human oral keratinocytes was slightly increased by Tat-Smad7 treatment with or without radiation (FIG. 6G). Consistent with the notion that reduced survival after irradiation is more prominent in cancer cells than in normal cells, SCC cells showed substantial reductions in cell survival after radiation. Treatment with Tat-Smad7 did not affect survival in SCC cells with or without radiation (FIG. 6G).

Example 4

Design of a Cell-Penetrating Smad7 Protein

It was hypothesized that in order to be effective as a therapeutic, SMAD7 needed to be able to penetrate cells effi-ciently. In order to achieve this, the Smad7 sequence was modified to include a protein transduction domain.

The Tat sequence from HIV was selected to test with Smad7 as a protein transduction domain. The nucleotide and protein sequences of Tat that were used in fusion proteins with Smad7 and Smad7 fragments are derived from Cardarelli et al., *Traffic Apr* 9(4):528-39 (2008). The Tat nucleotide and amino acid sequences are provided below:

```
ggccgtaaaaaacgccgtcaacgccgccgt (SEQ ID NO: 1)

G R K K R R Q R R R         (SEQ ID NO: 2)
```

Fusion proteins were prepared having Tat directly linked in frame to human Smad7 complementary DNA (cDNA) either at the 5' or 3' ends of Smad7 as shown below:

```
                                          (SEQ ID NO: 7)
5' Tat:     Ggccgtaaaaaacgccgtcaacgccgccgt
            -Smad7

(SEQ ID NO: 8)
3' Tat:     Smad7-Ggccgtaaaaaacgccgtcaacgccgccgt
```

The 5' Tat-Smad7 construct included a 3' V5 tag sequence, and was cloned into the pGEX-6p-1 protein expression vector (New England Biolabs) to make a GST-Tat-Smad7 fusion protein. Tat-Smad7 gene was transformed into BL-21 Star *Escherichia coli* (Invitrogen) to produce Tat-Smad7 protein. The protein was purified by glutathione column purification and elution, using enzymatic cleavage from the Glutathione S Transferase (GST) fusion (Precision enzyme, GE Life Sciences).

While creating a PTD-Smad7 fusion protein, a V5 tag at the 3' end was included to monitor Tat-Smad7 penetration into cells by immunostaining using a V5 antibody. This epitope tag can be deleted for use in the clinic (e.g., by re-cloning the sequence in the absence of the V5 tag), if appropriate.

A PTD-Smad7 fusion protein (Tat-Smad7-V5-6H) ("6H" disclosed as SEQ ID NO: 40) was also created having a 6-Histidine (6-H) tag (SEQ ID NO: 40) for protein purification, and is shown below. Tat-Smad7-V5-6H ("6H" disclosed as SEQ ID NO: 40) has the following nucleotide sequence: 1-53 include the 5' sequence of pET-TOPO; 54-1365 include Tat-Smad7; 1366-1497 include 3' pET-TOPO containing the V5 epitope and 6×His tag (SEQ ID NO: 40) (V5 includes 1393-1434, His tag includes 1444-1461, and the Stop includes 1462-1464).

Tat-human Smad7, codon-optimized for protein production, cloned to pET101/D-Topo vector is shown below:

```
ttcccctctagaaataattttgtttaactttaagaaggaattcaggagcccttcaccatg

M cgtaaaaaacgccgtcaacgccgccgtggtttccgtacgaaacgctcggccctggtccgt

R  K  K  R  R  Q  R  R  R  G  F  R  T  K  R  S  A  L  V  R cgcctgtggcgctcccgtgctccgggtggtgaagatgaagaagaaggtgctggcggcggt

R  L  W  R  S  R  A  P  G  G  E  D  E  E  E  G  A  G  G  G ggcggtggcggtgaactgcgtggcgagggtgcaaccgatagtcgtgcacacggtgcaggc

G  G  G  G  E  L  R  G  E  G  A  T  D  S  R  A  H  G  A  G ggtggcggtccgggtcgtgctggttgctgtctgggtaaagctgtgcgcggcgcgaaaggt

G  G  G  P  G  R  A  G  C  C  L  G  K  A  V  R  G  A  K  G
```

-continued

```
catcaccatccgcaccgccggcagcaggtgcaggtgcagctggcggtgcggaagccgat
 H  H  H  P  H  P  P  A  A  G  A  G  A  A  G  G  A  E  A  D ctgaaagccctgacccatagtgtcctgaaaaaactgaaagaacgtcagctggagctgctg
 L  K  A  L  T  H  S  V  L  K  K  L  K  E  R  Q  L  E  L  L ctgcaagcagtagaatcccgtggcggtacccgtacggcttgtctgctgctgccgggtcgt
 L  Q  A  V  E  S  R  G  G  T  R  T  A  C  L  L  L  P  G  R ctggattgccgtctgggtccgggtgcaccggctggtgcgcagccggcacaaccgccgagc
 L  D  C  R  L  G  P  G  A  P  A  G  A  Q  P  A  Q  P  P  S tcttacagcctgccgctgctgctgtgtaaagtgtttcgttggccggacctgcgccacagt
 S  Y  S  L  P  L  L  L  C  K  V  F  R  W  P  D  L  R  H  S tccgaagttaaacgcctgtgctgttgcgagagctatggcaaaattaacccggaactggtt
 S  E  V  K  R  L  C  C  C  E  S  Y  G  K  I  N  P  E  L  V tgttgcaatccgcaccatctgtctcgtctgtgtgaactggagagcccgccgccgccgtat
 C  C  N  P  H  H  L  S  R  L  C  E  L  E  S  P  P  P  P  Y tctcgttacccgatggatttcctgaaaccgactgcagattgcccggacgcagtcccgtca
 S  R  Y  P  M  D  F  L  K  P  T  A  D  C  P  D  A  V  P  S tcggctgagaccggcggcaccaactatctggcaccgggcggtctgagtgattcccagctg
 S  A  E  T  G  G  T  N  Y  L  A  P  G  G  L  S  D  S  Q  L ctgctggaaccgggcgaccgttcacattggtgtgtggttgcctattgggaagagaaaacg
 L  L  E  P  G  D  R  S  H  W  C  V  V  A  Y  W  E  E  K  T cgtgtcggtcgcctgtactgcgtacaggaaccgtcgctggatatctttatgacctgccg
 R  V  G  R  L  Y  C  V  Q  E  P  S  L  D  I  F  Y  D  L  P cagggcaatggtttctgtctgggccaactgaactcagataataaatcgcagctggtgcaa
 Q  G  N  G  F  C  L  G  Q  L  N  S  D  N  K  S  Q  L  V  Q aaagttcgctcaaaaattggctgcggtatccagctgacccgtgaagttgacggtgtctgg
 K  V  R  S  K  I  G  C  G  I  Q  L  T  R  E  V  D  G  V  W gtatataaccgcagctcttacccgattttttatcaaaagtgccaccctggataatccggac
 V  Y  N  R  S  S  Y  P  I  F  I  K  S  A  T  L  D  N  P  D tcccgtacgctgctggtccacaaagtatttccgggcttctcaatcaaagcgttcgattac
 S  R  T  L  L  V  H  K  V  F  P  G  F  S  I  K  A  F  D  Y gagaaagcctactcgctgcagcgcccgaacgaccatgaattcatgcagcaaccgtggacg
 E  K  A  Y  S  L  Q  R  P  N  D  H  E  F  M  Q  Q  P  W  T ggttttactgtgcagatctctttcgttaaaggctggggtcaatgctacacccgtcagttt
 G  F  T  V  Q  I  S  F  V  K  G  W  G  Q  C  Y  T  R  Q  F atctcgtcctgtccgtgctggctggaagtgattttcaatagccgcaagggcgagctcaat
 I  S  S  C  P  C  W  L  E  V  I  F  N  S  R  K  G  E  L  N tcgaagcttgaaggtaagcctatccctaaccctctcctcggtctcgattctacgcgtacc
 S  K  L  E  G  K  P  I  P  N  P  L  L  G  L  D  S  T  R  T Ggtcatcatcaccatcaccattgagtttgatccggctgctaacaaagcccgaaagga (SEQ ID NO:
  9)

G  H  H  H  H  H  H  - (SEQ ID NO: 10)
```

A comparison of the protein sequence of Tat-Smad7-v5 and Smad7 is provided below. The first amino acid of Smad7 in Tat-Smad7 is not M (unlike Smad7), because Tat-Smad7 is designed to be in-frame with Tat and/or GST to form a GST fusion protein. Tat-Smad7 is then cleaved from the GST fusion protein after purification. Upper case nucleotides identify the V5 tag. Underlined italics indicate amino acids from the optional pET101-Topo backbone vector.

Below a Tat-Smad7-v5 and Smad7 comparison is presented:

```
Tat-Smad7-V5    1 gsgrkkrrqrrrgfrtkrsalvrrlwrsrap
                  ggedeeegagggggggelr human Smad7     1 ------------mfrtkrsalvrrlwrsrap
                  ggedeeegagggggggelr Tat-Smad7-V5   51 gegatdsrahgagggpgragcclgkavrga
                  kghhhphppaagagaagga human Smad7    39 gegatdsrahgagggpgragcclgkavrga
                  kghhhphppaagagaagga Tat-Smad7-V5  101 eadlkalthsvlkklkerqlelllqavesrg
                  gtrtaclllpgrldcrlgp human Smad7    89 eadlkalthsvlkklkerqlelllqavesrg
                  gtrtaclllpgrldcrlgp Tat-Smad7-V5  151 gapagaqpaqppssyslplllckvfrwpdlr
                  hssevkrlcccesygkinp human Smad7   139 gapagaqpaqppssyslplllckvfrwpdlr
                  hssevkrlcccesygkinp Tat-Smad7-V5  201 elvccnphhlsrlcelesppppysrypmdfl
                  kptadcpdavpssaetggt human Smad7   189 elvccnphhlsrlcelesppppysrypmdfl
                  kptadcpdavpssaetggt Tat-Smad7-V5  251 nylapgglsdsqlllepgdrshwcvvaywee
                  ktrvgrlycvqepsldify human Smad7   239 nylapgglsdsqlllepgdrshwcvvaywee
                  ktrvgrlycvqepsldify Tat-Smad7-V5  301 dlpqgngfclgqlnsdnksqlvqkvrskigc
                  giqltrevdgvwvynrssy human Smad7   289 dlpqgngfclgqlnsdnksqlvqkvrskigc
                  giqltrevdgvwvynrssy Tat-Smad7-V5  351 pifiksatldnpdsrtllvhkvfpgfsikaf
                  dyekayslqrpndhefmqq human Smad7   339 pifiksatldnpdsrtllvhkvfpgfsikaf
                  dyekayslqrpndhefmqq Tat-Smad7-V5  401 pwtgftvqisfvkgwgqcytrqfisscpcwl
                  evifnsrkgelnskleGKP human Smad7   389 pwtgftvqisfvkgwgqcytrqfisscpcwl
                  evifnsr------------

Tat-Smad7-V5  451 IPNPLLGLDST (SEQ ID NO: 11)

human Smad7   427 ----------- (SEQ ID NO: 12)
```

Example 5

Additional Assays for PTD-Smad7 Protein Activity

Immunofluorescence (IF), Immunohistochemistry (IHC), and TUNEL Assay for Apoptosis.

IF and IHC were performed as previously described (Han, G., Li, F., Ten Dijke, P. & Wang, X. J. Temporal smad7 transgene induction in mouse epidermis accelerates skin wound healing. *Am J Pathol* 179, 1768-1779 (2011)). Primary antibodies used were guinea pig antibody to K14 (1:400, Fitzgerald, 20R-CP200), rat antibody to CD4 (1:20, BD Bioscience, 550278), Ly-6G (1:20, BD Bioscience, 550291), BM8 (antibody to F4/80, 1:20, Invitrogen, MF48000), FITC-labeled antibody to BrdU (BD Bioscience, 347583), rat antibody to CD45 (1:50, BD Bioscience, 550539) for mouse samples, mouse antibody to CD45 (1:50, Abcam, Ab781) for human samples, chicken antibody to TGF-β1 (1:50, R&D, AF-101-NA), rabbit antibody to CtBP1 (1:100, Millipore, 07-306), rabbit antibody to NF-κB p50 (1:200, Santa Cruz Biotechnology, SC-7178), rabbit antibody to PCNA (1:200, Santa Cruz Biotechnology, SC-7907), rabbit antibody to pSmad2 (1:100, Cell Signaling Technology, 3101), and mouse antibody to V5 (1:500, Invitrogen, 460705). For IF, secondary antibodies to different species IgG were Alexa Fluor® 594 (red) or 488 (green) conjugated (1:200 for all, Invitrogen). For IHC, secondary biotinylated antibodies to different species IgG (1:300, Vector Labs) were used and were developed using Vectastain ABC kit (Vector Labs). A Terminal deoxynucleotidyl transferase uridine nick end-labeling (TUNEL, G3250) kit (Promega) was used on formalin fixed tissue sections to detect apoptotic cells. BrdU labeling was performed in vivo by i.p. injection of 0.125 mg $g^{-1}$ BrdU 1 hour prior to euthanization. PCNA or BrdU were quantified as cells $mm^{-1}$ epithelial length including all epithelial cells, TUNEL or CD45-positive cells as cells $mm^{-1}$ epithelial length including all epithelial layers and stroma above the muscle layer, nuclear pSmad2 or NF-κB p50 positive cells as the number of positive cells/existing total remaining epithelial cells (i.e., excluding sloughed epithelial cells induced by irradiation). Consecutive fields of slides were used to count BrdU-labeled cells using MetaMorph software.

Cell Culture.

Smad7 transgenic and wild-type primary keratinocytes were prepared from neonatal mouse skin as previously described (Han, G., Li, F., Ten Dijke, P. & Wang, X. J. Temporal smad7 transgene induction in mouse epidermis accelerates skin wound healing. *Am J Pathol* 179, 1768-1779 (2011)), and cultured in PCT medium (CELLnTEC). Spontaneously immortalized normal oral keratinocytes (NOK-SI) derived from gingival tissues of healthy volunteers were cultured and maintained in defined keratinocyte medium (Castilho, R. M., et al. Rac1 is required for epithelial stem cell function during dermal and oral mucosal wound healing but not for tissue homeostasis in mice. *PLoS one* 5, e10503 (2010)). Oral cancer cells Cal27 (ATCC) and MSK921 were cultured (D. Raben's lab, fingerprinted by University of Colorado Cancer Center Tissue Culture Core) in Dulbecco Modified Eagle Medium supplemented with 10% fetal bovine serum (GIBCO®; Invitrogen). To assess the effect of Tat-Smad7 in irradiated cells, the above human cell lines were cultured in chamber slides (BD Bioscience, 354108), irradiated with 3 Gy, and Tat-Smad7 (1 μg $mL^{-1}$) was added to the culture medium immediately after irradiation. Cells were fixed in 100% cold methanol 4 hours after Tat-Smad7 treatment for immunostaining of pSmad2, NF-κB p50 and V5.

Transfection with siRNA. When cultured keratinocytes reached 70% confluency, 100 nM of target siRNA or scrambled siRNA (Dharmacon) was transfected using LIPOFECTAMINE® 2000 (Invitrogen). Cells were harvested 48-72 hours after transfection and subjected to western analyses to determine knockdown efficiency. For migration assays, siRNA was transfected when cells were plated. Target siRNAs included in this study are: mouse siRac1-1 (Invitrogen, MSS237708) and siRac1-2 (IDT, MMC.R-

NAI.N009007.12.3); human siSmad2 (Dharmacon, L-003561-00-0005), siSmad3 (Invitrogen, HSS106252), and siSmad4 (Invitrogen, HSS118066); human siCtBP1-1 and siCtBP1-2; human siSmad7-1 and siSmad7-2; human TGF-β1 (Dharmacon, J-012562-08-0005); mouse siSmad7.

In Vitro Keratinocyte Proliferation Assay.

In vitro keratinocyte proliferation was determined by BrdU incorporation in wild-type and Smad7 transgenic keratinocytes. Cells at 70% confluency were transfected with Rac1 siRNAs, and changed to regular culture medium 24 hours later. An in situ cell proliferation kit (Roche Applied Science) was used to perform in vitro BrdU labeling and detection, and MetaMorph software was used to count BrdU-labeled cells.

In Vitro Cell Migration Assays.

When cells reached 100% confluency, the cells were treated with mitomycin C (Sigma) at 10 μg mL$^{-1}$ for 2 hours to inhibit cell proliferation and a scratch wound was introduced with a Fisherbrand pipet tip. Cell migration was photographed daily. Migration assays were performed when cells reached confluency after 24 to 36 hours of siRNA transfection, and Image-J software was used to document cell migration as the wound area occupied with migrating cells. For Tat-Smad7 treatment, cells were exposed to Tat-Smad7 protein at 1 μg mL$^{-1}$ or vehicle control (PBS) in medium after wound scratch, and medium was changed every other day with freshly added Tat-Smad7 until migrating cells fully covered the scratched wound.

Cell Survival Assay.

Cell survival assays were performed as previously described (Munshi, A., Hobbs, M. & Meyn, R. E. Clonogenic cell survival assay. *Methods in molecular medicine* 110, 21-28 (2005)), with slight modifications. Briefly, cells were plated in 12-well plates at 500 cells well$^{-1}$ for non-irradiated wells, and increased up to 1,500 cells well$^{-1}$ along with increased radiation doses. Cells were irradiated 24 hours after they were plated. Tat-Smad7 was added at 1 μg mL$^{-1}$ or the same volume of PBS used to dissolve Tat-Smad7 (control) to culture medium of irradiated and non-irradiated cells. The medium was changed every other day with freshly added Tat-Smad7 or PBS for 10 to 14 days. Colonies were fixed in methanol, stained in 0.5% crystal violet solution (containing 25% methanol), counted and the average from 4 wells in each experiment was calculated. Two to three separate experiments were performed for each cell line. The relative surviving fraction was calculated as previously described, i.e., the absolute surviving fraction (colony numbers/total plated cells) under each radiation dose divided by the absolute surviving fraction of non-irradiated cells.

Western Analysis.

Protein extraction and western analyses were performed as previously described (Li, A. G., Lu, S. L., Zhang, M. X., Deng, C. & Wang, X. J. Smad3 knockout mice exhibit a resistance to skin chemical carcinogenesis. *Cancer Res* 64, 7836-7845 (2004)). The antibodies used in this study included rabbit antibody to Smad7 (1:500), rabbit antibodies to Smad2 (1:300, Zymed, 51-1300) and Smad4 (1:300, Epitomics, 1676-1), rabbit antibody to Smad3 (1:300, Cell Signaling Technology, 9513), mouse antibody to Rac1 (1:500, BD Biosciences, 610651), rabbit antibody to CtBP1 (1:500, Millipore, 07-306), mouse antibody to tubulin (1:3000, Sigma, T5168), mouse antibody to GAPDH (1:5000, Abcam, Ab8245) and goat antibody to actin (1:1000, Santa Cruz Biotechnology, SC1616). Gray-scale images were obtained using the ODYSSEY® v.1.2 software (LI-COR Biosciences).

Rac1 Activation Assay.

Active GTP-bound Rac1 was examined using a BIO-CHEM™ Kit for Rac1 activation (Cytoskeleton Inc, BK035). Wild-type and Smad7 transgenic keratinocytes were cultured in 15 cm diameter tissue culture plates and prepared protein lysates using the provided lysis buffer. To assay Rac1 activity, 1 mg of cell lysate was used. To examine total Rac1 and Smad7 proteins, 50 mg of lysate was used. To measure GTP-bound Rac1 in mouse tongues, half of the tongue was ground to a powder in liquid nitrogen and lysed with lysis buffer to extract protein, GTP-bound Rac1 was assayed in 2 mg of protein lysate per sample and 50 mg of protein lysate was loaded for total Rac1 protein western blot.

ChIP Assays.

ChIP assays were performed using the ChIP-IT express kit (Active Motive, 53009) as previously described (Hoot, K. E., et al. HGF upregulation contributes to angiogenesis in mice with keratinocyte-specific Smad2 deletion. *J Clin Invest* 120, 3606-3616 (2010); Hoot, K. E., et al. Keratinocyte-specific Smad2 ablation results in increased epithelial-mesenchymal transition during skin cancer formation and progression. Owens, et al., *J. Clin. Invest* 118, 2722-2732 (2008). Smad4-dependent desmoglein-4 expression contributes to hair follicle integrity. Owens, et al., *Dev. Biol.* 322:156-166 (2008). DNA-protein complex was isolated from primary mouse keratinocytes. For ChIP, 6.3 mg sheared chromatin was incubated with protein-G magnetic beads and 2 mg each of rabbit antibodies to Smad2 (Cell Signaling Technology, 3122), Smad3 (Cell Signaling Technology, 9523), Smad4 (Cell Signaling Technology, 9515), Smad7 antibody (Santa Cruz Biotechnology, SC-11392), CtBP1 (Millipore) or a negative control rabbit IgG (Santa Cruz Biotechnology, SC-2027). Eluted DNA from the protein-DNA complex was used for PCR analyses, and CtBP1 binding to the Rac1 promoter was compared in wild-type and Smad7 transgenic keratinocytes by ChIP band intensities on gel images or by quantitative PCR using Power SYBR Green Master Mix (Applied Biosystems). Primers used to amplify the Rac1 SBE-1.5 Kb promoter regions:

```
                                       (SEQ ID NO: 13)
   5'-TGGAATTCCTGGTCTGGTTT-3' (sense)

(SEQ ID NO: 14)
   5'-GCCAAGCTGCTCTTCCAGTA-3' (antisense)

(SEQ ID NO: 15)
   5'-TCTCAGGGGGCCAAAGGTGTT-3' (sense)

(SEQ ID NO: 16)
   5'-TCCCAGCACCTGAATCACATGG-3' (antisense)
```

Rac1 Promoter Luciferase Reporter Construct, Site-Directed Mutagenesis and Luciferase Assay.

The 883 bp fragment of −1671 bp to −789 bp of the Rac1 promoter, encompassing the SBE-1.5 Kb site, was amplified from wild-type mouse DNA using 5' XhoI and 3' HindIII tagged primers, and this Rac1 promoter fragment was cloned into pGL4.26 vector (Promega) to make the Rac1 promoter-pGL4.26 luciferase reporter (Rac1-Luc) construct. For site-directed mutagenesis, the SBE sequence 5'-TGTCTGTGCT-3' (SEQ ID NO: 17) was mutated to 5'-TGATAGAGCT-3' (SEQ ID NO: 18). Rac1-Luc and pGL4.74 (1:20) were co-transfected with Smad7 siRNA, CtBP1 siRNA or scrambled siRNA using Lipofectamine 2000 (Invitrogen) to primary mouse keratinocytes, or primary mouse keratinocytes with Tat-Smad7 treatment (1 μg mL$^{-1}$). Cell lysates were collected and luciferase assays were performed 48 hours after transfection or Tat-Smad7 treatment, using the DUAL-LU-CIFERASE® Reporter Assay kit (Promega) following manufacturer's instructions. Rac1-luciferase activity was measured with the Glomax machine (Promega) and expressed by the ratio of firefly activity to Renilla activity. Primers used for amplification of Rac1 promoter sequence were:

```
                                       (SEQ ID NO: 19)
5'-ATCCTCGAG-TATCCTCCAGGTCTGGG-3'

(SEQ ID NO: 20)
5'-GCCAAGCTT-AGCGTCCAGCGTTAACCTG-3'
```

Statistical Analysis.

Statistical differences in molecular analyses and oral mucositis ulcer size were analyzed using the Student's t-test and all data was presented by mean±s.d. except ulcer size, which was presented by mean±s.e.m. Oral mucositis incidences were analyzed by Fisher's exact test.

Example 6

Codon Optimization for Smad7 Protein Production in *E. coli* or Yeast

Although many mammalian proteins can be produced in bacteria without nucleotide sequence modification, the analysis indicated that the Smad7 nucleotide sequence would need to be modified to allow protein expression in bacteria.

Analysis of Smad7 cDNA mammalian codon use revealed nine arginine amino acids coded for by the following nucleotides: 7-9, 43-45, 169-171, 403-405, 490-492, 526-528, 526-528, 823-825, 1057-1059 are a rare codon (AGG, codon utilization 1.7%). Since these codons are rare codons in bacteria, it is expected that they could halt or reduce protein translation and/or production in bacteria. The amino acids coded for by rare arginine codons are indicated by bold capitals below in the illustrated human Smad7 protein, including arginines at positions 3, 15, 57, 135, 164, 169, 176, 275, and 353. Additionally, the following arginine codons also have low frequency usages. CGA (3.5% codon utilization): nucleotides 16-18, 136-138, 199-201, 598-600, which code for arginine at positions 6, 46, 67, 200; CGG (5.4% codon utilization): nucleotides 31-33, 112-114, 316-318, 772-774, 940-942, 973-975, 1135-1137, 1276-1278, which code for arginine at positions 11, 38, 106, 258, 314, 325, 379, 426; AGA (2.8% codon utilization): nucleotides 637-639, 814-816, which code for arginine at positions 213, 272. These arginine residues are highlighted in bold upper case R below and they are changed to CGC in at least one of the codon-optimized nucleic acid sequences (20.6% codon utilization):

```
                                       (SEQ ID NO: 12)
  1 mfRtkRsalv RrlwRsrapg gedeeegagg ggggelRge
    gatdsRahga 51 ggggpgRagc clgkavrgak ghhhphppaa gagaaggaea
    dlkalthsvl 101 kklkeRqlel llqavesrgg trtaclllpg rldcRlgpga
    pagaqpaqpp 151 ssyslplllc kvfRwpdlRh ssevkRlccc esygkinpel
    vccnphhlsR 201 lcelespppp ysRypmdflk ptadcpdavp ssaetggtny
    lapgglsdsq 251 lllepgdRsh wcvvayweek tRvgRlycvq epsldifydl
    pqgngfclgq
```

```
                                    -continued
301 lnsdnksqlv qkvRskigcg iqltRevdgv wvynrssypi
    fiksatldnp 351 dsRtllvhkv fpgfsikafd yekayslqRp ndhefmqqpw
    tgftvgisfv 401 kgwgqcytrq fisscpcwle vifnsR
```

Based on this analysis, it was decided to optimize the Smad7 nucleotide sequence to codons that were believed to allow increased Tat-Smad7 protein production in *E. coli* or yeast. Provided below is the optimized nucleic acid codon sequence made by Genscript. Briefly, the sequence has the following composition: nucleotides 1-6 include the restriction recognition site for BamHI; nucleotides 7-36 include the Tat sequence; nucleotides 37-1314 include codon-optimized human Smad7 cDNA; nucleotides 1342-1383 include the V5 epitope; nucleotides 1384-1386 are the stop codon; and nucleotides 1387-1392 including the restriction recognition site for SalI. In this sequence, ATG is removed to be used with GST. The entire designed sequence was converted to *E. coli* codons based on "Codon-Usage Database." The initial optimized Smad7 sequence (SEQ ID NO: 23) is shown below:

```
                                       (SEQ ID NO: 23)
  1 ggatccggcc gtaaaaaacg ccgtcaacgc cgccgtggtt
    tccgtacgaa acgctcggcc 61 ctggtccgtc gcctgtggcg ctcccgtgct ccgggtggtg
    aagatgaaga agaaggtgct 121 ggcggcggtg gcggtggcgg tgaactgcgt ggcgagggtg
    caaccgatag tcgtgcacac 181 ggtgcaggcg gtgccggtcc gggtcgtgct ggttgctgtc
    tgggtaaagc tgtgcgcggc 241 gcgaaaggtc atcaccatcc gcacccgccg gcagcaggtg
    caggtgcagc tggcggtgcg 301 gaagccgatc tgaaagccct gacccatagt gtcctgaaaa
    aactgaaaga acgtcagctg 361 gagctgctgc tgcaagcagt agaatcccgt ggcggtaccc
    gtacggcttg tctgctgctg 421 ccgggtcgtc tggattgccg tctgggtccg ggtgcaccgg
    ctggtgcgca gccggcacaa 481 ccgccgagct cttacagcct gccgctgctg ctgtgtaaag
    tgtttcgttg gccggacctg 541 cgccacagtt ccgaagttaa acgcctgtgc tgttgcgaga
    gctatggcaa aattaacccg 601 gaactggttt gttgcaatcc gcaccatctg tctcgtctgt
    gtgaactgga gagcccgccg 661 ccgccgtatt ctcgttaccc gatggatttc ctgaaaccga
    ctgcagattg cccggacgca 721 gtcccgtcat cggctgagac cggcggcacc aactatctgg
    caccgggcgg tctgagtgat 781 tcccagctgc tgctggaacc gggcgaccgt tcacattggt
    gtgtggttgc ctattgggaa 841 gagaaaacgc gtgtcggtcg cctgtactgc gtacaggaac
    cgtcgctgga tatcttttat 901 gacctgccgc agggcaatgg tttctgtctg ggccaactga
    actcagataa taaatcgcag 961 ctggtgcaaa aagttcgctc aaaaattggc tgcggtatcc
    agctgacccg tgaagttgac
```

-continued

```
1021  ggtgtctggg tatataaccg cagctcttac ccgattttta
      tcaaaagtgc caccctggat 1081  aatccggact cccgtacgct gctggtccac aaagtatttc
      cgggcttctc aatcaaagcg 1141  ttcgattacg agaaagccta ctcgctgcag cgcccgaacg
      accatgaatt catgcagcaa 1201  ccgtggacgg gttttactgt gcagatctct ttcgttaaag
      gctggggtca atgctacacc 1261  cgtcagttta tctcgtcctg tccgtgctgg ctggaagtga
      ttttcaatag ccgcaagggc
```

-continued

```
1321  gagctcaatt cgaagcttga aggtaagcct atccctaacc
      ctctcctcgg tctcgattct 1381  acgtgagtcg ac
```

A nucleotide sequence comparison between Tat-Smad7-V5 (SEQ ID NO: 23) and human Smad7 (SEQ ID NO: 22) cDNA is provided below. Human Smad7 and codon-optimized Tat-Smad7-V5 share 68% codon homology. Human Smad7 and codon-optimized Tat-Smad7 share 71% codon homology. Human Smad7 and codon-optimized Smad7 share 73% codon homology.

```
Alignment: Global DNA alignment against reference molecule
Parameters: Scoring matrix: Linear (Mismatch 2, OpenGap 4, ExtGap 1)
   Reference molecule: human Smad7 mRNA, Region 1-1281
   Number of sequences to align: 2
   Settings: Similarity significance value cutoff: >=90%
Summary of Percent Matches:
   Reference: human Smad7 mRNA 1-1281 (1281 bps) —
   Sequence 2: Tat-Smad7-V5 1-1392 (1392 bps) 68% human Smad7     1  --atg---------------------------ttcaggaccaaacgatctgcg
Tat-Smad7-V5    1  ggatccggccgtaaaaaacgccgtcaacgccgccgtggtttccgtacgaaacgctcggcc human Smad7    25  ctcgtccggcgtctctggaggagccgtgcgccggcggcgaggacgaggaggagggcgca
Tat-Smad7-V5   61  ctggtccgtcgcctgtggcgctcccgtgctccgggtggtgaagatgaagaagaaggtgct human Smad7    85  ggggagtggaggaggaggcgagctgcgggagaagggcgacggacagccgagcgcat
Tat-Smad7-V5  121  ggcggcggtggcggtggcggtgaactgcgtggcgagggtgcaaccgatagtcgtgcacac human Smad7   145  ggggccggtggcggcggccggggcagggctggatgctgcctgggcaaggcggtgcgaggt
Tat-Smad7-V5  181  ggtgcaggcggtggcggtccgggtcgtgctggttgctgtctgggtaaagctgtgcgcggc human Smad7   205  gccaaaggtcaccaccatcccccaccgccagccgcgggcgccggcgcggccggggcgcc
Tat-Smad7-V5  241  gcgaaaggtcatcaccatccgcaccgccggcagcaggtgcaggtgcagctggcggtgcg human Smad7   265  gaggcggatctgaaggcgctcacgcactcggtgctcaagaaactgaaggagcggcagctg
Tat-Smad7-V5  301  gaagccgatctgaaagccctgacccatagtgtcctgaaaaaactgaaagaacgtcagctg human Smad7   325  gagctgctgctccaggccgtggagtccgcggcgggacgcgcaccgcgtgcctcctgctg
Tat-Smad7-V5  361  gagctgctgctgcaagcagtagaatcccgtggcggtaccgtaccggcttgtctgctgctg human Smad7   385  cccggccgcctggactgcaggctgggccgggggcgccgcggcgcgcagcctgcgcag
Tat-Smad7-V5  421  ccgggtcgtctggattgccgtctgggtccgggtgcaccggctggtgcgcagccggcacaa human Smad7   445  ccgccctcgtcctactcgctcccctcctgctgtgcaaagtgttcaggtggcggatctc
Tat-Smad7-V5  481  ccgccgagctcttacagcctgccgctgctgctgtgtaaagtgtttcgttggccggacctg human Smad7   505  aggcattcctcggaagtcaagaggctgtgttgctgtgaatcttacgggaagatcaaccgc
Tat-Smad7-V5  541  cgccacagttccgaagttaaacgcctgtgctgttgcgagagctatggcaaaattaaccgg human Smad7   565  gagctggtgtgctgcaacccccatcaccttagccgactctgcgaactagagtctccccgc
Tat-Smad7-V5  601  gaactggtttgttgcaatccgcaccatctgtctcgtctgtgtgaactggagagccgccg human Smad7   625  cctcctactccagataccgatggattttctcaaaccaactgcagactgtccagatgct
Tat-Smad7-V5  661  ccgccgtattctcgttaccgatggatttcctgaaaccgactgcagattgccggacgca human Smad7   685  gtgccttcctccgctgaaacaggggaacgaattatctggccctgggggctttcagat
Tat-Smad7-V5  721  gtcccgtcatcggctgagaccggcggcaccaactatctgcaccggcggtctgagtgat human Smad7   745  tcccaacttcttctggagcctggggatcggtcacactggtgcgtggtggcatactgggag
Tat-Smad7-V5  781  tcccagctgctgctggaaccgggcgaccgttcacattggtgtgtggttgcctattgggaa human Smad7   805  gagaagacgagagtggggaggctctactgtgtccaggagccctctctggatatcttctat
Tat-Smad7-V5  841  gagaaacgcgtgtcggtcgcctgtactgcgtacaggaaccgtcgctggatatcttttat human Smad7   865  gatctacctcagggggaatggctttgcctcggacagctcaattcggacaacaagagtcag
Tat-Smad7-V5  901  gacctgccgcaggggcaatggtttctgtctgggccaactgaactcagataatagatcgcag human Smad7   925  ctggtgcagaaggtgcggagcaaaatcggctgcggcatccagctgacgcgggaggtggat
Tat-Smad7-V5  961  ctggtgcaaaaagttcgctcaaaaaattggctgcggtatccagctgaccgtgaagttgac
```

```
human Smad7      985  ggtgtgtgggtgtacaaccgcagcagttaccccatcttcatcaagtccgccacactggac
Tat-Smad7-V5    1021  ggtgtctgggtatataaccgcagctcttacccgattttatcaaaagtgccacctggat human Smad7     1045  aaccggactccaggacgctgttggtacacaaggtgttccccggtttctccatcaagget
Tat-Smad7-V5    1081  aatccggactcccgtacgctgctggtccacaaagtatttccgggcttctcaatcaaagcg human Smad7     1105  ttcgactacgagaaggcgtacagcctgcagcggcccaatgaccacgagtttatgcagcag
Tat-Smad7-V5    1141  ttcgattacgagaaagcctactcgctgcagcgcccgaacgaccatgaattcatgcagcaa human Smad7     1165  ccgtggacgggctttaccgtgcagatcagctttgtgaagggctggggtcagtgctacacc
Tat-Smad7-V5    1201  ccgtggacgggttttactgtgcagatctctttcgttaaaggctggggtcaatgctacacc human Smad7     1225  cgccagttcatcagcagctgccgtgctggctagaggtcatcttcaacagccggtag---
Tat-Smad7-V5    1261  cgtcagtttatctcgtcctgtccgtgctggctggaagtgattttcaatagccgcaagggc human Smad7     1282  ------------------------------------------------------------
Tat-Smad7-V5    1321  gagctcaattcgaagcttgaaggtaagcctatccctaaccctctcctcggtctcgattct human Smad7     1282  ------------
Tat-Smad7-V5    1381  acgtgagtcgac
```

In this optimization, Met216, which may form an alternative open reading frame, was not altered as it was desired to preserve the amino acid sequence of Smad7, if possible. In future codon optimizations, Met216 will be mutated to Leu216 to improve protein production without impacting function in vitro and in vivo.

Example 7

Production of Truncated Smad7 Proteins

Figure 15:
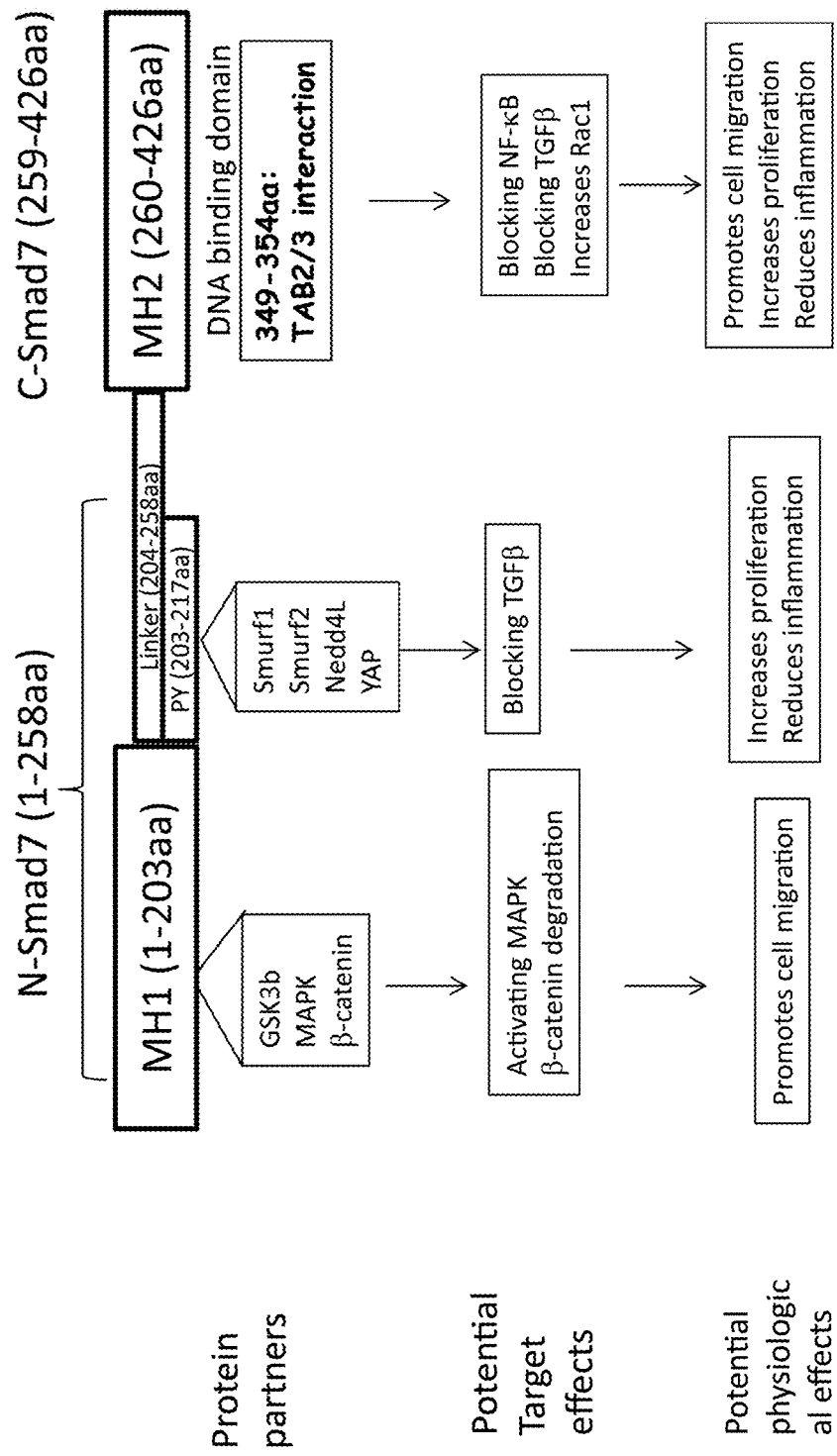
FIG. 15 shows an illustrative schematic of Smad 7 domains associated with protein partners, potential target effects, and potential physiological effects.

It is believed that Smad7 has several activities in vivo including, but not limited to, one or more of enhancing cell proliferation, enhancing cell migration, reducing DNA damage, reducing cell apoptosis, and decreasing inflammation. Smad7's effects on these processes are due to one or more of blocking TGF-3 signaling, blocking NF-κB signaling, blocking CtBP1 activity, and/or increasing Rac1 expression and/or activity. It is believed that a smaller functional domain of Ptd-Smad7 may be sufficient to deliver a therapeutic effect (see, e.g., FIG. 15). In addition, the resulting shorter protein sequence is expected to enhance protein production. Additionally, it is believed that different truncated Tat-Smad7 proteins that contain partial Smad7 sequences may be useful for different treatments.

For example, it is believed that the C-terminal MH2 domain of Smad7 (about half length of Smad7 protein, e.g., 208-426aa) may primarily mediate the anti-inflammatory effect of Smad7 (Hong et al., Nat Immunology, 8, 504-513, 2007). Smad7 peptides having this anti-inflammatory function may be sufficient and optionally an improvement for treating chronic inflammation associated conditions, such as but not limited to, oral mucositis, stomatitis and psoriasis, among others.

The N-terminal MH1 domain plus the linker region of Smad7 (about half of the protein, e.g., 2-208aa) is known to activate MAPK and binds to Smurf, a ubiquitin E3 ligase to degrade TGF-β receptor (Aragon, et al., Structure 20:1726-1736 (2012)). It is believed that it may primarily mediate cell migration and/or blocking TGF-β-induced growth arrest and/or fibrotic response. Smad7 peptides having this cell migration and proliferation function may be sufficient, and optionally an improvement, for enhancing healing that is not associated with excessive inflammation. Types of wounds that might benefit from this form of treatment include, but are not limited to, surgical wounds, fibrotic scarring, and diabetes wounds, defective healing and/or scarring among others.

Truncated Smad7 N-terminal and C-terminal PTD-fusion proteins were designed. One example of a Tat-Smad7-C-terminal codon-optimized nucleotide and protein sequence is provided below. In the nucleic acid sequence, nucleotides 1-6 include the restriction recognition site for BamHI; nucleotides 7-36 include the Tat PTD sequence; nucleotides 37-810 include codon-optimized for the C terminal amino acids 258 to 426 of human Smad7; nucleotides 568-609 include the V5 epitope sequence; nucleotides 610-612 include the stop sequence; and nucleotides 613-618 include the restriction recognition site for SalI:

```
ggatccggccgtaaaaaacgccgtcaacgccgccgttcacattggtgtgtggttgcctat
G  S  G  R  K  K  R  R  Q  R  R  R  S  H  W  C  V  V  A  Y tgggaagagaaaacgcgtgtcggtcgcctgtactgcgtacaggaaccgtcgctggatatc
W  E  E  K  T  R  V  G  R  L  Y  C  V  Q  E  P  S  L  D  I ttttatgacctgccgcagggcaatggtttctgtctgggccaactgaactcagataataaa
F  Y  D  L  P  Q  G  N  G  F  C  L  G  Q  L  N  S  D  N  K tcgcagctggtgcaaaaagttcgctcaaaaattggctgcggtatccagctgacccgtgaa
S  Q  L  V  Q  K  V  R  S  K  I  G  C  G  I  Q  L  T  R  E
```

```
                                                    -continued
gttgacggtgtctgggtatataaccgcagctcttacccgattttttatcaaaagtgccacc
 V  D  G  V  W  V  Y  N  R  S  S  Y  P  I  F  I  K  S  A  T ctggataatccggactcccgtacgctgctggtccacaaagtatttccgggcttctcaatc
 L  D  N  P  D  S  R  T  L  L  V  H  K  V  F  P  G  F  S  I aaagcgttcgattacgagaaagcctactcgctgcagcgcccgaacgaccatgaattcatg
 K  A  F  D  Y  E  K  A  Y  S  L  Q  R  P  N  D  H  E  F  M cagcaaccgtggacgggttttactgtgcagatctctttcgttaaaggctggggtcaatgc
 Q  Q  P  W  T  G  F  T  V  Q  I  S  F  V  K  G  W  G  Q  C tacacccgtcagtttatctcgtcctgtccgtgctggctggaagtgattttcaatagccgc
 Y  T  R  Q  F  I  S  S  C  P  C  W  L  E  V  I  F  N  S  R aagggcgagctcaattcgaagcttgaaggtaagcctatccctaaccctctcctcggtctc
 K  G  E  L  N  S  K  L  E  G  K  P  I  P  N  P  L  L  G  L gattctacgtgagtcgac (SEQ ID NO: 24)
 D  S  T- (SEQ ID NO: 25)
```

In the nucleic acid sequence, nucleotides 1-6 include the restriction recognition site for BamHI; nucleotides 7-36 include the Tat PTD sequence; nucleotides 37-810 include codon-optimized for the N terminal amino acids 1-258 of human Smad7; nucleotides 811-852 include the V5 epitope sequence (corresponding amino acid sequence in bold); nucleotides 853-855 include the stop sequence; and nucleotides 856-861 include the restriction recognition site for SalI. ATG is removed to allow for fusion with GST:

```
ggatccggccgtaaaaaacgccgtcaacgccgccgtggtttccgtacgaaacgctcggcc
 G  S  G  R  K  K  R  R  Q  R  R  R  G  F  R  T  K  R  S  A ctggtccgtcgcctgtggcgctcccgtgctccgggtggtgaagatgaagaagaaggtgct
 L  V  R  R  L  W  R  S  R  A  P  G  G  E  D  E  E  E  G  A ggcggcggtggcggtggcggtgaactgcgtggcgagggtgcaaccgatagtcgtgcacac
 G  G  G  G  G  G  E  L  R  G  E  G  A  T  D  S  R  A  H ggtgcaggcggtggcggtccgggtcgtgctggttgctgtctgggtaaagctgtgcgcggc
 G  A  G  G  G  G  P  G  R  A  G  C  C  L  G  K  A  V  R  G gcgaaaggtcatcaccatccgcacccgccggcagcaggtgcaggtgcagctggcggtgcg
 A  K  G  H  H  H  P  H  P  P  A  A  G  A  G  A  A  G  G  A gaagccgatctgaaagccctgacccatagtgtcctgaaaaaactgaaagaacgtcagctg
 E  A  D  L  K  A  L  T  H  S  V  L  K  K  L  K  E  R  Q  L gagctgctgctgcaagcagtagaatcccgtggcggtacccgtacggcttgtctgctgctg
 E  L  L  L  Q  A  V  E  S  R  G  G  T  R  T  A  C  L  L  L ccgggtcgtctggattgccgtctgggtccgggtgcaccggctggtgcgcagccggcacaa
 P  G  R  L  D  C  R  L  G  P  G  A  P  A  G  A  Q  P  A  Q ccgccgagctcttacagcctgccgctgctgctgtgtaaagtgtttcgttggccggacctg
 P  P  S  S  Y  S  L  P  L  L  L  C  K  V  F  R  W  P  D  L cgccacagttccgaagttaaacgcctgtgctgttgcgagagctatggcaaaattaacccg
 R  H  S  S  E  V  K  R  L  C  C  C  E  S  Y  G  K  I  N  P gaactggtttgttgcaatccgcaccatctgtctcgtctgtgtgaactggagagcccgccg
 E  L  V  C  C  N  P  H  H  L  S  R  L  C  E  L  E  S  P  P
```

-continued
ccgccgtatagccgttaccgctggatttcctgaaaccgactgcagattgcccggacgca

P P Y S R Y P M D F L K P T A D C P D A gtcccgtcatcggctgagaccggcggcaccaactatctggcacggggcggtctgagtgat

V P S S A E T G G T N Y L A P G G L S D tcccagctgctgctggaacgggcgaccgtggtaagcctatccctaaccctctcctcggt

S Q L L L E P G D R G K P I P N P L L G ctcgattctacgtgagtcgac (SEQ ID NO: 26)

L D S T -(SEQ ID NO: 27)

Example 8

Testing of Truncated Smad7 Proteins

Activity of truncated Smad7 proteins is tested using the in vitro and in vivo assays used to test full-length Smad7 described above, among other assays. Such assays include, but are not limited to, the ability to block phosphorylation of Smad2 and/or nuclear translocation of the NF-κB p50 subunit, increase cell proliferation, reduce apoptosis and/or radiation-induced DNA damage, reduce inflammation and/or angiogenesis, promote healing in oral mucositis, surgical wounds, diabetes wounds, and/or wounds associated with chronic inflammation in mice.

In a wound healing assay, 6-mm punch biopsies were performed in wild-type mice followed by daily topical application of C-terminal or N-terminal Tat-Smad7. By measuring gross wound closure, both truncated Smad7 proteins described above (e.g., Tat-Smad7 C-terminal and N-terminal protein) were found to have promoted wound healing similar to full length Tat-Smad7.

Example 9

Additional Codon Optimization for Smad7 Protein Production

Smad7 nucleic acid molecules are designed with additional nucleotide changes selected to increase protein production. For example, the utilization of codons encoding the amino acids Ser and His will be manipulated. In codon-optimized human Smad7 in examples above, the Ser codon (TCC or TCG) has an amino acid frequency of approximately 9% of codon utilization. It is believed that changing the codon of Ser to AGC will increase Smad7 protein production, at least partly because it can optionally increase codon usage to 15%. There are 33 Ser amino acids in Smad7 protein (nucleotides at positions 19-21, 46-48, 133-135, 292-294, 349-351, 451-453, 454-456, 460-462, 511-513, 514-516, 544-546, 595-597, 616-618, 634-636, 691-693, 694-696, 739-741, 745-747, 775-777, 847-849, 907-909, 919-921, 943-945, 1006-1008, 1009-1101, 1030-1032, 1054-1056, 1093-1095, 1126-1128, 1192-1194, 1237-1239, 1240-1242, 1273-1275; with a corresponding serine amino acid position of 7, 16, 45, 98, 117, 151, 152, 154, 171, 172, 182, 199, 206, 212, 231, 232, 247, 249, 259, 283, 303, 307, 315, 336, 337, 344, 352, 365, 376, 398, 413, 414, 425). Of these, 23 (nucleotides 19-21, 292-294, 349-351, 451-453, 454-456, 460-462, 511-513, 514-516, 544-546, 616-618, 634-636, 691-693, 694-696, 739-741, 745-747, 775-777, 847-849, 907-909, 919-921, 1009-1101, 1030-1032, 1054-1056, 1093-1095; corresponding serine amino acid position of 7, 98, 117, 151, 152, 154, 171, 172, 182, 206, 212, 231, 232, 247, 249, 259, 283, 303, 307, 337, 344, 352, 365) can be changed without introducing potential alternative open reading frames.

Similarly, in codon-optimized human Smad7 in the examples above, the His codon (CAC) has 9.6% of codon usage. It is believed that changing the His codon to CAT (optionally to 12.6% usage) will increase Smad7 protein production. There are 12 His (nucleotides 142-144, 214-216, 217-219, 220-222, 226-228, 289-291, 589-591, 778-780, 1072-1074, 1147-1149; corresponding to histidine amino acids at position 48, 72, 73, 74, 76, 97, 170, 196, 197, 260, 358, 383) in Smad7 protein. Of these, 4 (nucleotides 217-219, 220-222, 589-591, 778-780, histidine residues 73, 76, 197, 260) can be changed without introducing potential alternative open reading frames.

In addition, wild-type human Smad7 includes a Met amino acid as amino acid 216 (Met216). This may be perceived as an alternative open reading frame by bacterial machinery, for example, and decrease protein production. It is believed that changing Met216 to Leu216 (ATG to CTG), the amino acid that has the biochemical property the closest to Met and thus not expected to change 3D structure of the protein, will increase protein production.

The comparison between original codon-optimized Tat-Smad7-V5 and further changes is provided below. Top strand: Tat-Smad7-V5 (SEQ ID NO: 23); bottom strand:

---

```
Alignment: Local DNA homologies.
Parameters: Both strands. Method: FastScan-Max Score
   Mol 1 20120323113102B12-S54366-164160-1-PGEX-5.seq (1-1463) Mol 2 TatSmad7 Ser-His optim
   Number of sequences to align: 2
   Settings: Similarity significance value cutoff: >=60%
Homology Block: Percent Matches 94 Score 1227 Length 1392
   201203231131    30   ggatccggccgtaaaaaacgccgtcaacgccgccgtggtttccgtacgaaacgctcggcc
   TatSmad7 Ser     1   ..............................................................agc...

201203231131    90   ctggtccgtcgcctgtggcgctccgtgctccgggtggtgaagatgaagaagaaggtgct
   TatSmad7 Ser    61   ..........................ag..........................................
```

```
201203231131   150  ggcggcggtggcggtggcggtgaactgcgtggcgagggtgcaaccgatagtcgtgcacac
TatSmad7 Ser   121  .....................................................c........t 201203231131   210  ggtgcaggcggtggcggtccgggtcgtcctggttgctgtctgggtaaagctgtgcgcggc
TatSmad7 Ser   181  ............................................................

201203231131   270  gcgaaaggtcatcaccatccgcaccgccggcagcaggtgcaggtgcagctggcggtgcg
TatSmad7 Ser   241  ..............t........t....................................

201203231131   330  gaagccgatctgaaagccctgacccatagtgtcctgaaaaaactgaaagaacgtcagctg
TatSmad7 Ser   301  ...............................c............................

201203231131   390  gagctgctgctgcaagcagtagaatcccgtggcggtacccgtacggcttgtctgctgctg
TatSmad7 Ser   361  ................................ag..........................

201203231131   450  ccgggtcgtctggattgccgtctgggtccgggtgcaccggctggtgcgcagccggcacaa
TatSmad7 Ser   421  ............................................................

201203231131   510  ccgccgagctcttacagcctgccgctgctgctgtgtaaagtgtttcgttggccggacctg
TatSmad7 Ser   481  ........agc..................................................

201203231131   570  cgccacagttccgaagttaaacgcctgtgctgttgcgagagctatggcaaaattaacccg
TatSmad7 Ser   541  .....t..cag..................................................

201203231131   630  gaactggtttgttgcaatccgcaccatctgtctcgtctgtgtgaactggagagcccgccg
TatSmad7 Ser   601  ....................t......agc...............................

201203231131   690  ccgccgtattgtcgttacccgatggatttcctgaaaccgactgcagattgcccggacgca
TatSmad7 Ser   661  ..........agc........c.......................................

201203231131   750  gtcccgtcatcggctgagaccggcggcaccaactatctggcaccgggcggtctgagtgat
TatSmad7 Ser   721  ......agcagc..............................................c...

201203231131   810  tcccagctgctgctggaaccgggcgaccgttcacattggtgtgtggttgcctattgggaa
TatSmad7 Ser   781  ag.............................agc..........................

201203231131   870  gagaaaacgcgtgtcggtcgcctgtactgcgtacaggaaccgtcgctggatatctttttat
TatSmad7 Ser   841  ..................................agc.......................

201203231131   930  gacctgccgcagggcaatggtttctgtctgggccaactgaactcagataataaatcgcag
TatSmad7 Ser   901  ...............................agc.........agc...

201203231131   990  ctggtgcaaaaagttcgctcaaaaattggctgcggtatccagctgacccgtgaagttgac
TatSmad7 Ser   961  ............agc..............................................

201203231131  1050  ggtgtctgggtatataaccgcagctcttacccgattttatcaaaagtgccaccctggat
TatSmad7 Ser  1021  ............agc.....................c........................

201203231131  1110  aatccggactccgtacgctgctggtccacaaagtatttccgggcttctcaatcaaagcg
TatSmad7 Ser  1081  ........ag.........t..............agc........................

201203231131  1170  ttcgattacgagaaagcctactggctgcagcgcccgaacgaccatgaattcatgcagcaa
TatSmad7 Ser  1141  ...............agc...........................................

201203231131  1230  ccgtggacgggttttactgtgcagatctctttcgttaaaggctggggtcaatgctacacc
TatSmad7 Ser  1201  ...............agc...........................................

201203231131  1290  cgtcagtttatctgtcctgtccgtgctggctggaagtgattttcaatagccgcaagggc
TatSmad7 Ser  1261  ...........agcag............................................

201203231131  1350  gagctcaattcgaagcttgaaggtaagcctatccctaaccctctcctcggtctcgattct
TatSmad7 Ser  1321  ........agc.............................................agc 201203231131  1410  acgtgagtcgac
TatSmad7 Ser  1381  ............
``` after optimized Ser, His and M216L mutation (SEQ ID NO: 30).

Nucleic acid sequences and their corresponding amino acid sequences that would include all these changes are provided below. The amino acid sequence includes the V5 epitope indicated in bold, and the pET101-Topo backbone indicated by italics and underlining. The Tat-Smad7$^{M216L}$ fully-optimized full length nucleotide and protein sequence is shown below:

ggatccggccgtaaaaaacgccgtcaacgccgccgtggtttccgtacgaaacgcagcgcc
G  S  G  R  K  K  R  R  Q  R  R  R  G  F  R  T  K  R  S  A ctggtccgtcgcctgtggcgcagccgtgctccgggtggtgaagatgaagaagaaggtgct
L  V  R  R  L  W  R  S  R  A  P  G  G  E  D  E  E  E  G  A ggcggcggtggcggtggcggtgaactgcgtggcgagggtgcaaccgatagccgtgcacat
G  G  G  G  G  G  E  L  R  G  E  G  A  T  D  S  R  A  H ggtgcaggcggtggcggtccgggtcgtgctggttgctgtctgggtaaagctgtgcgcggc
G  A  G  G  G  G  P  G  R  A  G  C  C  L  G  K  A  V  R  G gcgaaaggtcatcatcatccgcatccgccggcagcaggtgcaggtgcagctggcggtgcg
A  K  G  H  H  H  P  H  P  P  A  A  G  A  G  A  A  G  G  A gaagccgatctgaaagccctgacccatagcgtcctgaaaaaactgaaagaacgtcagctg
E  A  D  L  K  A  L  T  H  S  V  L  K  K  L  K  E  R  Q  L gagctgctgctgcaagcagtagaaagccgtggcggtacccgtacggcttgtctgctgctg
E  L  L  L  Q  A  V  E  S  R  G  G  T  R  T  A  C  L  L  L ccgggtcgtctggattgccgtctgggtccgggtgcaccggctggtgcgcagccggcacaa
P  G  R  L  D  C  R  L  G  P  G  A  P  A  G  A  Q  P  A  Q ccgccgagcagctacagcctgccgctgctgctgtgtaaagtgtttcgttggccggacctg
P  P  S  S  Y  S  L  P  L  L  L  C  K  V  F  R  W  P  D  L cgccatagcagcgaagttaaacgcctgtgctgttgcgagagctatggcaaaattaacccg
R  H  S  S  E  V  K  R  L  C  C  C  E  S  Y  G  K  I  N  P gaactggtttgttgcaatccgcatcatctgagccgtctgtgtgaactggagagcccgccg
E  L  V  C  C  N  P  H  H  L  S  R  L  C  E  L  E  S  P  P ccgccgtatagccgttacccgctggatttcctgaaaccgactgcagattgcccggacgca
P  P  Y  S  R  Y  P  L  D  F  L  K  P  T  A  D  C  P  D  A gtcccgagcagcgctgagaccggcggcaccaactatctggcaccgggcggtctgagcgat
V  P  S  S  A  E  T  G  G  T  N  Y  L  A  P  G  G  L  S  D agccagctgctgctggaaccgggcgaccgtagccattggtgtgtggttgcctattgggaa
S  Q  L  L  L  E  P  G  D  R  S  H  W  C  V  V  A  Y  W  E gagaaaacgcgtgtcggtcgcctgtactgcgtacaggaaccgagcctggatatcttttat
E  K  T  R  V  G  R  L  Y  C  V  Q  E  P  S  L  D  I  F  Y gacctgccgcagggcaatggtttctgtctgggccaactgaacagcgataataaaagccag
D  L  P  Q  G  N  G  F  C  L  G  Q  L  N  S  D  N  K  S  Q ctggtgcaaaaagttcgcagcaaaattggctgcggtatccagctgacccgtgaagttgac
L  V  Q  K  V  R  S  K  I  G  C  G  I  Q  L  T  R  E  V  D ggtgtctgggtatataaccgcagcagctacccgatttttatcaaaagcgccacccTggat
G  V  W  V  Y  N  R  S  S  Y  P  I  F  I  K  S  A  T  L  D aatccggacagccgtacgctgctggtccataaagtatttccgggcttcagcatcaaagcg
N  P  D  S  R  T  L  L  V  H  K  V  F  P  G  F  S  I  K  A ttcgattacgagaaagcctacagcctgcagcgcccgaacgaccatgaattcatgcagcaa
F  D  Y  E  K  A  Y  S  L  Q  R  P  N  D  H  E  F  M  Q  Q -continued

```
ccgtggacgggttttactgtgcagatcagcttcgttaaaggctggggtcaatgctacacc
```
P W T G F T V Q I S F V K G W G Q C Y T

```
cgtcagtttatcagcagctgtccgtgctggctggaagtgattttcaatagccgcaagggc
```
R Q F I S S C P W L E V I F N S R *K G*

```
gagctcaatagcaagcttgaaggtaagcctatccctaaccctctcctcggtctcgatagc
```
*E L N S K L E* G K P I P N P L L G L D S acgtgagtcgac (SEQ ID NO: 30)

T-(SEQ ID NO: 31)

The optimized nucleotide and amino acid sequences will also be used to make a variety of N-terminal and C-terminal Tat-Smad7 fragments. Representative examples are provided below.

The Tat-N-Smad7-V5 most optimized nucleotide and amino acid sequences are provided. The protein sequence includes the V5 epitope, which is indicated by bold capital letters.

```
ggatccggccgtaaaaaacgccgtcaacgccgccgtggtttccgtacgaaacgcagcgcc
```
G S G R K K R R Q R R R G F R T K R S A

```
ctggtccgtcgcctgtggcgcagccgtgctccggggtggtgaagatgaagaagaaggtgct
```
L V R R L W R S R A P G G E D E E E G A

```
ggcggcggtggcggtggcggtgaactgcgtggcgagggtgcaaccgatagccgtgcacat
```
G G G G G G G E L R G E G A T D S R A H

```
ggtgcaggcggtggcggtccgggtcgtgctggttgctgtctgggtaaagctgtgcgcggc
```
G A G G G G P G R A G C C L G K A V R G

```
gcgaaaggtcatcatcatccgcatccgccggcagcaggtgcaggtgcagctggcggtgcg
```
A K G H H H P H P P A A G A G A A G G A

```
gaagccgatctgaaagccctgacccatagcgtcctgaaaaaactgaaagaacgtcagctg
```
E A D L K A L T H S V L K K L K E R Q L

```
gagctgctgctgcaagcagtagaaagccgtggcggtacccgtacggcttgtctgctgctg
```
E L L L Q A V E S R G G T R T A C L L L

```
ccgggtcgtctggattgccgtctgggtccgggtgcaccggctggtgcgcagccggcacaa
```
P G R L D C R L G P G A P A G A Q P A Q

```
ccgccgagcagctacagcctgccgctgctgctgtgtaaagtgtttcgttggccggacctg
```
P P S S Y S L P L L L C K V F R W P D L

```
cgccatagcagcgaagttaaacgcctgtgctgttgcgagagctatggcaaaattaacccg
```
R H S S E V K R L C C C E S Y G K I N P

```
gaactggtttgttgcaatccgcatcatctgagccgtctgtgtgaactggagagcccgccg
```
E L V C C N P H H L S R L C E L E S P P

```
ccgccgtatagccgttacccgatggatttcctgaaaccgactgcagattgcccggacgca
```
P P Y S R Y P M D F L K P T A D C P D A

```
gtcccgagcagcgctgagaccggcggcaccaactatctggcaccgggcggtctgagcgat
```
V P S S A E T G G T N Y L A P G G L S D
```

```
agccagctgctgctggaaccgggcgaccgtggtaagcctatccctaaccctctcctcgt
```

S Q L L L E P G D R G K P I P N P L L G

```
ctcgattctacgtgagtcgac (SEQ ID NO: 32)
```

L D S T- (SEQ ID NO: 27)

Tat-C-Smad7-V5 most optimized nucleotide and amino acid sequences are provided. The protein sequence includes the V5 epitope (indicated by bold capital letters), and the pET101-Topo backbone (indicated by underlined italics).

```
ggatccggccgtaaaaaacgccgtcaacgccgccgttcacattggtgtgtggttgcctat
```

G S G R K K R R Q R R R S H W C V V A Y

```
tgggaagagaaaacgcgtgtcggtcgcctgtactgcgtacaggaaccgagcctggatatc
```

W E E K T R V G R L Y C V Q E P S L D I

```
ttttatgacctgccgcagggcaatggtttctgtctgggccaactgaacagcgataataaa
```

F Y D L P Q G N G F C L G Q L N S D N K

```
agccagctggtgcaaaaagttcgcagcaaaattggctgcggtatccagctgacccgtgaa
```

S Q L V Q K V R S K I G C G I Q L T R E

```
gttgacggtgtctgggtatataaccgcagcagctacccgattttatcaaaagcgccacc
```

V D G V W V Y N R S S Y P I F I K S A T

```
ctggataatccggacagccgtacgctgctggtccataaagtatttccgggcttcagcatc
```

L D N P D S R T L L V H K V F P G F S I

```
aaagcgttcgattacgagaaagcctacagcctgcagcgcccgaacgaccatgaattcatg
```

K A F D Y E K A Y S L Q R P N D H E F M

```
cagcaaccgtggacgggttttactgtgcagatcagcttcgttaaaggctggggtcaatgc
```

Q Q P W T G F T V Q I S F V K G W G Q C

```
tacacccgtcagtttatcagcagctgtccgtgctggctggaagtgattttcaatagccgc
```

Y T R Q F I S S C P C W L E V I F N S R

```
aagggcgagctcaatagcaagcttgaaggtaagcctatccctaaccctctcctcggtctc
```

*<u>K G E L N S K L E</u>* G K P I P N P L L G L

```
gatagcacgtgagtcgac (SEQ ID NO: 34)
```

D S T- (SEQ ID NO: 25)

The comparisons before and after the above optimizations are provided below. C-terminal optimization (top strand) (alignment discloses SEQ ID NOS 34 and 24, respectively, in order of appearance):

```
Alignment: Local DNA homologies.
Parameters: Both strands. Method: FastScan-Max Score
   Mol 1 Tat-C-Smad7-ser-his optimized (1-618) Mol 2 Tat-C-termal Smad7-V5 (1-618)
   Number of sequences to align: 2
   Settings: Similarity significance value cutoff: >=60%
Homology Block: Percent Matches 93 Score 541 Length 618
Tat-C-Smad7-    1   ggatccggccgtaaaaaacgccgtcaacgccgccgttcacattggtgtgtggttgcctat
Tat-C-termal    1   ............................................................

Tat-C-Smad7-   61   tgggaagagaaaacgcgtgtcggtcgcctgtactgcgtacaggaaccgagcctggatatc
Tat-C-termal   61   ...............................................tcg..........
```

```
Tat-C-Smad7-   121   ttttatgacctgccgcagggcaatggtttctgtctgggccaactgaacagcgataataaa
Tat-C-termal   121   ..............................................tca.........

Tat-C-Smad7-   181   agccagctggtgcaaaaagttcgcagcaaaattggctgcggtatccagctgacccgtgaa
Tat-C-termal   181   tcg.............................tca.........................

Tat-C-Smad7-   241   gttgacggtgtctgggtatataaccgcagcagctacccgattttttatcaaaaggccacc
Tat-C-termal   241   ..............................tct.....................t.....

Tat-C-Smad7-   301   ctggataatccggacagccgtacgctgctggtccataaagtatttccgggcttcagcatc
Tat-C-termal   301   ..............tc................c................tca...

Tat-C-Smad7-   361   aaagcgttcgattacgagaaagcctacagcctgcagcgcccgaacgaccatgaattcatg
Tat-C-termal   361   ...............................tcg..........................

Tat-C-Smad7-   421   cagcaaccgtggacgggttttactgtgcagatcagcttcgttaaaggctggggtcaatgc
Tat-C-termal   421   ...............................tct..........................

Tat-C-Smad7-   481   tacacccgtcagtttatcagcagctgtccgtgctggctggaagtgattttcaatagccgc
Tat-C-termal   481   .................tcgtc......................................

Tat-C-Smad7-   541   aagggcgagctcaatagcaagcttgaaggtaagcctatccctaaccctctcctcggtctc
Tat-C-termal   541   ...............tcg...........................................

Tat-C-Smad7-   601   gatagcacgtgagtcgac
Tat-C-termal   601   ...tct............
```

N-terminal optimization (top strand) (alignment discloses
SEQ ID NOS 32 and 26, respectively, in order of appearance):

```
Alignment: Local DNA homologies.
Parameters: Both strands. Method: FastScan-Max Score
    Mol 1 Tat-N-Smad7-V5-Ser-His optimized (1-861) Mol 2 Tat-N-Smad7-V5 (1-861)
    Number of sequences to align: 2
    Settings: Similarity significance value cutoff: >=60%
Homology Block: Percent Matches 95 Score 781 Length 861
Tat-N-Smad7-     1   ggatccggccgtaaaaaacgccgtcaacgccgccgtggtttccgtacgaaacgcagcgcc
Tat-N-Smad7-     1   ..........................................................tcg...

Tat-N-Smad7-    61   ctggtccgtcgcctgtggcgcagccgtgctccgggtggtgaagatgaagaagaaggtgct
Tat-N-Smad7-    61   ......................tc...................................

Tat-N-Smad7-   121   ggcggcggtggcggtggcggtgaactgcgtggcgagggtgcaaccgatagccgtgcacat
Tat-N-Smad7-   121   ..............................................t........c Tat-N-Smad7-   181   ggtgcaggcggtggcggtccgggtcgtgctggttgctgtctgggtaaagctgtgcgcggc
Tat-N-Smad7-   181   ............................................................

Tat-N-Smad7-   241   gcgaaaggtcatcatcatccgcatccgccggcagcaggtgcaggtgcagctggcggtgcg
Tat-N-Smad7-   241   ..............c........c....................................

Tat-N-Smad7-   301   gaagccgatctgaaagccctgacccatagcgtcctgaaaaaactgaaagaacgtcagctg
Tat-N-Smad7-   301   ......................................t.....................

Tat-N-Smad7-   361   gagctgctgctgcaagcagtagaaagccgtggcggtacccgtacggcttgtctgctgctg
Tat-N-Smad7-   361   .............................tc.............................

Tat-N-Smad7-   421   ccgggtcgtctggattgccgtctgggtccgggtgcaccggctggtgcgcagccggcacaa
Tat-N-Smad7-   421   ............................................................

Tat-N-Smad7-   481   ccgccgagcagctacagcctgccgctgctgctgtaaagtgtttcgttggccggacctg
Tat-N-Smad7-   481   ..............tct............................................

Tat-N-Smad7-   541   cgccatagcagcgaagttaaacgcctgtgctgttgcgagagctatggcaaaattaacccg
Tat-N-Smad7-   541   .....c..ttc..................................................

Tat-N-Smad7-   601   gaactggtttgttgcaatccgcatcatctgagccgtctgtgtgaactggagagcccgccg
Tat-N-Smad7-   601   ........................c......tct..........................
```

```
Tat-N-Smad7-  661  ccgccgtatagccgttacccgatggatttcctgaaaccgactgcagattgcccggacgca
Tat-N-Smad7-  661  .........tct................................................

Tat-N-Smad7-  721  gtcccgagcagcgctgagaccggcggcaccaactatctggcaccgggcggtctgagcgat
Tat-N-Smad7-  721  ......tcatcg..........................................t....

Tat-N-Smad7-  781  agccagctgctgctggaaccgggcgaccgtggtaagcctatccctaaccctctcctcggt
Tat-N-Smad7-  781  tc..........................................................

Tat-N-Smad7-  841  ctcgattctacgtgagtcgac
Tat-N-Smad7-  841  .....................
```

In addition, other codon-optimized nucleic acids will also be assessed for their ability to produce Smad7 protein in one or more expression systems. Provided below is another example of such a sequence.

Tat-Smad7$^{M7216L}$-V5 optimized by Optimizer program:

```
ggatccggtcgtaaaaaacgtcgtcagcgtcgtcgtggtttccgtaccaaacgttctgcg
 G  S  G  R  K  K  R  R  Q  R  R  R  G  F  R  T  K  R  S  A ctggttcgtcgtctgtggcgttctcgtgcgccgggtggtgaagacgaagaagaaggtgcg
 L  V  R  R  L  W  R  S  R  A  P  G  G  E  D  E  E  E  G  A ggtggtggtggtggtggtggtgaactgcgtggtgaaggtgcgaccgactctcgtgcgcac
 G  G  G  G  G  G  G  E  L  R  G  E  G  A  T  D  S  R  A  H ggtgcgggtggtggtggtccgggtcgtgcgggttgctgcctgggtaaagcggttcgtggt
 G  A  G  G  G  G  P  G  R  A  G  C  C  L  G  K  A  V  R  G gcgaaaggtcaccaccacccgcacccgccggcggcgggtgcgggtgcggcgggtggtgcg
 A  K  G  H  H  H  P  H  P  P  A  A  G  A  G  A  A  G  G  A gaagcggacctgaaagcgctgacccactctgttctgaaaaaactgaaagaacgtcagctg
 E  A  D  L  K  A  L  T  H  S  V  L  K  K  L  K  E  R  Q  L gaactgctgctgcaggcggttgaatctcgtggtggtacccgtaccgcgtgcctgctgctg
 E  L  L  L  Q  A  V  E  S  R  G  G  T  R  T  A  C  L  L  L ccgggtcgtctggactgccgtctgggtccgggtgcgccggcgggtgcgcagccggcgcag
 P  G  R  L  D  C  R  L  G  P  G  A  P  A  G  A  Q  P  A  Q ccgccgtcttcttactctctgccgctgctgctgtgcaaagttttccgttggccggacctg
 P  P  S  S  Y  S  L  P  L  L  L  C  K  V  F  R  W  P  D  L cgtcactcttctgaagttaaacgtctgtgctgctgcgaatcttacggtaaaatcaacccg
 R  H  S  S  E  V  K  R  L  C  C  C  E  S  Y  G  K  I  N  P gaactggtttgctgcaacccgcaccacctgtctcgtctgtgcgaactggaatctccgccg
 E  L  V  C  C  N  P  H  H  L  S  R  L  C  E  L  E  S  P  P ccgccgtactctcgttacccgctggacttcctgaaaccgaccgcggactgcccggacgcg
 P  P  Y  S  R  Y  P  L  D  F  L  K  P  T  A  D  C  P  D  A gttccgtcttctgcggaaaccggtggtaccaactacctggcgccgggtggtctgtctgac
 V  P  S  S  A  E  T  G  G  T  N  Y  L  A  P  G  G  L  S  D tctcagctgctgctggaaccgggtgaccgttctcactggtgcgttgttgcgtactgggaa
 S  Q  L  L  L  E  P  G  D  R  S  H  W  C  V  V  A  Y  W  E
```

```
gaaaaaacccgtgttggtcgtctgtactgcgttcaggaaccgtctctggacatcttctac
 E  K  T  R  V  G  R  L  Y  C  V  Q  E  P  S  L  D  I  F  Y gacctgccgcagggtaacggtttctgcctgggtcagctgaactctgacaacaaatctcag
 D  L  P  Q  G  N  G  F  C  L  G  Q  L  N  S  D  N  K  S  Q ctggttcagaaagttcgttctaaaatcggttgcggtatccagctgacccgtgaagttgac
 L  V  Q  K  V  R  S  K  I  G  C  G  I  Q  L  T  R  E  V  D ggtgtttgggtttacaaccgttcttcttacccgatcttcatcaaatctgcgaccctggac
 G  V  W  V  Y  N  R  S  S  Y  P  I  F  I  K  S  A  T  L  D aacccggactctcgtaccctgctggttcacaaagttttcccgggtttctctatcaaagcg
 N  P  D  S  R  T  L  L  V  H  K  V  F  P  G  F  S  I  K  A ttcgactacgaaaaagcgtactctctgcagcgtccgaacgaccacgaattcatgcagcag
 F  D  Y  E  K  A  Y  S  L  Q  R  P  N  D  H  E  F  M  Q  Q ccgtggaccggtttcaccgttcagatctctttcgttaaaggttgggtcagtgctacacc
 P  W  T  G  F  T  V  Q  I  S  F  V  K  G  W  G  Q  C  Y  T cgtcagttcatctcttcttgcccgtgctggctggaagttatcttcaactctcgtggtaaa
 R  Q  F  I  S  S  C  P  W  L  E  V  I  F  N  S  R  G  K ccgatcccgaacccgctgctgggtctggactctacctgagtcgac (SEQ ID NO: 36)
 P  I  P  N  P  L  L  G  L  D  S  T--(SEQ ID NO: 37)
```

Nucleotide Sequence:
1-6: BamHI; 7-36: Tat; 37-1314: codon-optimized human Smad7; 1315-1356: V5; 137-1359: stop; 1360-1365 SalI ATG is removed to be used with GST; 682 ATG to CTG (M216 to L)

(SEQ ID NO: 36)

```
   1  ggatccggtc gtaaaaaacg tcgtcagcgt cgtcgtggtt
      tccgtaccaa acgttctgcg
  61  ctggttcgtc gtctgtggcg ttctcgtgcg ccgggtggtg
      aagacgaaga agaaggtgcg
 121  ggtggtggtg gtggtggtgg tgaactgcgt ggtgaaggtg
      cgaccgactc tcgtgcgcac
 181  ggtgcgggtg gtggtggtcc gggtcgtgcg ggttgctgcc
      tgggtaaagc ggttcgtggt
 241  gcgaaaggtc accaccaccc gcacccgccg gcggcgggtg
      cgggtgcggc gggtggtgcg
 301  gaagcggacc tgaaagcgct gacccactct gttctgaaaa
      aactgaaaga acgtcagctg
 361  gaactgctgc tgcaggcggt tgaatctcgt ggtggtaccc
      gtaccgcgtg cctgctgctg
 421  ccgggtcgtc tggactgccg tctgggtccg ggtgcgccgg
      cgggtgcgca gccggcgcag
 481  ccgccgtctt cttactctct gccgctgctg ctgtgcaaag
      ttttccgttg gccggacctg
 541  cgtcactctt ctgaagttaa acgtctgtgc tgctgcgaat
      cttacggtaa aatcaacccg
 601  gaactggttt gctgcaaccc gcaccacctg tctcgtctgt
      gcgaactgga atctccgccg
 661  ccgcgtact ctcgttaccc gctggacttc ctgaaaccga
      ccgcggactg cccggacgcg
 721  gttccgtctt ctgcggaaac cggtggtacc aactacctgg
      cgccgggtgg tctgtctgac
 781  tctcagctgc tgctggaacc gggtgaccgt tctcactggt
      gcgttgttgc gtactgggaa
 841  gaaaaaaccc gtgttggtcg tctgtactgc gttcaggaac
      cgtctctgga catcttctac
 901  gacctgccgc agggtaacgg tttctgcctg ggtcagctga
      actctgacaa caaatctcag
 961  ctggttcaga aagttcgttc taaaatcggt tgcggtatcc
      agctgacccg tgaagttgac
1021  ggtgtttggg tttacaaccg ttcttcttac ccgatcttca
      tcaaatctgc gaccctggac
1081  aacccggact ctcgtaccct gctggttcac aaagttttcc
      cgggtttctc tatcaaagcg
1141  ttcgactacg aaaaagcgta ctctctgcag cgtccgaacg
      accacgaatt catgcagcag
1201  ccgtggaccg gtttcaccgt tcagatctct ttcgttaaag
      gttgggtca gtgctacacc
1261  cgtcagttca tctcttcttg cccgtgctgg ctggaagtta
      tcgac
```

Sequence comparison with Tat-Smad7$^{M7216L}$-V5 described in Example 4 (alignment discloses SEQ ID NOS 36 and 30, respectively, in order of appearance):

```
Alignment: Global DNA alignment against reference molecule
Parameters: Scoring matrix: Linear (Mismatch 2, OpenGap 4, ExtGap 1)
    Reference molecule: Tat-Smad7-216L-V5-optimizer, Region 1-1365
    Number of sequences to align: 2
    Settings: Similarity significance value cutoff: >=60%
Summary of Percent Matches:
    Reference: Tat-Smad7-216L-V5-optimizer 1-1365 (1365 bps) —
    Sequence 2: TatSmad7 Ser-His optimized-682 mutant 1-1392 (1392 bps) 79%

Tat-Smad7-21    1 ggatccggtcgtaaaaaacgtcgtcagcgtcgtcgtggtttccgtaccaaacgttctgcg
TatSmad7 Ser    1 ggatccggccgtaaaaaacgccgtcaacgccgccgtggtttccgtacgaaacgcagcgcc Tat-Smad7-21   61 ctggttcgtcgtctgtggcgttctcgtgcgccgggtggtgaagacgaagaagaaggtgcg
TatSmad7 Ser   61 ctggtccgtcgcctgtggcgcagccgtgctccgggtggtgaagatgaagaagaaggtgct Tat-Smad7-21  121 ggtggtggtggtggtggtggtgaactgcgtggtgaaggtgcgaccgactctcgtgcgcac
TatSmad7 Ser  121 ggcggcggtggcgtggcggtgaactgcgtggcgagggtgcaaccgatagccgtgcacat Tat-Smad7-21  181 ggtgcgggtggtggtggtccgggtcgtgcgggttgctgcctgggtaaagcggttcgtggt
TatSmad7 Ser  181 ggtgcaggcggtggcggtccgggtcgtgctggttgctgtctgggtaaagctgtgcgcggc Tat-Smad7-21  241 gcgaaaggtcaccaccaccgcaccgccggcggcgggtgcgggtgcggcgggtggtgcg
TatSmad7 Ser  241 gcgaaaggtcatcatcatccgcatccgccggcagcaggtgcaggtgcagctggcggtgcg Tat-Smad7-21  301 gaagcggacctgaaagcgctgacccactctgttctgaaaaaaactgaaagaacgtcagctg
TatSmad7 Ser  301 gaagccgatctgaaagcgcctgacccatagcgtcctgaaaaaaactgaaagaacgtcagctg Tat-Smad7-21  361 gaactgctgctgcaggcggttgaatctcgtggtggtacccgtaccgcgtgcctgctgctg
TatSmad7 Ser  361 gagctgctgctgcaagcagtagaaagccgtggcggtacccgtacggcttgtctgctgctg Tat-Smad7-21  421 ccgggtcgtctggactgccgtctgggtccgggtgccgccggcgggtgcgcagccggcgcag
TatSmad7 Ser  421 ccgggtcgtctggattgccgtctgggtccgggtgcaccggcggtgcgcagccggcacaa Tat-Smad7-21  481 ccgccgtcttcttactctctgccgctgctgctgtgcaaagttttccgttggccggacctg
TatSmad7 Ser  481 ccgccgagcagctacagcctgccgctgctgctgtgtaaagtgtttcgttggccggacctg Tat-Smad7-21  541 cgtcactcttctgaagttaaacgtctgtgctgctgcgaatcttacggtaaaatcaacccg
TatSmad7 Ser  541 cgccatagcagcgaagttaaacgcctgtgctgttgcgagagctatggcaaaattaacccg Tat-Smad7-21  601 gaactggtttgctgcaacccgcaccacctgtctcgtctgtgcgaactggaatctccgccg
TatSmad7 Ser  601 gaactggtttgttgcaatccgcatcatctgagccgtctgtgtgaactggagagcccgccg Tat-Smad7-21  661 ccgccgtactctcgttacccgctggacttcctgaaaccgacgcggactgcccggacgcg
TatSmad7 Ser  661 ccgccgtatagccgttacccgctggattttcctgaaaccgactgcagattgcccggacgca Tat-Smad7-21  721 gttccgtcttctgcggaaaccggtggtaccaactacctggcgccgggtggtctgtctgac
TatSmad7 Ser  721 gtcccgagcagcgctgagaccggcggcaccaactatctggcaccgggcggtctgagcgat Tat-Smad7-21  781 tctcagctgctgctggaaccgggtgaccgttctcactggtgcgttgttgcgtactgggaa
TatSmad7 Ser  781 agccagctgctgctggaaccgggcgaccgtagccattggtgtgtggttgcctattgggaa Tat-Smad7-21  841 gaaaaaaccgtgttggtcgtctgtactgcgttcaggaaccgtctctggacatcttctac
TatSmad7 Ser  841 gagaaaacgcgtgtcggtcgcctgtactgcgtacaggaaccgagcctggatatctttat Tat-Smad7-21  901 gacctgccgcagggtaacggtttctgcctgggtcagctgaactctgacaacaaatctcag
TatSmad7 Ser  901 gacctgccgcagggcaatggtttctgtctgggccaactgaacagcgataataaaagccag Tat-Smad7-21  961 ctggttcagaaagttcgttctaaaatcggttgcgggtatccagctgaccgtgaagttgac
TatSmad7 Ser  961 ctggtgcaaaaagttcgcagcaaaattggctgcgggtatccagctgaccgtgaagttgac Tat-Smad7-21 1021 ggtgtttgggtttacaaccgttcttcttacccgatcttcatcaaatctgcgaccctggac
TatSmad7 Ser 1021 ggtgtctgggtatataaccgcagcagctacccgattttttatcaaaagcgccaccctggat Tat-Smad7-21 1081 aacccggactctcgtaccctgctggtttcacaaagttttccccggggtttctctatcaaagcg
TatSmad7 Ser 1081 aatccggacagccgtacgctgctggtccataaagtatttccgggcttcagcatcaaagcg Tat-Smad7-21 1141 ttcgactacgaaaaagcgtactctctgcagcgtccgaacgaccacgaattcatgcagcag
TatSmad7 Ser 1141 ttcgattacgagaaagcctacagcctgcagcgcccgaacgaccatgaattcatgcagcaa Tat-Smad7-21 1201 ccgtggaccggtttcaccgttcagatctcttttcgttaaaggttggggtcagtgctacacc
TatSmad7 Ser 1201 ccgtggacgggttttactgtgcagatcagcttcgttaaaggctggggtcaatgctacacc Tat-Smad7-21 1261 cgtcagttcatctcttcttgcccgtgctggctggaagttatcttcaactctcgt------
TatSmad7 Ser 1261 cgtcagtttatcagcagctgtccgtgctggctggaagtgattttcaatagccgcaagggc
```

```
Tat-Smad7-21  1315 --------------------ggtaaaccgatcccgaacccgctgctgggtctggactct
TatSmad7 Ser  1321 gagctcaatagcaagcttgaaggtaagcctatccctaaccctctcctcggtctcgatagc Tat-Smad7-21  1354 acctgagtcgac
TatSmad7 Ser  1381 acgtgagtcgac
```

The foregoing discussion of the present technology has been presented for purposes of illustration and description. The foregoing is not intended to limit the present technology to the form or forms disclosed herein. Although the description of the present technology has included description of one or more embodiments and certain variations and modifications, other variations and modifications are within the scope of the present technology, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

```

What is claimed is:

1. A protein comprising a functional Smad7 domain, wherein the functional Smad7 domain consists of the amino acid sequence as set forth in SEQ ID NO: 12 with a Met216Leu substitution, and wherein the protein antagonizes TGF-β signaling comparable to wild-type Smad7.

2. The protein of claim 1, further comprising a protein transduction domain.

3. The protein of claim 2, wherein the protein transduction domain is a variant of TAT protein from HIV or HSV VP16.

4. The protein of claim 1, further comprising one or more of an epitope tag or a purification tag.

5. A protein comprising a functional Smad7 domain, wherein the functional Smad7 domain consists of amino acids 2 to 258 of the amino acid sequence as set forth in SEQ ID NO: 12 with a Met216Leu substitution.

6. The protein of claim 5, further comprising a protein transduction domain.

7. The protein of claim 6, wherein the protein transduction domain is a variant of TAT protein from HIV or HSV VP16.

8. The protein of claim 5, further comprising one or more of an epitope tag or a purification tag.

9. The protein of claim 5, wherein the functional Smad7 domain has one or more biological activities selected from the group consisting of mediating cell migration, promoting cell proliferation, reducing radiation-induced DNA damage, and blocking fibrotic response.

10. A method for preventing or treating a disease or disorder in a subject comprising one or more of increasing one or more of cell proliferation or cell migration, or preventing one or more of apoptosis or DNA damage in the subject comprising providing to the subject a therapeutically effective amount of a pharmaceutical composition comprising the protein molecule of claim 1, wherein one or more of increasing one or more of cell proliferation or cell migration, or preventing one or more of apoptosis or DNA damage is useful in preventing or treating the disease or disorder.

11. The method of claim 10, wherein the disease or disorder includes one or more of chronic wounds, acute wounds, or mucositis.

* * * * *

                              SEQUENCE LISTING

<160> NUMBER OF SEQ ID NOS: 87

<210> SEQ ID NO 1
<211> LENGTH: 30
<212> TYPE: DNA
<213> ORGANISM: Human immunodeficiency virus
<220> FEATURE:
<221> NAME/KEY: CDS
<222> LOCATION: (1)..(30)

<400> SEQUENCE: 1 ggc cgt aaa aaa cgc cgt caa cgc cgc cgt                              30
Gly Arg Lys Lys Arg Arg Gln Arg Arg Arg
1               5                   10

<210> SEQ ID NO 2
<211> LENGTH: 10
<212> TYPE: PRT
<213> ORGANISM: Human immunodeficiency virus

<400> SEQUENCE: 2

Gly Arg Lys Lys Arg Arg Gln Arg Arg Arg
1               5                   10

<210> SEQ ID NO 3
<211> LENGTH: 33
<212> TYPE: DNA
<213> ORGANISM: Human immunodeficiency virus

<400> SEQUENCE: 3
tatggccgta aaaacgccg tcaacgccgc cgt                                  33

<210> SEQ ID NO 4
<211> LENGTH: 11
<212> TYPE: PRT
<213> ORGANISM: Human immunodeficiency virus

<400> SEQUENCE: 4

Tyr Gly Arg Lys Lys Arg Arg Gln Arg Arg Arg
1               5                   10

<210> SEQ ID NO 5
<211> LENGTH: 21
<212> TYPE: DNA
<213> ORGANISM: Human immunodeficiency virus

<400> SEQUENCE: 5
```

```
ggccgtaaaa aacgccgtca a                                              21

<210> SEQ ID NO 6
<211> LENGTH: 7
<212> TYPE: PRT
<213> ORGANISM: Human immunodeficiency virus

<400> SEQUENCE: 6

Gly Arg Lys Lys Arg Arg Gln
1               5

<210> SEQ ID NO 7
<211> LENGTH: 30
<212> TYPE: DNA
<213> ORGANISM: Human immunodeficiency virus

<400> SEQUENCE: 7
ggccgtaaaa aacgccgtca acgccgccgt                                     30

<210> SEQ ID NO 8
<211> LENGTH: 30
<212> TYPE: DNA
<213> ORGANISM: Human immunodeficiency virus

<400> SEQUENCE: 8
ggccgtaaaa aacgccgtca acgccgccgt                                     30

<210> SEQ ID NO 9
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (58)..(1461)

<400> SEQUENCE: 9
ttcccctcta gaataatttt tgtttaactt taagaaggaa ttcaggagcc cttcacc        57 atg cgt aaa aaa cgc cgt caa cgc cgt cgt ggt ttc cgt acg aaa cgc     105
Met Arg Lys Lys Arg Arg Gln Arg Arg Arg Gly Phe Arg Thr Lys Arg
1               5                   10                  15 tcg gcc ctg gtc cgt cgc ctg tgg cgc tcc cgt gct ccg ggt ggt gaa     153
Ser Ala Leu Val Arg Arg Leu Trp Arg Ser Arg Ala Pro Gly Gly Glu
            20                  25                  30 gat gaa gaa gaa ggt gct ggc ggc ggt ggc ggt ggc ggt gaa ctg cgt     201
Asp Glu Glu Glu Gly Ala Gly Gly Gly Gly Gly Gly Gly Glu Leu Arg
        35                  40                  45 ggc gag ggt gca acc gat agt cgt gca cac ggt gca ggc ggt ggc ggt     249
Gly Glu Gly Ala Thr Asp Ser Arg Ala His Gly Ala Gly Gly Gly Gly
    50                  55                  60 ccg ggt cgt gct ggt tgc tgt ctg ggt aaa gct gtg cgc ggc gcg aaa     297
Pro Gly Arg Ala Gly Cys Cys Leu Gly Lys Ala Val Arg Gly Ala Lys
65                  70                  75                  80 ggt cat cac cat ccg cac ccg ccg gca gca ggt gca ggt gca gct ggc     345
Gly His His His Pro His Pro Pro Ala Ala Gly Ala Gly Ala Ala Gly
                85                  90                  95 ggt gcg gaa gcc gat ctg aaa gcc ctg acc cat agt gtc ctg aaa aaa     393
Gly Ala Glu Ala Asp Leu Lys Ala Leu Thr His Ser Val Leu Lys Lys
            100                 105                 110 ctg aaa gaa cgt cag ctg gag ctg ctg ctg caa gca gta gaa tcc cgt     441
Leu Lys Glu Arg Gln Leu Glu Leu Leu Leu Gln Ala Val Glu Ser Arg
```

```
                    115                 120                 125
ggc ggt acc cgt acg gct tgt ctg ctg ctg ccg ggt cgt ctg gat tgc      489
Gly Gly Thr Arg Thr Ala Cys Leu Leu Leu Pro Gly Arg Leu Asp Cys
        130                 135                 140 cgt ctg ggt ccg ggt gca ccg gct ggt gcg cag ccg gca caa ccg ccg      537
Arg Leu Gly Pro Gly Ala Pro Ala Gly Ala Gln Pro Ala Gln Pro Pro
145                 150                 155                 160 agc tct tac agc ctg ccg ctg ctg tgt aaa gtg ttt cgt tgg ccg          585
Ser Ser Tyr Ser Leu Pro Leu Leu Cys Lys Val Phe Arg Trp Pro
                    165                 170                 175 gac ctg cgc cac agt tcc gaa gtt aaa cgc ctg tgt tgt gag agc          633
Asp Leu Arg His Ser Ser Glu Val Lys Arg Leu Cys Cys Cys Glu Ser
            180                 185                 190 tat ggc aaa att aac ccg gaa ctg gtt tgt tgc aat ccg cac cat ctg      681
Tyr Gly Lys Ile Asn Pro Glu Leu Val Cys Cys Asn Pro His His Leu
                195                 200                 205 tct cgt ctg tgt gaa ctg gag agc ccg ccg ccg tat tct cgt tac          729
Ser Arg Leu Cys Glu Leu Glu Ser Pro Pro Pro Pro Tyr Ser Arg Tyr
        210                 215                 220 ccg atg gat ttc ctg aaa ccg act gca gat tgc ccg gac gca gtc ccg      777
Pro Met Asp Phe Leu Lys Pro Thr Ala Asp Cys Pro Asp Ala Val Pro
225                 230                 235                 240 tca tcg gct gag acc ggc ggc acc aac tat ctg gca ccg ggc ggt ctg      825
Ser Ser Ala Glu Thr Gly Gly Thr Asn Tyr Leu Ala Pro Gly Gly Leu
                    245                 250                 255 agt gat tcc cag ctg ctg ctg gaa ccg ggc gac cgt tca cat tgg tgt      873
Ser Asp Ser Gln Leu Leu Leu Glu Pro Gly Asp Arg Ser His Trp Cys
            260                 265                 270 gtg gtt gcc tat tgg gaa gag aaa acg cgt gtc ggt cgc ctg tac tgc      921
Val Val Ala Tyr Trp Glu Glu Lys Thr Arg Val Gly Arg Leu Tyr Cys
                275                 280                 285 gta cag gaa ccg tcg ctg gat atc ttt tat gac ctg ccg cag ggc aat      969
Val Gln Glu Pro Ser Leu Asp Ile Phe Tyr Asp Leu Pro Gln Gly Asn
        290                 295                 300 ggt ttc tgt ctg ggc caa ctg aac tca gat aat aaa tcg cag ctg gtg     1017
Gly Phe Cys Leu Gly Gln Leu Asn Ser Asp Asn Lys Ser Gln Leu Val
305                 310                 315                 320 caa aaa gtt cgc tca aaa att ggc tgc ggt atc cag ctg acc cgt gaa     1065
Gln Lys Val Arg Ser Lys Ile Gly Cys Gly Ile Gln Leu Thr Arg Glu
                    325                 330                 335 gtt gac ggt gtc tgg gta tat aac cgc agc tct tac ccg att ttt atc     1113
Val Asp Gly Val Trp Val Tyr Asn Arg Ser Ser Tyr Pro Ile Phe Ile
            340                 345                 350 aaa agt gcc acc ctg gat aat ccg gac tcc cgt acg ctg ctg gtc cac     1161
Lys Ser Ala Thr Leu Asp Asn Pro Asp Ser Arg Thr Leu Leu Val His
                355                 360                 365 aaa gta ttt ccg ggc ttc tca atc aaa gcg ttc gat tac gag aaa gcc     1209
Lys Val Phe Pro Gly Phe Ser Ile Lys Ala Phe Asp Tyr Glu Lys Ala
        370                 375                 380 tac tcg ctg cag cgc ccg aac gac cat gaa ttc atg cag caa ccg tgg     1257
Tyr Ser Leu Gln Arg Pro Asn Asp His Glu Phe Met Gln Gln Pro Trp
385                 390                 395                 400 acg ggt ttt act gtg cag atc tct ttc gtt aaa ggc tgg ggt caa tgc     1305
Thr Gly Phe Thr Val Gln Ile Ser Phe Val Lys Gly Trp Gly Gln Cys
                    405                 410                 415 tac acc cgt cag ttt atc tcg tcc tgt ccg tgc tgg ctg gaa gtg att     1353
Tyr Thr Arg Gln Phe Ile Ser Ser Cys Pro Cys Trp Leu Glu Val Ile
            420                 425                 430 ttc aat agc cgc aag ggc gag ctc aat tcg aag ctt gaa ggt aag cct     1401
```

```
Phe Asn Ser Arg Lys Gly Glu Leu Asn Ser Lys Leu Glu Gly Lys Pro
            435                 440                 445 atc cct aac cct ctc ctc ggt ctc gat tct acg cgt acc ggt cat cat     1449
Ile Pro Asn Pro Leu Leu Gly Leu Asp Ser Thr Arg Thr Gly His His
450                 455                 460 cac cat cac cat tgagtttgat ccggctgcta acaaagcccg aaagga             1497
His His His His
465

<210> SEQ ID NO 10
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Arg Lys Lys Arg Arg Gln Arg Arg Gly Phe Arg Thr Lys Arg
1               5                   10                  15

Ser Ala Leu Val Arg Arg Leu Trp Arg Ser Arg Ala Pro Gly Gly Glu
                20                  25                  30

Asp Glu Glu Gly Ala Gly Gly Gly Gly Gly Gly Glu Leu Arg
            35                  40                  45

Gly Glu Gly Ala Thr Asp Ser Arg Ala His Gly Ala Gly Gly Gly
50                  55                  60

Pro Gly Arg Ala Gly Cys Cys Leu Gly Lys Ala Val Arg Gly Ala Lys
65                  70                  75                  80

Gly His His His Pro His Pro Ala Ala Gly Ala Gly Ala Ala Gly
                85                  90                  95

Gly Ala Glu Ala Asp Leu Lys Ala Leu Thr His Ser Val Leu Lys Lys
                100                 105                 110

Leu Lys Glu Arg Gln Leu Glu Leu Leu Leu Gln Ala Val Glu Ser Arg
            115                 120                 125

Gly Gly Thr Arg Thr Ala Cys Leu Leu Leu Pro Gly Arg Leu Asp Cys
130                 135                 140

Arg Leu Gly Pro Gly Ala Pro Ala Gly Ala Gln Pro Ala Gln Pro Pro
145                 150                 155                 160

Ser Ser Tyr Ser Leu Pro Leu Leu Leu Cys Lys Val Phe Arg Trp Pro
                165                 170                 175

Asp Leu Arg His Ser Ser Glu Val Lys Arg Leu Cys Cys Cys Glu Ser
            180                 185                 190

Tyr Gly Lys Ile Asn Pro Glu Leu Val Cys Cys Asn Pro His His Leu
            195                 200                 205

Ser Arg Leu Cys Glu Leu Glu Ser Pro Pro Pro Tyr Ser Arg Tyr
210                 215                 220

Pro Met Asp Phe Leu Lys Pro Thr Ala Asp Cys Pro Asp Ala Val Pro
225                 230                 235                 240

Ser Ser Ala Glu Thr Gly Gly Thr Asn Tyr Leu Ala Pro Gly Gly Leu
                245                 250                 255

Ser Asp Ser Gln Leu Leu Leu Glu Pro Gly Asp Arg Ser His Trp Cys
            260                 265                 270

Val Val Ala Tyr Trp Glu Glu Lys Thr Arg Val Gly Arg Leu Tyr Cys
            275                 280                 285

Val Gln Glu Pro Ser Leu Asp Ile Phe Tyr Asp Leu Pro Gln Gly Asn
            290                 295                 300
```

```
Gly Phe Cys Leu Gly Gln Leu Asn Ser Asp Asn Lys Ser Gln Leu Val
305                 310                 315                 320

Gln Lys Val Arg Ser Lys Ile Gly Cys Gly Ile Gln Leu Thr Arg Glu
            325                 330                 335

Val Asp Gly Val Trp Val Tyr Asn Arg Ser Ser Tyr Pro Ile Phe Ile
            340                 345                 350

Lys Ser Ala Thr Leu Asp Asn Pro Asp Ser Arg Thr Leu Leu Val His
            355                 360                 365

Lys Val Phe Pro Gly Phe Ser Ile Lys Ala Phe Asp Tyr Glu Lys Ala
            370                 375                 380

Tyr Ser Leu Gln Arg Pro Asn Asp His Glu Phe Met Gln Gln Pro Trp
385                 390                 395                 400

Thr Gly Phe Thr Val Gln Ile Ser Phe Val Lys Gly Trp Gly Gln Cys
            405                 410                 415

Tyr Thr Arg Gln Phe Ile Ser Ser Cys Pro Cys Trp Leu Glu Val Ile
            420                 425                 430

Phe Asn Ser Arg Lys Gly Glu Leu Asn Ser Lys Leu Gly Lys Pro
            435                 440                 445

Ile Pro Asn Pro Leu Leu Gly Leu Asp Ser Thr Arg Thr Gly His His
450                 455                 460

His His His His
465

<210> SEQ ID NO 11
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ser Gly Arg Lys Lys Arg Gln Arg Arg Gly Phe Arg Thr
1               5                   10                  15

Lys Arg Ser Ala Leu Val Arg Leu Trp Arg Ser Arg Ala Pro Gly
                20                  25                  30

Gly Glu Asp Glu Glu Gly Ala Gly Gly Gly Gly Gly Gly Glu
            35                  40                  45

Leu Arg Gly Glu Gly Ala Thr Asp Ser Arg Ala His Gly Ala Gly Gly
    50                  55                  60

Gly Gly Pro Gly Arg Ala Gly Cys Cys Leu Gly Lys Ala Val Arg Gly
65                  70                  75                  80

Ala Lys Gly His His His Pro His Pro Pro Ala Ala Gly Ala Gly Ala
                85                  90                  95

Ala Gly Gly Ala Glu Ala Asp Leu Lys Ala Leu Thr His Ser Val Leu
            100                 105                 110

Lys Lys Leu Lys Glu Arg Gln Leu Glu Leu Leu Leu Gln Ala Val Glu
            115                 120                 125

Ser Arg Gly Gly Thr Arg Thr Ala Cys Leu Leu Leu Pro Gly Arg Leu
130                 135                 140

Asp Cys Arg Leu Gly Pro Gly Ala Pro Ala Gly Ala Gln Pro Ala Gln
145                 150                 155                 160

Pro Pro Ser Ser Tyr Ser Leu Pro Leu Leu Leu Cys Lys Val Phe Arg
                165                 170                 175

Trp Pro Asp Leu Arg His Ser Ser Glu Val Lys Arg Leu Cys Cys Cys
            180                 185                 190
```

```
Glu Ser Tyr Gly Lys Ile Asn Pro Glu Leu Val Cys Cys Asn Pro His
            195                 200                 205

His Leu Ser Arg Leu Cys Glu Leu Glu Ser Pro Pro Pro Tyr Ser
    210                 215                 220

Arg Tyr Pro Met Asp Phe Leu Lys Pro Thr Ala Asp Cys Pro Asp Ala
225                 230                 235                 240

Val Pro Ser Ser Ala Glu Thr Gly Gly Thr Asn Tyr Leu Ala Pro Gly
                245                 250                 255

Gly Leu Ser Asp Ser Gln Leu Leu Glu Pro Gly Asp Arg Ser His
            260                 265                 270

Trp Cys Val Val Ala Tyr Trp Glu Glu Lys Thr Arg Val Gly Arg Leu
                275                 280                 285

Tyr Cys Val Gln Glu Pro Ser Leu Asp Ile Phe Tyr Asp Leu Pro Gln
            290                 295                 300

Gly Asn Gly Phe Cys Leu Gly Gln Leu Asn Ser Asp Asn Lys Ser Gln
305                 310                 315                 320

Leu Val Gln Lys Val Arg Ser Lys Ile Gly Cys Gly Ile Gln Leu Thr
                325                 330                 335

Arg Glu Val Asp Gly Val Trp Val Tyr Asn Arg Ser Ser Tyr Pro Ile
            340                 345                 350

Phe Ile Lys Ser Ala Thr Leu Asp Asn Pro Asp Ser Arg Thr Leu Leu
            355                 360                 365

Val His Lys Val Phe Pro Gly Phe Ser Ile Lys Ala Phe Asp Tyr Glu
    370                 375                 380

Lys Ala Tyr Ser Leu Gln Arg Pro Asn Asp His Glu Phe Met Gln Gln
385                 390                 395                 400

Pro Trp Thr Gly Phe Thr Val Gln Ile Ser Phe Val Lys Gly Trp Gly
                405                 410                 415

Gln Cys Tyr Thr Arg Gln Phe Ile Ser Ser Cys Pro Cys Trp Leu Glu
            420                 425                 430

Val Ile Phe Asn Ser Arg Lys Gly Glu Leu Asn Ser Lys Leu Glu Gly
            435                 440                 445

Lys Pro Ile Pro Asn Pro Leu Leu Gly Leu Asp Ser Thr
            450                 455                 460

<210> SEQ ID NO 12
<211> LENGTH: 426
<212> TYPE: PRT
<213> ORGANISM: Homo sapiens

<400> SEQUENCE: 12

Met Phe Arg Thr Lys Arg Ser Ala Leu Val Arg Arg Leu Trp Arg Ser
1               5                   10                  15

Arg Ala Pro Gly Gly Glu Asp Glu Glu Gly Ala Gly Gly Gly
            20                  25                  30

Gly Gly Gly Glu Leu Arg Gly Gly Ala Thr Asp Ser Arg Ala His
        35                  40                  45

Gly Ala Gly Gly Gly Pro Gly Arg Ala Gly Cys Cys Leu Gly Lys
    50                  55                  60

Ala Val Arg Gly Ala Lys Gly His His His Pro Pro Ala Ala
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu Leu
```

```
            100                 105                 110
    Gln Ala Val Glu Ser Arg Gly Gly Thr Arg Thr Ala Cys Leu Leu Leu
            115                 120                 125

Pro Gly Arg Leu Asp Cys Arg Leu Gly Pro Gly Ala Pro Ala Gly Ala
130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                    165                 170                 175

Leu Cys Cys Cys Glu Ser Tyr Gly Lys Ile Asn Pro Glu Leu Val Cys
                180                 185                 190

Cys Asn Pro His His Leu Ser Arg Leu Cys Glu Leu Glu Ser Pro Pro
                195                 200                 205

Pro Pro Tyr Ser Arg Tyr Pro Met Asp Phe Leu Lys Pro Thr Ala Asp
            210                 215                 220

Cys Pro Asp Ala Val Pro Ser Ser Ala Glu Thr Gly Gly Thr Asn Tyr
225                 230                 235                 240

Leu Ala Pro Gly Gly Leu Ser Asp Ser Gln Leu Leu Leu Glu Pro Gly
                    245                 250                 255

Asp Arg Ser His Trp Cys Val Val Ala Tyr Trp Glu Glu Lys Thr Arg
                260                 265                 270

Val Gly Arg Leu Tyr Cys Val Gln Glu Pro Ser Leu Asp Ile Phe Tyr
                275                 280                 285

Asp Leu Pro Gln Gly Asn Gly Phe Cys Leu Gly Gln Leu Asn Ser Asp
            290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                    325                 330                 335

Ser Tyr Pro Ile Phe Ile Lys Ser Ala Thr Leu Asp Asn Pro Asp Ser
                340                 345                 350

Arg Thr Leu Leu Val His Lys Val Phe Pro Gly Phe Ser Ile Lys Ala
                355                 360                 365

Phe Asp Tyr Glu Lys Ala Tyr Ser Leu Gln Arg Pro Asn Asp His Glu
            370                 375                 380

Phe Met Gln Gln Pro Trp Thr Gly Phe Thr Val Gln Ile Ser Phe Val
385                 390                 395                 400

Lys Gly Trp Gly Gln Cys Tyr Thr Arg Gln Phe Ile Ser Ser Cys Pro
                    405                 410                 415

Cys Trp Leu Glu Val Ile Phe Asn Ser Arg
                420                 425

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggaattcct ggtctggttt                                              20

<210> SEQ ID NO 14
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 14
gccaagctgc tcttccagta                                               20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctcaggggg ccaaaggtgt t                                             21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcccagcacc tgaatcacat gg                                            22

<210> SEQ ID NO 17
<211> LENGTH: 10
<212> TYPE: DNA
<213> ORGANISM: Unknown
<220> FEATURE:
<223> OTHER INFORMATION: Description of Unknown:
      Smad binding element oligonucleotide

<400> SEQUENCE: 17
tgtctgtgct                                                          10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgatagagct                                                          10

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcctcgagt atcctccagg tctggg                                        26

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccaagctta gcgtccagcg ttaacctg                                        28

<210> SEQ ID NO 21
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ggatccggcc gtaaaaaacg ccgtcaacgc cgccgtggtt tccgtacgaa acgctcggcc       60
ctggtccgtc gcctgtggcg ctcccgtgct ccgggtggtg aagatgaaga agaaggtgct      120
ggcggcggtg gcgtggcgg tgaactgcgt ggcgagggtg caaccgatag tcgtgcacac       180
ggtgcaggcg gtggcggtcc gggtcgtgct ggttgctgtc tgggtaaagc tgtgcgcggc      240
gcgaaaggtc atcaccatcc gcacccgccg gcagcaggtg caggtgcagc tggcggtgcg      300
gaagccgatc tgaaagccct gacccatagt gtcctgaaaa aactgaaaga acgtcagctg      360
gagctgctgc tgcaagcagt agaatcccgt ggcggtaccc gtacggcttg tctgctgctg      420
ccgggtcgtc tggattgccg tctgggtccg ggtgcaccgg ctggtgcgca gccggcacaa      480
ccgccgagct cttacagcct gccgctgctg ctgtgtaaag tgtttcgttg gccggacctg      540
cgccacagtt ccgaagttaa acgcctgtgc tgttgcgaga gctatggcaa aattaacccg      600
gaactggttt gttgcaatcc gcaccatctg tctcgtctgt gtgaactgga gagcccgccg      660
ccgccgtatt ctcgttaccc gatggatttc ctgaaaccga ctgcagattg cccggacgca      720
gtcccgtcat cggctgagac cggcggcacc aactatctgg caccgggcgg tctgagtgat      780
tcccagctgc tgctggaacc gggcgaccgt tcacattggt gtgtggttgc ctattgggaa      840
gagaaaacgc gtgtcggtcg cctgtactgc gtacaggaac cgtcgctgga tatcttttat      900
gacctgccgc agggcaatgg tttctgtctg ggccaactga actcagataa taaatcgcag      960
ctggtgcaaa aagttcgctc aaaaattggc tgcggtatcc agctgacccg tgaagttgac     1020
ggtgtctggg tatataaccg cagctcttac ccgattttta tcaaaagtgc caccctggat    1080
ggtgtctggg tatataaccg cagctcttac ccgattttta tcaaaagtgc caccctggat    1140
aatccggact cccgtacgct gctggtccac aaagtatttc cgggcttctc aatcaaagcg    1200
ccgtggacgg gttttactgt gcagatctct ttcgttaaag ctggggtca atgctacacc    1260 cgtcagttta tctcgtcctg tccgtgctgg ctggaagtga ttttcaatag ccgcaagggc    1320
gagctcaatt cgaagcttga aggtaagcct atccctaacc ctctcctcgg tctcgattct   1380
acgtgagtcg ac                                                         1392

<210> SEQ ID NO 22
<211> LENGTH: 1281
<212> TYPE: DNA
<213> ORGANISM: Homo sapiens

<400> SEQUENCE: 22
atgttcagga ccaaacgatc tgcgctcgtc cggcgtctct ggaggagccg tgcgcccggc       60
ggcgaggacg aggaggaggg cgcaggggga ggtggaggag gaggcgagct gcggggagaa     120

```
ggggcgacgg acagccgagc gcatggggcc ggtggcggcg gcccgggcag ggctggatgc    180
tgcctgggca aggcggtgcg aggtgccaaa ggtcaccacc atccccaccc gccagccgcg    240
ggcgccggcg cggccggggg cgccgaggcg gatctgaagg cgctcacgca ctcggtgctc    300
aagaaactga aggagcggca gctggagctg ctgctccagg ccgtggagtc ccgcggcggg    360
acgcgcaccg cgtgcctcct gctgcccggc cgcctggact gcaggctggg cccggggggcg   420 cccgccggcg cgcagcctgc gcagccgccc tcgtcctact cgctccccct cctgctgtgc    480
aaagtgttca ggtggccgga tctcaggcat tcctcggaag tcaagaggct gtgttgctgt    540
gaatcttacg ggaagatcaa cccccgagctg gtgtgctgca accccatca ccttagccga    600 ctctgcgaac tagagtctcc ccccctcct tactccagat acccgatgga ttttctcaaa     660
ccaactgcag actgtccaga tgctgtgcct tcctccgctg aaacaggggg aacgaattat    720
ctggcccctg gggggctttc agattcccaa cttcttctgg agcctgggga tcggtcacac    780
tggtgcgtgg tggcatactg ggaggagaag acgagagtgg ggaggctcta ctgtgtccag    840
gagccctctc tggatatctt ctatgatcta cctcagggga atggcttttg cctcggacag    900
ctcaattcgg acaacaagag tcagctggtg cagaaggtgc ggagcaaaat cggctgcggc    960
atccagctga cgcgggaggt ggatggtgtg tgggtgtaca accgcagcag ttaccccatc   1020
ttcatcaagt ccgccacact ggacaacccg gactccagga cgctgttggt acacaaggtg   1080
ttccccggtt tctccatcaa ggctttcgac tacgagaagg cgtacagcct gcagcggccc   1140
aatgaccacg agtttatgca gcagccgtgg acgggcttta ccgtgcagat cagctttgtg   1200
aagggctggg gtcagtgcta cacccgccag ttcatcagca gctgcccgtg ctggctagag   1260
gtcatcttca acagccggta g                                             1281

<210> SEQ ID NO 23
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ggatccggcc gtaaaaaacg ccgtcaacgc cgccgtggtt tccgtacgaa acgctcggcc     60
ctggtccgtc gcctgtggcg ctcccgtgct ccgggtggtg aagatgaaga agaaggtgct    120
ggcggcggtg gcggtggcgg tgaactgcgt ggcgagggtg caaccgatag tcgtgcacac    180
ggtgcaggcg gtgcggtcc gggtcgtgct ggttgctgtc tgggtaaagc tgtgcgcggc    240
gcgaaaggtc atcaccatcc gcaccgccg gcagcaggtg caggtgcagc tggcggtgcg    300
gaagccgatc tgaaagccct gacccatagt gtcctgaaaa aactgaaaga acgtcagctg    360
gagctgctgc tgcaagcagt agaatcccgt ggcggtaccc gtacggcttg tctgctgctg    420
ccgggtcgtc tggattgccg tctgggtccg ggtgcaccgg ctggtgcgca gccggcacaa    480
ccgccgagct cttacagcct gccgctgctg ctgtgtaaag tgtttcgttg gccggacctg    540
cgccacagtt ccgaagttaa acgcctgtgc tgttgcgaga gctatggcaa aattaacccg    600
gaactggttt gttgcaatcc gcaccatctg tctcgtctgt gtgaactgga gagcccgccg    660
ccgccgtatt ccgttaccc gatggatttc ctgaaaccga ctgcagattg cccggacgca    720
gtcccgtcat cggctgagac cggcggcacc aactatctgg caccgggcgg tctgagtgat    780
tcccagctgc tgctggaacc gggcgaccgt tcacattggt gtgtggttgc ctattgggaa    840
```

-continued

```
gagaaaacgc gtgtcggtcg cctgtactgc gtacaggaac cgtcgctgga tatctttat      900 gacctgccgc agggcaatgg tttctgtctg ggccaactga actcagataa taaatcgcag      960
ctggtgcaaa aagttcgctc aaaaattggc tgcggtatcc agctgacccg tgaagttgac     1020
ggtgtctggg tatataaccg cagctcttac ccgatttta tcaaaagtgc caccctggat     1080
aatccggact cccgtacgct gctggtccac aaagtatttc cgggcttctc aatcaaagcg     1140
ttcgattacg agaaagccta ctcgctgcag cgcccgaacg accatgaatt catgcagcaa     1200
ccgtggacgg gttttactgt gcagatctct ttcgttaaag ctgggtca atgctacacc     1260 cgtcagttta tctcgtcctg tccgtgctgg ctggaagtga ttttcaatag ccgcaagggc     1320
gagctcaatt cgaagcttga aggtaagcct atccctaacc ctctcctcgg tctcgattct     1380
acgtgagtcg ac                                                          1392
```

<210> SEQ ID NO 24
<211> LENGTH: 618
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(609)

<400> SEQUENCE: 24

```
gga tcc ggc cgt aaa aaa cgc cgt caa cgc cgc cgt tca cat tgg tgt        48
Gly Ser Gly Arg Lys Lys Arg Arg Gln Arg Arg Arg Ser His Trp Cys
1               5                   10                  15 gtg gtt gcc tat tgg gaa gag aaa acg cgt gtc ggt cgc ctg tac tgc        96
Val Val Ala Tyr Trp Glu Glu Lys Thr Arg Val Gly Arg Leu Tyr Cys
                20                  25                  30 gta cag gaa ccg tcg ctg gat atc ttt tat gac ctg ccg cag ggc aat       144
Val Gln Glu Pro Ser Leu Asp Ile Phe Tyr Asp Leu Pro Gln Gly Asn
            35                  40                  45 ggt ttc tgt ctg ggc caa ctg aac tca gat aat aaa tcg cag ctg gtg       192
Gly Phe Cys Leu Gly Gln Leu Asn Ser Asp Asn Lys Ser Gln Leu Val
        50                  55                  60 caa aaa gtt cgc tca aaa att ggc tgc ggt atc cag ctg acc cgt gaa       240
Gln Lys Val Arg Ser Lys Ile Gly Cys Gly Ile Gln Leu Thr Arg Glu
65                  70                  75                  80 gtt gac ggt gtc tgg gta tat aac cgc agc tct tac ccg att ttt atc       288
Val Asp Gly Val Trp Val Tyr Asn Arg Ser Ser Tyr Pro Ile Phe Ile
                85                  90                  95 aaa agt gcc acc ctg gat aat ccg gac tcc cgt acg ctg ctg gtc cac       336
Lys Ser Ala Thr Leu Asp Asn Pro Asp Ser Arg Thr Leu Leu Val His
            100                 105                 110 aaa gta ttt ccg ggc ttc tca atc aaa gcg ttc gat tac gag aaa gcc       384
Lys Val Phe Pro Gly Phe Ser Ile Lys Ala Phe Asp Tyr Glu Lys Ala
        115                 120                 125 tac tcg ctg cag cgc ccg aac gac cat gaa ttc atg cag caa ccg tgg       432
Tyr Ser Leu Gln Arg Pro Asn Asp His Glu Phe Met Gln Gln Pro Trp
    130                 135                 140 acg ggt ttt act gtg cag atc tct ttc gtt aaa gct ggg gtc aa tgc       480
Thr Gly Phe Thr Val Gln Ile Ser Phe Val Lys Gly Trp Gly Gln Cys
145                 150                 155                 160 tac acc cgt cag ttt atc tcg tcc tgt ccg tgc tgg ctg gaa gtg att       528
Tyr Thr Arg Gln Phe Ile Ser Ser Cys Pro Cys Trp Leu Glu Val Ile
                165                 170                 175 ttc aat agc cgc aag ggc gag ctc aat tcg aag ctt gaa ggt aag cct       576
Phe Asn Ser Arg Lys Gly Glu Leu Asn Ser Lys Leu Glu Gly Lys Pro
```

```
Phe Asn Ser Arg Lys Gly Glu Leu Asn Ser Lys Leu Glu Gly Lys Pro
                180                 185                 190 atc cct aac cct ctc ctc ggt ctc gat tct acg tgagtcgac            618
Ile Pro Asn Pro Leu Leu Gly Leu Asp Ser Thr
            195                 200
```

<210> SEQ ID NO 25
<211> LENGTH: 203
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gly Ser Gly Arg Lys Lys Arg Gln Arg Arg Ser His Trp Cys
1               5                   10                  15

Val Val Ala Tyr Trp Glu Glu Lys Thr Arg Val Gly Arg Leu Tyr Cys
                20                  25                  30

Val Gln Glu Pro Ser Leu Asp Ile Phe Tyr Asp Leu Pro Gln Gly Asn
            35                  40                  45

Gly Phe Cys Leu Gly Gln Leu Asn Ser Asp Asn Lys Ser Gln Leu Val
        50                  55                  60

Gln Lys Val Arg Ser Lys Ile Gly Cys Gly Ile Gln Leu Thr Arg Glu
65                  70                  75                  80

Val Asp Gly Val Trp Val Tyr Asn Arg Ser Tyr Pro Ile Phe Ile
                85                  90                  95

Lys Ser Ala Thr Leu Asp Asn Pro Asp Ser Arg Thr Leu Leu Val His
                100                 105                 110

Lys Val Phe Pro Gly Phe Ser Ile Lys Ala Phe Asp Tyr Glu Lys Ala
                115                 120                 125

Tyr Ser Leu Gln Arg Pro Asn Asp His Glu Phe Met Gln Gln Pro Trp
    130                 135                 140

Thr Gly Phe Thr Val Gln Ile Ser Phe Val Lys Gly Trp Gly Gln Cys
145                 150                 155                 160

Tyr Thr Arg Gln Phe Ile Ser Ser Cys Pro Cys Trp Leu Glu Val Ile
                165                 170                 175

Phe Asn Ser Arg Lys Gly Glu Leu Asn Ser Lys Leu Glu Gly Lys Pro
                180                 185                 190

Ile Pro Asn Pro Leu Leu Gly Leu Asp Ser Thr
            195                 200
```

<210> SEQ ID NO 26
<211> LENGTH: 861
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(852)

<400> SEQUENCE: 26

```
gga tcc ggc cgt aaa aaa cgc cgt caa cgc cgt ggt ttc cgt acg        48
Gly Ser Gly Arg Lys Lys Arg Arg Gln Arg Arg Gly Phe Arg Thr
1               5                   10                  15 aaa cgc tcg gcc ctg gtc cgt cgc ctg tgg cgc tcc cgt gct ccg ggt    96
Lys Arg Ser Ala Leu Val Arg Arg Leu Trp Arg Ser Arg Ala Pro Gly
                20                  25                  30
```

```
ggt gaa gat gaa gaa gaa ggt gct ggc ggc ggt ggt ggt ggc ggt gaa        144
Gly Glu Asp Glu Glu Glu Gly Ala Gly Gly Gly Gly Gly Gly Glu
         35                  40                  45 ctg cgt ggc gag ggt gca acc gat agt cgt gca cac ggt gca ggt ggt        192
Leu Arg Gly Glu Gly Ala Thr Asp Ser Arg Ala His Gly Ala Gly Gly
 50                  55                  60 ggc ggt ccg ggt cgt gct ggt tgc tgt ctg ggt aaa gct gtg cgc ggc        240
Gly Gly Pro Gly Arg Ala Gly Cys Cys Leu Gly Lys Ala Val Arg Gly
 65                  70                  75                  80 gcg aaa ggt cat cac cat ccg cac ccg gca gca ggt gca ggt gca            288
Ala Lys Gly His His His Pro His Pro Ala Ala Gly Ala Gly Ala
                 85                  90                  95 gct ggc ggt gcg gaa gcc gat ctg aaa gcc ctg acc cat agt gtc ctg        336
Ala Gly Gly Ala Glu Ala Asp Leu Lys Ala Leu Thr His Ser Val Leu
                100                 105                 110 aaa aaa ctg aaa gaa cgt cag ctg gag ctg ctg ctg caa gca gta gaa        384
Lys Lys Leu Lys Glu Arg Gln Leu Glu Leu Leu Leu Gln Ala Val Glu
            115                 120                 125 tcc cgt ggc ggt acc cgt acg gct tgt ctg ctg ctg ccg ggt cgt ctg        432
Ser Arg Gly Gly Thr Arg Thr Ala Cys Leu Leu Leu Pro Gly Arg Leu
        130                 135                 140 gat tgc cgt ctg ggt ccg ggt gca ccg gct ggt gcg cag ccg gca caa        480
Asp Cys Arg Leu Gly Pro Gly Ala Pro Ala Gly Ala Gln Pro Ala Gln
145                 150                 155                 160 ccg ccg agc tct tac agc ctg ccg ctg ctg ctg tgt aaa gtg ttt cgt        528
Pro Pro Ser Ser Tyr Ser Leu Pro Leu Leu Leu Cys Lys Val Phe Arg
                165                 170                 175 tgg ccg gac ctg cgc cac agt tcc gaa gtt aaa cgc ctg tgc tgt tgc        576
Trp Pro Asp Leu Arg His Ser Ser Glu Val Lys Arg Leu Cys Cys Cys
            180                 185                 190 gag agc tat ggc aaa att aac ccg gaa ctg gtt tgt tgc aat ccg cac        624
Glu Ser Tyr Gly Lys Ile Asn Pro Glu Leu Val Cys Cys Asn Pro His
        195                 200                 205 cat ctg tct cgt ctg tgt gaa ctg gag agc ccg ccg ccg tat tct            672
His Leu Ser Arg Leu Cys Glu Leu Glu Ser Pro Pro Pro Pro Tyr Ser
    210                 215                 220 cgt tac ccg atg gat ttc ctg aaa ccg act gca gat tgc ccg gac gca        720
Arg Tyr Pro Met Asp Phe Leu Lys Pro Thr Ala Asp Cys Pro Asp Ala
225                 230                 235                 240 gtc ccg tca tcg gct gag acc ggc ggc acc aac tat ctg gca ccg ggc        768
Val Pro Ser Ser Ala Glu Thr Gly Gly Thr Asn Tyr Leu Ala Pro Gly
                245                 250                 255 ggt ctg agt gat tcc cag ctg ctg ctg gaa ccg ggc gac cgt ggt aag        816
Gly Leu Ser Asp Ser Gln Leu Leu Leu Glu Pro Gly Asp Arg Gly Lys
            260                 265                 270 cct atc cct aac cct ctc ctc ggt ctc gat tct acg tgagtcgac              861
Pro Ile Pro Asn Pro Leu Leu Gly Leu Asp Ser Thr
        275                 280

<210> SEQ ID NO 27
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ser Gly Arg Lys Lys Arg Arg Gln Arg Arg Gly Phe Arg Thr
1               5                   10                  15

Lys Arg Ser Ala Leu Val Arg Arg Leu Trp Arg Ser Arg Ala Pro Gly
```

```
                 20                  25                  30
Gly Glu Asp Glu Glu Gly Ala Gly Gly Gly Gly Gly Gly Glu
             35                  40                  45
Leu Arg Gly Glu Gly Ala Thr Asp Ser Arg Ala His Gly Ala Gly Gly
         50                  55                  60
Gly Gly Pro Gly Arg Ala Gly Cys Cys Leu Gly Lys Ala Val Arg Gly
 65                  70                  75                  80
Ala Lys Gly His His His Pro His Pro Pro Ala Gly Ala Gly Ala
                 85                  90                  95
Ala Gly Gly Ala Glu Ala Asp Leu Lys Ala Leu Thr His Ser Val Leu
            100                 105                 110
Lys Lys Leu Lys Glu Arg Gln Leu Glu Leu Leu Gln Ala Val Glu
            115                 120                 125
Ser Arg Gly Gly Thr Arg Thr Ala Cys Leu Leu Leu Pro Gly Arg Leu
            130                 135                 140
Asp Cys Arg Leu Gly Pro Gly Ala Pro Ala Gly Ala Gln Pro Ala Gln
145                 150                 155                 160
Pro Pro Ser Ser Tyr Ser Leu Pro Leu Leu Leu Cys Lys Val Phe Arg
                165                 170                 175
Trp Pro Asp Leu Arg His Ser Ser Glu Val Lys Arg Leu Cys Cys Cys
                180                 185                 190
Glu Ser Tyr Gly Lys Ile Asn Pro Glu Leu Val Cys Cys Asn Pro His
            195                 200                 205
His Leu Ser Arg Leu Cys Glu Leu Glu Ser Pro Pro Pro Pro Tyr Ser
            210                 215                 220
Arg Tyr Pro Met Asp Phe Leu Lys Pro Thr Ala Asp Cys Pro Asp Ala
225                 230                 235                 240
Val Pro Ser Ser Ala Glu Thr Gly Gly Thr Asn Tyr Leu Ala Pro Gly
                245                 250                 255
Gly Leu Ser Asp Ser Gln Leu Leu Leu Glu Pro Gly Asp Arg Gly Lys
            260                 265                 270
Pro Ile Pro Asn Pro Leu Leu Gly Leu Asp Ser Thr
            275                 280

<210> SEQ ID NO 28
<211> LENGTH: 1442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ggatccggcc gtaaaaaacg ccgtcaacgc cgccgtggtt tccgtacgaa acgctcggcc      60
ctggtccgtc gcctgtggcg ctcccgtgct ccgggtggtg aagatgaaga agaaggtgct    120
ggcggcggtg gcggtggcgg tgaactgcgt aagatgaaga agaaggtgct ggcggcggtg    180
gcggtggcgg tgaactgcgt ggcgagggtg caaccgatag tcgtgcacac ggtgcaggcg    240
gtggcggtcc gggtcgtgct ggttgctgtc tgggtaaagc tgtgcgcggc gcgaaaggtc    300
atcaccatcc gcaccgccg gcagcaggtg caggtgcagc tggcggtgcg gaagccgatc    360
tgaaagccct gacccatagt gtcctgaaaa aactgaaaga acgtcagctg gagctgctgc    420
tgcaagcagt agaatcccgt ggcggtaccc gtacggcttg tctgctgctg ccgggtcgtc    480
tggattgccg tctgggtccg ggtgcaccgg ctggtgcgca gccggcacaa ccgccgagct    540
```

```
cttacagcct gccgctgctg ctgtgtaaag tgtttcgttg gccggacctg cgccacagtt      600
ccgaagttaa acgcctgtgc tgttgcgaga gctatggcaa aattaacccg gaactggttt      660
gttgcaatcc gcaccatctg tctcgtctgt gtgaactgga gagcccgccg ccgccgtatt      720
ctcgttaccc gatggatttc ctgaaaccga ctgcagattg cccggacgca gtcccgtcat      780
cggctgagac cggcggcacc aactatctgg caccgggcgg tctgagtgat cccagctgc       840 tgctggaacc gggcgaccgt tcacattggt gtgtggttgc ctattgggaa gagaaaacgc      900
gtgtcggtcg cctgtactgc gtacaggaac cgtcgctgga tatcttttat gacctgccgc      960
agggcaatgg tttctgtctg ggccaactga actcagataa taaatcgcag ctggtgcaaa     1020
aagttcgctc aaaaattggc tgcggtatcc agctgacccg tgaagttgac ggtgtctggg     1080
tatataaccg cagctcttac ccgatttttta tcaaaagtgc caccctggat aatccggact     1140
cccgtacgct gctggtccac aaagtatttc cgggcttctc aatcaaagcg ttcgattacg     1200
agaaagccta ctcgctgcag cgcccgaacg accatgaatt catgcagcaa ccgtggacgg     1260
gttttactgt gcagatctct ttcgttaaag ctggggtca atgctacacc cgtcagttta     1320
tctcgtcctg tccgtgctgg ctggaagtga ttttcaatag ccgcaagggc gagctcaatt     1380
cgaagcttga aggtaagcct atccctaacc ctctcctcgg tctcgattct acgtgagtcg     1440
ac                                                                    1442
```

```
<210> SEQ ID NO 29
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agcagctttc agtcagtagc agccagcagc cagagcagca gccagtagca gcagcagcag      60
agcagc                                                                66

<210> SEQ ID NO 30
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1383)

<400> SEQUENCE: 30
```

```
gga tcc ggc cgt aaa aaa cgc cgt caa cgc cgc cgt ggt ttc cgt acg        48
Gly Ser Gly Arg Lys Lys Arg Arg Gln Arg Arg Arg Gly Phe Arg Thr
1               5                   10                  15 aaa cgc agc gcc ctg gtc cgt cgc ctg tgg cgc agc cgt gct ccg ggt        96
Lys Arg Ser Ala Leu Val Arg Arg Leu Trp Arg Ser Arg Ala Pro Gly
            20                  25                  30 ggt gaa gat gaa gaa gaa ggt gct ggc ggc ggt ggc ggt ggc ggt gaa       144
Gly Glu Asp Glu Glu Glu Gly Ala Gly Gly Gly Gly Gly Gly Gly Glu
        35                  40                  45 ctg cgt ggc gag ggt gca acc gat agc cgt gca cat ggt gca ggc ggt       192
Leu Arg Gly Glu Gly Ala Thr Asp Ser Arg Ala His Gly Ala Gly Gly
    50                  55                  60 ggc ggt ccg ggt cgt gct ggt tgc tgt ctg ggt aaa gct gtg cgc ggc       240
Gly Gly Pro Gly Arg Ala Gly Cys Cys Leu Gly Lys Ala Val Arg Gly
```

-continued

| | | | | | | | | | | | | | | | |
|---|---|---|---|---|---|---|---|---|---|---|---|---|---|---|---|
| 65 | | | | | 70 | | | | | 75 | | | | | 80 |

```
gcg aaa ggt cat cat cat ccg cat ccg ccg gca gca ggt gca ggt gca      288
Ala Lys Gly His His His Pro His Pro Pro Ala Ala Gly Ala Gly Ala
                     85              90              95 gct ggc ggt gcg gaa gcc gat ctg aaa gcc ctg acc cat agc gtc ctg      336
Ala Gly Gly Ala Glu Ala Asp Leu Lys Ala Leu Thr His Ser Val Leu
            100             105             110 aaa aaa ctg aaa gaa cgt cag ctg gag ctg ctg caa gca gta gaa          384
Lys Lys Leu Lys Glu Arg Gln Leu Glu Leu Leu Gln Ala Val Glu
        115             120             125 agc cgt ggc ggt acc cgt acg gct tgt ctg ctg ctg ccg ggt cgt ctg      432
Ser Arg Gly Gly Thr Arg Thr Ala Cys Leu Leu Leu Pro Gly Arg Leu
        130             135             140 gat tgc cgt ctg ggt ccg ggt gca ccg gct ggt gcg cag ccg gca caa      480
Asp Cys Arg Leu Gly Pro Gly Ala Pro Ala Gly Ala Gln Pro Ala Gln
145             150             155             160 ccg ccg agc agc tac agc ctg ccg ctg ctg ctg tgt aaa gtg ttt cgt      528
Pro Pro Ser Ser Tyr Ser Leu Pro Leu Leu Leu Cys Lys Val Phe Arg
                165             170             175 tgg ccg gac ctg cgc cat agc agc gaa gtt aaa cgc ctg tgc tgt tgc      576
Trp Pro Asp Leu Arg His Ser Ser Glu Val Lys Arg Leu Cys Cys Cys
            180             185             190 gag agc tat ggc aaa att aac ccg gaa ctg gtt tgt tgc aat ccg cat      624
Glu Ser Tyr Gly Lys Ile Asn Pro Glu Leu Val Cys Cys Asn Pro His
        195             200             205 cat ctg agc cgt ctg tgt gaa ctg gag agc ccg ccg ccg tat agc          672
His Leu Ser Arg Leu Cys Glu Leu Glu Ser Pro Pro Pro Tyr Ser
        210             215             220 cgt tac ccg ctg gat ttc ctg aaa ccg act gca gat tgc ccg gac gca      720
Arg Tyr Pro Leu Asp Phe Leu Lys Pro Thr Ala Asp Cys Pro Asp Ala
225             230             235             240 gtc ccg agc agc gct gag acc ggc ggc acc aac tat ctg gca ccg ggc      768
Val Pro Ser Ser Ala Glu Thr Gly Gly Thr Asn Tyr Leu Ala Pro Gly
                245             250             255 ggt ctg agc gat agc cag ctg ctg ctg gaa ccg ggc gac cgt agc cat      816
Gly Leu Ser Asp Ser Gln Leu Leu Leu Glu Pro Gly Asp Arg Ser His
            260             265             270 tgg tgt gtg gtt gcc tat tgg gaa gag aaa acg cgt gtc ggt cgc ctg      864
Trp Cys Val Val Ala Tyr Trp Glu Glu Lys Thr Arg Val Gly Arg Leu
        275             280             285 tac tgc gta cag gaa ccg agc ctg gat atc ttt tat gac ctg ccg cag      912
Tyr Cys Val Gln Glu Pro Ser Leu Asp Ile Phe Tyr Asp Leu Pro Gln
        290             295             300 ggc aat ggt ttc tgt ctg ggc caa ctg aac agc gat aat aaa agc cag      960
Gly Asn Gly Phe Cys Leu Gly Gln Leu Asn Ser Asp Asn Lys Ser Gln
305             310             315             320 ctg gtg caa aaa gtt cgc agc aaa att ggc tgc ggt atc cag ctg acc     1008
Leu Val Gln Lys Val Arg Ser Lys Ile Gly Cys Gly Ile Gln Leu Thr
                325             330             335 cgt gaa gtt gac ggt gtc tgg gta tat aac cgc agc agc tac ccg att     1056
Arg Glu Val Asp Gly Val Trp Val Tyr Asn Arg Ser Ser Tyr Pro Ile
            340             345             350 ttt atc aaa agc gcc acc ctg gat aat ccg gac agc cgt acg ctg ctg     1104
Phe Ile Lys Ser Ala Thr Leu Asp Asn Pro Asp Ser Arg Thr Leu Leu
        355             360             365 gtc cat aaa gta ttt ccg ggc ttc agc atc aaa gcg ttc gat tac gag     1152
Val His Lys Val Phe Pro Gly Phe Ser Ile Lys Ala Phe Asp Tyr Glu
        370             375             380 aaa gcc tac agc ctg cag cgc ccg aac gac cat gaa ttc atg cag caa     1200
Lys Ala Tyr Ser Leu Gln Arg Pro Asn Asp His Glu Phe Met Gln Gln
```

```
Lys Ala Tyr Ser Leu Gln Arg Pro Asn Asp His Glu Phe Met Gln Gln
385                 390                 395                 400 ccg tgg acg ggt ttt act gtg cag atc agc ttc gtt aaa ggc tgg ggt     1248
Pro Trp Thr Gly Phe Thr Val Gln Ile Ser Phe Val Lys Gly Trp Gly
                405                 410                 415 caa tgc tac acc cgt cag ttt atc agc agc tgt ccg tgc tgg ctg gaa     1296
Gln Cys Tyr Thr Arg Gln Phe Ile Ser Ser Cys Pro Cys Trp Leu Glu
                420                 425                 430 gtg att ttc aat agc cgc aag ggc gag ctc aat agc aag ctt gaa ggt     1344
Val Ile Phe Asn Ser Arg Lys Gly Glu Leu Asn Ser Lys Leu Glu Gly
                435                 440                 445 aag cct atc cct aac cct ctc ctc ggt ctc gat agc acg tgagtcgac       1392
Lys Pro Ile Pro Asn Pro Leu Leu Gly Leu Asp Ser Thr
450                 455                 460

<210> SEQ ID NO 31
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Ser Gly Arg Lys Lys Arg Arg Gln Arg Arg Gly Phe Arg Thr
1               5                   10                  15

Lys Arg Ser Ala Leu Val Arg Arg Leu Trp Arg Ser Arg Ala Pro Gly
                20                  25                  30

Gly Glu Asp Glu Glu Glu Gly Ala Gly Gly Gly Gly Gly Gly Gly Glu
            35                  40                  45

Leu Arg Gly Glu Gly Ala Thr Asp Ser Arg Ala His Gly Ala Gly Gly
50                  55                  60

Gly Gly Pro Gly Arg Ala Gly Cys Cys Leu Gly Lys Ala Val Arg Gly
65                  70                  75                  80

Ala Lys Gly His His His Pro His Pro Pro Ala Ala Gly Ala Gly Ala
                85                  90                  95

Ala Gly Gly Ala Glu Ala Asp Leu Lys Ala Leu Thr His Ser Val Leu
            100                 105                 110

Lys Lys Leu Lys Glu Arg Gln Leu Glu Leu Leu Leu Gln Ala Val Glu
        115                 120                 125

Ser Arg Gly Gly Thr Arg Thr Ala Cys Leu Leu Leu Pro Gly Arg Leu
    130                 135                 140

Asp Cys Arg Leu Gly Pro Gly Ala Pro Ala Gly Ala Gln Pro Ala Gln
145                 150                 155                 160

Pro Pro Ser Ser Tyr Ser Leu Pro Leu Leu Leu Cys Lys Val Phe Arg
                165                 170                 175

Trp Pro Asp Leu Arg His Ser Ser Glu Val Lys Arg Leu Cys Cys Cys
            180                 185                 190

Glu Ser Tyr Gly Lys Ile Asn Pro Glu Leu Val Cys Cys Asn Pro His
        195                 200                 205

His Leu Ser Arg Leu Cys Glu Leu Glu Ser Pro Pro Pro Pro Tyr Ser
    210                 215                 220

Arg Tyr Pro Leu Asp Phe Leu Lys Pro Thr Ala Asp Cys Pro Asp Ala
225                 230                 235                 240

Val Pro Ser Ser Ala Glu Thr Gly Gly Thr Asn Tyr Leu Ala Pro Gly
                245                 250                 255

Gly Leu Ser Asp Ser Gln Leu Leu Leu Glu Pro Gly Asp Arg Ser His
```

```
                260                 265                 270
Trp Cys Val Ala Tyr Trp Glu Glu Lys Thr Arg Val Gly Arg Leu
        275                 280                 285
Tyr Cys Val Gln Glu Pro Ser Leu Asp Ile Phe Tyr Asp Leu Pro Gln
290                 295                 300
Gly Asn Gly Phe Cys Leu Gly Gln Leu Asn Ser Asp Asn Lys Ser Gln
305                 310                 315                 320
Leu Val Gln Lys Val Arg Ser Lys Ile Gly Cys Gly Ile Gln Leu Thr
                325                 330                 335
Arg Glu Val Asp Gly Val Trp Val Tyr Asn Arg Ser Ser Tyr Pro Ile
            340                 345                 350
Phe Ile Lys Ser Ala Thr Leu Asp Asn Pro Asp Ser Arg Thr Leu Leu
        355                 360                 365
Val His Lys Val Phe Pro Gly Phe Ser Ile Lys Ala Phe Asp Tyr Glu
    370                 375                 380
Lys Ala Tyr Ser Leu Gln Arg Pro Asn Asp His Glu Phe Met Gln Gln
385                 390                 395                 400
Pro Trp Thr Gly Phe Thr Val Gln Ile Ser Phe Val Lys Gly Trp Gly
                405                 410                 415
Gln Cys Tyr Thr Arg Gln Phe Ile Ser Ser Cys Pro Cys Trp Leu Glu
            420                 425                 430
Val Ile Phe Asn Ser Arg Lys Gly Glu Leu Asn Ser Lys Leu Glu Gly
        435                 440                 445
Lys Pro Ile Pro Asn Pro Leu Leu Gly Leu Asp Ser Thr
    450                 455                 460

<210> SEQ ID NO 32
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(852)

<400> SEQUENCE: 32 gga tcc ggc cgt aaa aaa cgc cgt caa cgc cgc cgt ggt ttc cgt acg      48
Gly Ser Gly Arg Lys Lys Arg Arg Gln Arg Arg Arg Gly Phe Arg Thr
1               5                   10                  15 aaa cgc agc gcc ctg gtc cgt cgc ctg tgg cgc agc cgt gct ccg ggt      96
Lys Arg Ser Ala Leu Val Arg Arg Leu Trp Arg Ser Arg Ala Pro Gly
            20                  25                  30 ggt gaa gat gaa gaa gaa ggt gct ggc ggc ggt ggc ggt ggc ggt gaa     144
Gly Glu Asp Glu Glu Glu Gly Ala Gly Gly Gly Gly Gly Gly Gly Glu
        35                  40                  45 ctg cgt ggc gag ggt gca acc gat agc cgt gca cat ggt gca ggc ggt     192
Leu Arg Gly Glu Gly Ala Thr Asp Ser Arg Ala His Gly Ala Gly Gly
    50                  55                  60 ggc ggt ccg ggt cgt gct ggt tgc tgt ctg ggt aaa gct gtg cgc ggc     240
Gly Gly Pro Gly Arg Ala Gly Cys Cys Leu Gly Lys Ala Val Arg Gly
65                  70                  75                  80 gcg aaa ggt cat cat cat ccg cat ccg ccg gca gca ggt gca ggt gca     288
Ala Lys Gly His His His Pro His Pro Pro Ala Ala Gly Ala Gly Ala
                85                  90                  95 gct ggc ggt gcg gaa gcc gat ctg aaa gcc ctg acc cat agc gtc ctg     336
Ala Gly Gly Ala Glu Ala Asp Leu Lys Ala Leu Thr His Ser Val Leu
            100                 105                 110
```

```
aaa aaa ctg aaa gaa cgt cag ctg gag ctg ctg caa gca gta gaa        384
Lys Lys Leu Lys Glu Arg Gln Leu Glu Leu Leu Gln Ala Val Glu
            115                 120                 125 agc cgt ggc ggt acc cgt acg gct tgt ctg ctg ccg ggt cgt ctg        432
Ser Arg Gly Gly Thr Arg Thr Ala Cys Leu Leu Pro Gly Arg Leu
    130                 135                 140 gat tgc cgt ctg ggt ccg ggt gca ccg gct ggt gcg cag ccg gca caa    480
Asp Cys Arg Leu Gly Pro Gly Ala Pro Ala Gly Ala Gln Pro Ala Gln
145                 150                 155                 160 ccg ccg agc agc tac agc ctg ccg ctg ctg tgt aaa gtg ttt cgt        528
Pro Pro Ser Ser Tyr Ser Leu Pro Leu Leu Cys Lys Val Phe Arg
                165                 170                 175 tgg ccg gac ctg cgc cat agc agc gaa gtt aaa cgc ctg tgc tgt tgc    576
Trp Pro Asp Leu Arg His Ser Ser Glu Val Lys Arg Leu Cys Cys Cys
                180                 185                 190 gag agc tat ggc aaa att aac ccg gaa ctg gtt tgt tgc aat ccg cat    624
Glu Ser Tyr Gly Lys Ile Asn Pro Glu Leu Val Cys Cys Asn Pro His
            195                 200                 205 cat ctg agc cgt ctg tgt gaa ctg gag agc ccg ccg ccg tat agc        672
His Leu Ser Arg Leu Cys Glu Leu Glu Ser Pro Pro Pro Tyr Ser
    210                 215                 220 cgt tac ccg atg gat ttc ctg aaa ccg act gca gat tgc ccg gac gca    720
Arg Tyr Pro Met Asp Phe Leu Lys Pro Thr Ala Asp Cys Pro Asp Ala
225                 230                 235                 240 gtc ccg agc agc gct gag acc ggc ggc acc aac tat ctg gca ccg ggc    768
Val Pro Ser Ser Ala Glu Thr Gly Gly Thr Asn Tyr Leu Ala Pro Gly
                245                 250                 255 ggt ctg agc gat agc cag ctg ctg ctg gaa ccg ggc gac cgt ggt aag    816
Gly Leu Ser Asp Ser Gln Leu Leu Leu Glu Pro Gly Asp Arg Gly Lys
            260                 265                 270 cct atc cct aac cct ctc ctc ggt ctc gat tct acg tgagtcgac          861
Pro Ile Pro Asn Pro Leu Leu Gly Leu Asp Ser Thr
            275                 280
```

<210> SEQ ID NO 33
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
ggatccggcc gtaaaaaacg ccgtcaacgc cgccgttcac attggtgtgt ggttgcctat    60
tgggaagaga aaacgcgtgt cggtcgcctg tactgcgtac aggaaccgag cctggatatc   120
ttttatgacc tgccgcaggg caatggtttc tgtctgggcc aactgaacag cgataataaa   180
agccagctgg tgcaaaaagt tcgcagcaaa attggctgcg gtatccagct gacccgtgaa   240
gttgacggtg tctgggtata taccgcagc agctacccga ttttatcaa agcgccacc     300 ctggataatc cggacagccg tacgctgctg gtccataaag tatttccggg cttcagcatc   360
aaagcgttcg attacgagaa agcctacagc ctgcagcgcc gaacgacca tgaattcatg   420 cagcaaccgt ggacgggttt tactgtgcag atcagcttcg ttaaaggctg ggtcaatgc    480 aagggcgagc tcaatagcaa gcttgaaggt aagcctatcc taaccctct cctcggtctc   540 gatagcacgt gagtcgac                                                 558
```

<210> SEQ ID NO 34
<211> LENGTH: 618

```
-continued

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(609)

<400> SEQUENCE: 34 gga tcc ggc cgt aaa aaa cgc cgt caa cgc cgc cgt tca cat tgg tgt       48
Gly Ser Gly Arg Lys Lys Arg Arg Gln Arg Arg Arg Ser His Trp Cys
1               5                   10                  15 gtg gtt gcc tat tgg gaa gag aaa acg cgt gtc ggt cgc ctg tac tgc       96
Val Val Ala Tyr Trp Glu Glu Lys Thr Arg Val Gly Arg Leu Tyr Cys
            20                  25                  30 gta cag gaa ccg agc ctg gat atc ttt tat gac ctg ccg cag ggc aat      144
Val Gln Glu Pro Ser Leu Asp Ile Phe Tyr Asp Leu Pro Gln Gly Asn
        35                  40                  45 ggt ttc tgt ctg ggc caa ctg aac agc gat aat aaa agc cag ctg gtg      192
Gly Phe Cys Leu Gly Gln Leu Asn Ser Asp Asn Lys Ser Gln Leu Val
    50                  55                  60 caa aaa gtt cgc agc aaa att ggc tgc ggt atc cag ctg acc cgt gaa      240
Gln Lys Val Arg Ser Lys Ile Gly Cys Gly Ile Gln Leu Thr Arg Glu
65                  70                  75                  80 gtt gac ggt gtc tgg gta tat aac cgc agc agc tac ccg att ttt atc      288
Val Asp Gly Val Trp Val Tyr Asn Arg Ser Ser Tyr Pro Ile Phe Ile
                85                  90                  95 aaa agc gcc acc ctg gat aat ccg gac agc cgt acg ctg ctg gtc cat      336
Lys Ser Ala Thr Leu Asp Asn Pro Asp Ser Arg Thr Leu Leu Val His
            100                 105                 110 aaa gta ttt ccg ggc ttc agc atc aaa gcg ttc gat tac gag aaa gcc      384
Lys Val Phe Pro Gly Phe Ser Ile Lys Ala Phe Asp Tyr Glu Lys Ala
        115                 120                 125 tac agc ctg cag cgc ccg aac gac cat gaa ttc atg cag caa ccg tgg      432
Tyr Ser Leu Gln Arg Pro Asn Asp His Glu Phe Met Gln Gln Pro Trp
    130                 135                 140 acg ggt ttt act gtg cag atc agc ttc gtt aaa ggc tgg ggt caa tgc      480
Thr Gly Phe Thr Val Gln Ile Ser Phe Val Lys Gly Trp Gly Gln Cys
145                 150                 155                 160 tac acc cgt cag ttt atc agc agc tgt ccg tgc tgg ctg gaa gtg att      528
Tyr Thr Arg Gln Phe Ile Ser Ser Cys Pro Cys Trp Leu Glu Val Ile
                165                 170                 175 ttc aat agc cgc aag ggc gag ctc aat agc aag ctt gaa ggt aag cct      576
Phe Asn Ser Arg Lys Gly Glu Leu Asn Ser Lys Leu Glu Gly Lys Pro
            180                 185                 190 atc cct aac cct ctc ctc ggt ctc gat agc acg tgagtcgac                618
Ile Pro Asn Pro Leu Leu Gly Leu Asp Ser Thr
        195                 200

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcgtcatcgt catctttcct catcgtcttc gtctcgtct                            39

<210> SEQ ID NO 36
<211> LENGTH: 1365
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1356)

<400> SEQUENCE: 36 gga tcc ggt cgt aaa aaa cgt cgt cag cgt cgt cgt ggt ttc cgt acc      48
Gly Ser Gly Arg Lys Lys Arg Arg Gln Arg Arg Arg Gly Phe Arg Thr
1               5                   10                  15 aaa cgt tct gcg ctg gtt cgt cgt ctg tgg cgt tct cgt gcg ccg ggt      96
Lys Arg Ser Ala Leu Val Arg Arg Leu Trp Arg Ser Arg Ala Pro Gly
            20                  25                  30 ggt gaa gac gaa gaa gaa ggt gcg ggt ggt ggt ggt ggt ggt gaa         144
Gly Glu Asp Glu Glu Glu Gly Ala Gly Gly Gly Gly Gly Gly Glu
        35                  40                  45 ctg cgt ggt gaa ggt gcg acc gac tct cgt gcg cac ggt gcg ggt ggt    192
Leu Arg Gly Glu Gly Ala Thr Asp Ser Arg Ala His Gly Ala Gly Gly
50                  55                  60 ggt ggt ccg ggt cgt gcg ggt tgc tgc ctg ggt aaa gcg gtt cgt ggt    240
Gly Gly Pro Gly Arg Ala Gly Cys Cys Leu Gly Lys Ala Val Arg Gly
65                  70                  75                  80 gcg aaa ggt cac cac cac ccg cac ccg ccg gcg gcg ggt gcg ggt gcg    288
Ala Lys Gly His His His Pro His Pro Pro Ala Ala Gly Ala Gly Ala
                85                  90                  95 gcg ggt ggt gcg gaa gcg gac ctg aaa gcg ctg acc cac tct gtt ctg    336
Ala Gly Gly Ala Glu Ala Asp Leu Lys Ala Leu Thr His Ser Val Leu
            100                 105                 110 aaa aaa ctg aaa gaa cgt cag ctg gaa ctg ctg ctg cag gcg gtt gaa    384
Lys Lys Leu Lys Glu Arg Gln Leu Glu Leu Leu Leu Gln Ala Val Glu
        115                 120                 125 tct cgt ggt ggt acc cgt acc gcg tgc ctg ctg ctg ccg ggt cgt ctg    432
Ser Arg Gly Gly Thr Arg Thr Ala Cys Leu Leu Leu Pro Gly Arg Leu
130                 135                 140 gac tgc cgt ctg ggt ccg ggt gcg ccg gcg ggt gcg cag ccg gcg cag    480
Asp Cys Arg Leu Gly Pro Gly Ala Pro Ala Gly Ala Gln Pro Ala Gln
145                 150                 155                 160 ccg ccg tct tct tac tct ctg ccg ctg ctg ctg tgc aaa gtt ttc cgt    528
Pro Pro Ser Ser Tyr Ser Leu Pro Leu Leu Leu Cys Lys Val Phe Arg
                165                 170                 175 tgg ccg gac ctg cgt cac tct tct gaa gtt aaa cgt ctg tgc tgc tgc    576
Trp Pro Asp Leu Arg His Ser Ser Glu Val Lys Arg Leu Cys Cys Cys
            180                 185                 190 gaa tct tac ggt aaa atc aac ccg gaa ctg gtt tgc tgc aac ccg cac    624
Glu Ser Tyr Gly Lys Ile Asn Pro Glu Leu Val Cys Cys Asn Pro His
        195                 200                 205 cac ctg tct cgt ctg tgc gaa ctg gaa tct ccg ccg ccg tac tct        672
His Leu Ser Arg Leu Cys Glu Leu Glu Ser Pro Pro Pro Tyr Ser
210                 215                 220 cgt tac ccg ctg gac ttc ctg aaa ccg acc gcg gac tgc ccg gac gcg    720
Arg Tyr Pro Leu Asp Phe Leu Lys Pro Thr Ala Asp Cys Pro Asp Ala
225                 230                 235                 240 gtt ccg tct tct gcg gaa acc ggt ggt acc aac tac ctg gcg ccg ggt    768
Val Pro Ser Ser Ala Glu Thr Gly Gly Thr Asn Tyr Leu Ala Pro Gly
                245                 250                 255 ggt ctg tct gac tct cag ctg ctg ctg gaa ccg ggt gac cgt tct cac    816
Gly Leu Ser Asp Ser Gln Leu Leu Leu Glu Pro Gly Asp Arg Ser His
            260                 265                 270
```

```
tgg tgc gtt gtt gcg tac tgg gaa gaa aaa acc cgt gtt ggt cgt ctg      864
Trp Cys Val Val Ala Tyr Trp Glu Glu Lys Thr Arg Val Gly Arg Leu
        275                 280                 285 tac tgc gtt cag gaa ccg tct ctg gac atc ttc tac gac ctg ccg cag      912
Tyr Cys Val Gln Glu Pro Ser Leu Asp Ile Phe Tyr Asp Leu Pro Gln
        290                 295                 300 ggt aac ggt ttc tgc ctg ggt cag ctg aac tct gac aac aaa tct cag      960
Gly Asn Gly Phe Cys Leu Gly Gln Leu Asn Ser Asp Asn Lys Ser Gln
305                 310                 315                 320 ctg gtt cag aaa gtt cgt tct aaa atc ggt tgc ggt atc cag ctg acc     1008
Leu Val Gln Lys Val Arg Ser Lys Ile Gly Cys Gly Ile Gln Leu Thr
                325                 330                 335 cgt gaa gtt gac ggt gtt tgg gtt tac aac cgt tct tct tac ccg atc     1056
Arg Glu Val Asp Gly Val Trp Val Tyr Asn Arg Ser Ser Tyr Pro Ile
            340                 345                 350 ttc atc aaa tct gcg acc ctg gac aac ccg gac tct cgt acc ctg ctg     1104
Phe Ile Lys Ser Ala Thr Leu Asp Asn Pro Asp Ser Arg Thr Leu Leu
        355                 360                 365 gtt cac aaa gtt ttc ccg ggt ttc tct atc aaa gcg ttc gac tac gaa     1152
Val His Lys Val Phe Pro Gly Phe Ser Ile Lys Ala Phe Asp Tyr Glu
    370                 375                 380 aaa gcg tac tct ctg cag cgt ccg aac gac cac gaa ttc atg cag cag     1200
Lys Ala Tyr Ser Leu Gln Arg Pro Asn Asp His Glu Phe Met Gln Gln
385                 390                 395                 400 ccg tgg acc ggt ttc acc gtt cag atc tct ttc gtt aaa ggt tgg ggt     1248
Pro Trp Thr Gly Phe Thr Val Gln Ile Ser Phe Val Lys Gly Trp Gly
                405                 410                 415 cag tgc tac acc cgt cag ttc atc tct tct tgc ccg tgc tgg ctg gaa     1296
Gln Cys Tyr Thr Arg Gln Phe Ile Ser Ser Cys Pro Cys Trp Leu Glu
            420                 425                 430 gtt atc ttc aac tct cgt ggt aaa ccg atc ccg aac ccg ctg ctg ggt     1344
Val Ile Phe Asn Ser Arg Gly Lys Pro Ile Pro Asn Pro Leu Leu Gly
        435                 440                 445 ctg gac tct acc tgagtcgac                                           1365
Leu Asp Ser Thr
    450

<210> SEQ ID NO 37
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ser Gly Arg Lys Lys Arg Gln Arg Arg Gly Phe Arg Thr
1               5                   10                  15

Lys Arg Ser Ala Leu Val Arg Arg Leu Trp Arg Ser Arg Ala Pro Gly
                20                  25                  30

Gly Glu Asp Glu Glu Glu Gly Ala Gly Gly Gly Gly Gly Gly Gly Glu
            35                  40                  45

Leu Arg Gly Glu Gly Ala Thr Asp Ser Arg Ala His Gly Ala Gly Gly
        50                  55                  60

Gly Gly Pro Gly Arg Ala Gly Cys Cys Leu Gly Lys Ala Val Arg Gly
65                  70                  75                  80

Ala Lys Gly His His His Pro His Pro Pro Ala Ala Gly Ala Gly Ala
                85                  90                  95

Ala Gly Gly Ala Glu Ala Asp Leu Lys Ala Leu Thr His Ser Val Leu
            100                 105                 110
```

```
Lys Lys Leu Lys Glu Arg Gln Leu Glu Leu Leu Gln Ala Val Glu
        115                 120                 125

Ser Arg Gly Gly Thr Arg Thr Ala Cys Leu Leu Pro Gly Arg Leu
    130                 135                 140

Asp Cys Arg Leu Gly Pro Gly Ala Pro Ala Gly Ala Gln Pro Ala Gln
145                 150                 155                 160

Pro Pro Ser Ser Tyr Ser Leu Pro Leu Leu Cys Lys Val Phe Arg
            165                 170                 175

Trp Pro Asp Leu Arg His Ser Ser Glu Val Lys Arg Leu Cys Cys Cys
                180                 185                 190

Glu Ser Tyr Gly Lys Ile Asn Pro Glu Leu Val Cys Cys Asn Pro His
        195                 200                 205

His Leu Ser Arg Leu Cys Glu Leu Glu Ser Pro Pro Pro Pro Tyr Ser
    210                 215                 220

Arg Tyr Pro Leu Asp Phe Leu Lys Pro Thr Ala Asp Cys Pro Asp Ala
225                 230                 235                 240

Val Pro Ser Ser Ala Glu Thr Gly Gly Thr Asn Tyr Leu Ala Pro Gly
            245                 250                 255

Gly Leu Ser Asp Ser Gln Leu Leu Leu Glu Pro Gly Asp Arg Ser His
        260                 265                 270

Trp Cys Val Val Ala Tyr Trp Glu Glu Lys Thr Arg Val Gly Arg Leu
    275                 280                 285

Tyr Cys Val Gln Glu Pro Ser Leu Asp Ile Phe Tyr Asp Leu Pro Gln
    290                 295                 300

Gly Asn Gly Phe Cys Leu Gly Gln Leu Asn Ser Asp Asn Lys Ser Gln
305                 310                 315                 320

Leu Val Gln Lys Val Arg Ser Lys Ile Gly Cys Gly Ile Gln Leu Thr
                325                 330                 335

Arg Glu Val Asp Gly Val Trp Val Tyr Asn Arg Ser Ser Tyr Pro Ile
            340                 345                 350

Phe Ile Lys Ser Ala Thr Leu Asp Asn Pro Asp Ser Arg Thr Leu Leu
        355                 360                 365

Val His Lys Val Phe Pro Gly Phe Ser Ile Lys Ala Phe Asp Tyr Glu
    370                 375                 380

Lys Ala Tyr Ser Leu Gln Arg Pro Asn Asp His Glu Phe Met Gln Gln
385                 390                 395                 400

Pro Trp Thr Gly Phe Thr Val Gln Ile Ser Phe Val Lys Gly Trp Gly
                405                 410                 415

Gln Cys Tyr Thr Arg Gln Phe Ile Ser Ser Cys Pro Cys Trp Leu Glu
            420                 425                 430

Val Ile Phe Asn Ser Arg Gly Lys Pro Ile Pro Asn Pro Leu Leu Gly
        435                 440                 445

Leu Asp Ser Thr
    450

<210> SEQ ID NO 38
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ggatccggtc gtaaaaaacg tcgtcagcgt cgtcgtggtt tccgtaccaa acgttctgcg      60
```

```
ctggttcgtc gtctgtggcg ttctcgtgcg ccgggtggtg aagacgaaga agaaggtgcg      120
ggtggtggtg gtggtggtgg tgaactgcgt ggtgaaggtg cgaccgactc tcgtgcgcac      180
ggtgcgggtg gtggtggtcc gggtcgtgcg ggttgctgcc tgggtaaagc ggttcgtggt      240
gcgaaaggtc accaccaccc gcacccgccg gcggcgggtg cgggtgcggc gggtggtgcg      300
gaagcggacc tgaaagcgct gacccactct gttctgaaaa aactgaaaga acgtcagctg      360
gaactgctgc tgcaggcggt tgaatctcgt ggtggtaccc gtaccgcgtg cctgctgctg      420
ccgggtcgtc tggactgccg tctgggtccg ggtgcgccgg cgggtgcgca gccggcgcag      480
ccgccgtctt cttactctct gccgctgctg ctgtgcaaag ttttccgttg gccggacctg      540
cgtcactctt ctgaagttaa acgtctgtgc tgctgcgaat cttacggtaa aatcaacccg      600
gaactggttt gctgcaaccc gcaccacctg tctcgtctgt gcgaactgga atctccgccg      660
ccgccgtact ctcgttaccc gctggacttc ctgaaaccga ccgcggactg cccggacgcg      720
gttccgtctt ctgcggaaac cggtggtacc aactacctgg cgccgggtgg tctgtctgac      780
tctcagctgc tgctggaacc gggtgaccgt tctcactggt gcgttgttgc gtactgggaa      840
gaaaaaaccc gtgttggtcg tctgtactgc gttcaggaac cgtctctgga catcttctac      900
gacctgccgc agggtaacgg tttctgcctg gtcagctga actctgacaa caaatctcag      960
ctggttcaga aagttcgttc taaaatcggt tgcggtatcc agctgacccg tgaagttgac     1020
ggtgtttggg tttacaaccg ttcttcttac ccgatcttca tcaaatctgc gaccctggac     1080
aacccggact ctcgtaccct gctggttcac aaagttttcc cgggtttctc tatcaaagcg     1140
ttcgactacg aaaaagcgta ctctctgcag cgtccgaacg accacgaatt catgcagcag     1200
ccgtggaccg gtttcaccgt tcagatctct ttcgttaaag gttggggtca gtgctacacc     1260
cgtcagttca tctcttcttg cccgtgctgg ctggaagtta tcttcaactc tcgtggtaaa     1320
ccgatcccga accgctgctg ggtctggac tctacctgag tcgac                      1365
```

<210> SEQ ID NO 39
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
ggatccggcc gtaaaaaacg ccgtcaacgc cgccgtggtt tccgtacgaa acgcagcgcc       60
ctggtccgtc gcctgtggcg cagccgtgct ccgggtggtg aagatgaaga agaaggtgct      120
ggcggcggtg gcggtggcgg tgaactgcgt ggcgagggtg caaccgatag ccgtgcacat      180
ggtgcaggcg gtggcggtcc gggtcgtgct ggttgctgtc tgggtaaagc tgtgcgcggc      240
gcgaaaggtc atcatcatcc gcatccgccg gcagcaggtg caggtgcagc tggcggtgcg      300
gaagccgatc tgaaagccct gacccatagc gtcctgaaaa aactgaaaga acgtcagctg      360
gagctgctgc tgcaagcagt agaaagccgt ggcggtaccc gtacggcttg tctgctgctg      420
ccgggtcgtc tggattgccg tctgggtccg ggtgcaccgg ctggtgcgca gccggcacaa      480
ccgccgagca gctacagcct gccgctgctg ctgtgtaaag tgtttcgttg gccggacctg      540
cgccatagca gcgaagttaa acgtctgtgc tgttgcgaga gctatggcaa aattaacccg      600
gaactggttt gttgcaatcc gcatcatctg agccgtctgt gtgaactgga gagcccgccg      660
ccgccgtata gccgttaccc gctggatttc ctgaaaccga ctgcagattg cccggacgca      720
```

```
gtcccgagca gcgctgagac cggcggcacc aactatctgg caccgggcgg tctgagcgat    780
agccagctgc tgctggaacc gggcgaccgt agccattggt gtgtggttgc ctattgggaa    840
gagaaaacgc gtgtcggtcg cctgtactgc gtacaggaac cgagcctgga tatctttat    900 gacctgccgc agggcaatgg tttctgtctg ggccaactga acagcgataa taaaagccag    960
ctggtgcaaa aagttcgcag caaaattggc tgcggtatcc agctgacccg tgaagttgac   1020
ggtgtctggg tatataaccg cagcagctac ccgattttta tcaaaagcgc caccctggat   1080
aatccggaca gccgtacgct gctggtccat aaagtatttc cgggcttcag catcaaagcg   1140
ttcgattacg agaaagccta cagcctgcag cgcccgaacg accatgaatt catgcagcaa   1200
ccgtggacgg gttttactgt gcagatcagc ttcgttaaag gctgggtca atgctacacc    1260 cgtcagttta tcagcagctg tccgtgctgg ctggaagtga ttttcaatag ccgcaagggc   1320
gagctcaata gcaagcttga aggtaagcct atccctaacc ctctcctcgg tctcgatagc   1380
acgtgagtcg ac                                                       1392
```

```
<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
1               5

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Lys Pro Ile Pro Asn Pro Leu Leu Gly Leu Asp Ser Thr
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Tyr Lys Asp Asp Asp Asp Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Pro Tyr Asp Val Pro Asp Tyr Ala
1               5
```

```
<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Gln Ile Lys Ile Trp Phe Gln Asn Arg Arg Met Lys Trp Lys Lys
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Arg Met Lys Trp Lys Lys
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Arg Trp Arg Arg Trp Trp Arg Arg Trp Trp Arg Arg Trp Arg Arg
1               5                   10                  15

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Gly Gly Arg Leu Ser Tyr Ser Arg Arg Phe Ser Thr Ser Thr
1               5                   10                  15

Gly Arg

<210> SEQ ID NO 49
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Lys Lys Arg Arg Gln Arg Arg Arg
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Ala Arg Ala Ala Ala Arg Gln Ala Arg Ala
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Arg Arg Arg Arg Arg Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Lys Lys Lys Lys Lys Lys Lys
1               5

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Any amino acid

<400> SEQUENCE: 53

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 54
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 54

Leu Leu Ile Leu Leu Arg Arg Arg Ile Arg Lys Gln Ala Asn Ala His
1               5                   10                  15

Ser Lys

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Arg Arg His His Cys Arg Ser Lys Ala Lys Arg Ser Arg His His
1               5                   10                  15

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Arg Ala Arg Arg Asn Arg Arg Arg Val Arg
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Gln Leu Arg Ile Ala Gly Arg Arg Leu Arg Gly Arg Ser Arg
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Leu Ile Lys Gly Arg Thr Pro Ile Lys Phe Gly Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Ile Pro Asn Arg Arg Pro Arg Arg
```

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Leu Ala Leu Lys Leu Ala Leu Lys Ala Leu Lys Ala Ala Leu Lys
1               5                   10                  15

Leu Ala

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Leu Ala Lys Leu Ala Lys Lys Leu Ala Lys Leu Ala Lys
1               5                   10

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Lys Lys Leu Leu Lys Lys Leu Leu Lys Lys Leu Leu Lys Lys Leu
1               5                   10                  15

Leu Lys Lys Leu
            20

<210> SEQ ID NO 65
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 66
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 69
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 69

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Any amino acid

<400> SEQUENCE: 70

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Pro Pro Pro Pro Pro Pro Pro Pro Pro Pro Pro Pro Pro
1               5                   10

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Val Arg Leu Pro Pro Pro Val Arg Leu Pro Pro Pro Val Arg Leu Pro
1               5                   10                  15

Pro Pro

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Arg Pro Leu Pro Pro Pro Arg Pro Gly
1               5                   10

<210> SEQ ID NO 74
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ser Val Arg Arg Pro Arg Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Arg Ser Ser Arg Ala Gly Leu Gln Phe Pro Val Gly Arg Val His
1               5                   10                  15

Arg Leu Leu Arg Lys
            20

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 77
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 78
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
                20                  25

<210> SEQ ID NO 79
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Asn Leu Lys Ala Leu Ala Ala Leu Ala Lys Lys Ile Leu
1               5                   10

<210> SEQ ID NO 81
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
                20                  25                  30

Glu

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ala Lys Trp Ala Leu Lys Gln Gly Phe Ala Lys Leu Lys Ser
1               5                   10                  15

<210> SEQ ID NO 83
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (23)..(23)
<223> OTHER INFORMATION: Any amino acid

<400> SEQUENCE: 83

Ser Met Ala Gln Asp Ile Ile Ser Thr Ile Gly Asp Leu Val Lys Trp
1               5                   10                  15
Ile Ile Gln Thr Val Asn Xaa Phe Thr Lys Lys
            20                  25

<210> SEQ ID NO 84
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Leu Leu Gly Asp Phe Phe Arg Lys Ser Lys Glu Lys Ile Gly Lys Glu
1               5                   10                  15
Phe Lys Arg Ile Val Gln Arg Ile Lys Gln Arg Ile Lys Asp Phe Leu
            20                  25                  30
Ala Asn Leu Val Pro Arg Thr Glu Ser
        35                  40

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Ala Trp Arg Lys Ala Phe Arg Trp Ala Trp Arg Met Leu Lys Lys
1               5                   10                  15
Ala Ala

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Leu Lys Leu Lys Leu Lys Leu Lys Leu Lys Leu Lys Leu Lys Leu
1               5                   10                  15
Lys Leu

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Leu Pro Ile Pro Asn Pro Leu Leu Gly Leu Asp Ser
1               5                   10
```